United States Patent [19]
Quax et al.

[11] Patent Number: 5,935,831
[45] Date of Patent: *Aug. 10, 1999

[54] MUTATED β-LACTAM ACYLASE GENES

[75] Inventors: Wilhelmus Johannes Quax, Voorschoten; Onno Misset, Delft; Jan Metske Van Der Laan, Groningen; Herman B. M. Lenting, Pijnacker, all of Netherlands

[73] Assignee: Gist-Brocades, N.V., Delft, Netherlands

[ * ] Notice: This patent is subject to a terminal disclaimer.

[21] Appl. No.: 08/541,780

[22] Filed: Oct. 10, 1995

Related U.S. Application Data

[63] Continuation of application No. 07/731,157, May 9, 1991, Pat. No. 5,457,032.

[30] Foreign Application Priority Data

Apr. 18, 1990 [EP] European Pat. Off. .............. 90200962

[51] Int. Cl.⁶ .............................. C12N 15/01; C12N 9/84; C12N 9/80
[52] U.S. Cl. ...................... 435/172.3; 435/228; 435/230; 435/252.3; 435/252.33; 435/252.34; 435/254.11; 435/254.5; 435/320.1
[58] Field of Search ...................... 435/230, 228, 435/252.3, 43, 254.11, 254.5, 252.33, 252.34, 320.1, 172.1, 172.3

[56] References Cited

U.S. PATENT DOCUMENTS

| | | | |
|---|---|---|---|
| 4,774,179 | 9/1988 | Ichikawa et al. | 435/51 |
| 5,168,048 | 12/1992 | Quax | 435/66.1 |
| 5,192,678 | 3/1993 | Iwami et al. | 435/228 |
| 5,320,948 | 6/1994 | Iwami et al. | 435/47 |
| 5,457,032 | 10/1995 | Quax et al. | 435/43 |
| 5,695,978 | 12/1997 | Quax | 435/230 |

FOREIGN PATENT DOCUMENTS

| | | |
|---|---|---|
| A-0283218 | 9/1988 | European Pat. Off. . |
| A-0322032 | 6/1989 | European Pat. Off. . |
| 0 453 048 | 10/1991 | European Pat. Off. . |
| 0558241A2 | 9/1993 | European Pat. Off. . |
| WO 95/12680 | 5/1995 | WIPO . |

OTHER PUBLICATIONS

Joris et al., *Biochem. J.*, 250, 313–324 (1988).
Martin et al., *Biochim. Biophys. Acta*, 1037 (2), 133–139 (1990).
Prieto et al., *Appl. Microbiol. Biotechnol.*, 33 (5), 553–559 (1990).
Schumacher et al., *Nucleic Acids Research*, (1986) 14: 5713–5727.
Barbero et al., *Gene*, (1986) 49: 69–80.
Daumy, *J. Bacteriol*, (1985) 163: 1279–1281.
Williams et al., *Cell Biochem.*, (1985) 9B/supplement: 99.
Forney et al., *Applied & Enviromental Microbiology*, (1989) 55: 2550–2555.
Forney et al., *Applied & Enviromental Microbiology*, (1989) 55: 2556–2560.
Matsuda et al., *J. Bacteriol*, (1987) 169: 5815–5820.
Matsuda et al., *J. Bacteriol*, (1987) 169: 5821–5826.
Norrander et al., *Gene*, (1983) 26: 101–106.
Stanssens et al., *Nucleic Acids Research*, (1989) 12: 4441–4454.

*Primary Examiner*—Charles L. Patterson, Jr.
*Attorney, Agent, or Firm*—McDonnell Boehnen Hulbert & Berghoff

[57] ABSTRACT

New mutant β-lactam acylases are provided exhibiting altered substrate specificities. These β-lactam acylases are obtained by expression of a gene encoding said β-lactam acylase and having an amino acid sequence which differs at least in one amino acid from the wild-type β-lactam acylase.

24 Claims, 42 Drawing Sheets

FIG. 5A

```
                                    510        520        530        540
                                    ATGCAGAAAGGGCTTGTCGTACGGGCTTGT
                                     M  Q  K  G  L  V  R  T  G  L  V
                                     1
        550        560               570        580        590        600
GGCCGCTGGTTTGATCTTGGGTTGGGCGGG    CACCGGCACCCACGCGCAAGTCAGTCGGT
 A  A  G  L  I  L  G  W  A  G     A  P  T  H  A  Q  V  Q  S  V
 12
        610        620        630           640        650        660
AGAGGTGATGCGGGACAGTTATGGCGTGCCG    CACGTCTTTGCCGACAGCCACTATGGCTT
 E  V  M  R  D  S  Y  G  V  P      H  V  F  A  D  S  H  Y  G  L
 32
        670        680        690           700        710        720
GTATTACGGCTATGGTGTTATGCGGTCCG    CAAGACCGTCTGTTCCAGATGGACATGGCGCG
 Y  Y  G  Y  G  Y  A  V  A  Q     D  R  L  F  Q  M  D  M  A  R
 52
        730        740        750           760        770        780
TCGCTCCTTGTCGGCACACAACCGCCGTCT    TAGGCCCTGGTGAGCAAGATGCCTACGT
 R  S  F  V  G  T  T  A  A  V     L  G  P  G  E  Q  D  A  Y  V
 72
        790        800        810           820        830        840
CAAGTACGACATGCAGGTGCGCGAGAACTT    CACCCCGGCTTCCATACAGCGGCAGATCGC
 K  Y  D  M  Q  V  R  Q  N  F     T  P  A  S  I  Q  R  Q  I  A
 92
        850        860        870           880        890        900
GGCCTTGTCCAAGGATGAGCGCGATATTTT    CGTGGCTATGCCGATGGCTATAACGCCTA
 A  L  S  K  D  E  R  D  I  F     R  G  Y  A  D  G  Y  N  A  Y
 112
```

```
                    910              920              930              940              950              960
          TCTGGAGCAGGTGCGGCGTCGCCCTGAGTTGCTGCCCAAAGAATATGTGGATTTGATTT
           L   E   Q   V   R   R   R   P   E   L   L   P   K   E   Y   V   D   F   D   F
          132

970              980              990             1000             1010             1020
          CCAGCCCGAGCCGCTGACCGACTTTGATGTGGTCATGATCTGGGTGGGCTCCATGGCCAA
           Q   P   E   P   L   T   D   F   D   V   V   M   I   W   V   G   S   M   A   N
          152

1030             1040             1050             1060             1070             1080
          TCGCTTCTCCGACACGAATCTGGAAGTGACGGCCACTGGCCATGCGTCAGTCTCTGGAGAA
           R   F   S   D   T   N   L   E   V   T   A   L   A   M   R   Q   S   L   E   K
          172

1090             1100             1110             1120             1130             1140
          ACAGCACGGCCCCGAACGGGAGGCCCGTGCCCTTGTTTGATGAGCTGCTGTGGATCAATGACACT
           Q   H   G   P   E   R   G   R   A   L   F   D   E   L   L   W   I   N   D   T
          192

1150             1160             1170             1180             1190             1200
          AACAGCTCCCACTACGGTTCCGGCCCGCTGCCGAGCACAAGCCGCAGGCACAAGCAGG
           T   A   P   T   T   V   P   A   P   A   A   E   H   K   P   Q   A   Q   A   G
          212

1210             1220             1230             1240             1250             1260
          GACGCAGGATCTGGCTCATGTTTCCTCGCCAGTACTGGCTACCGAGCTAGAGCGCCAGGA
           T   Q   D   L   A   H   V   S   S   P   V   L   A   T   E   L   E   R   Q   D
          232

1270             1280             1290             1300             1310             1320
          CAAGCACTGGGGCGGCCGTGGGCCCGGACTTCGGCCCAAGGCTAGCAACCTGTGGAGCAC
           K   H   W   G   G   R   G   P   D   F   F   A   P   K   A   S   N   L   W   S   T
          252
```

FIG. 5B

```
         1330           1340           1350           1360           1370          1380
TCGCCCCGAGGAGTGCAGGAGGGCTCGACCGTACTGATCAACGGCCCACAGTTTGGCTG
   R  P  E  R  V  Q  E  G  S  T  V  L  I  N  G  P  Q  F  G  W
272
         1390           1400           1410           1420           1430          1440
GTACAACCCGGCCTACACCTATGGCATTGGCTTGCATGGCGCCGGCTTCGATGTGGTGGG
   Y  N  P  A  Y  T  Y  G  I  G  L  H  G  A  G  F  D  V  V  G
292
         1450           1460           1470           1480           1490          1500
TAATACGCCCTTTGCCTATCCGATCGTGTTGGCACCAATAGCGAGATTGCCTGGGGG
   N  T  P  F  A  Y  P  I  V  L  F  G  T  N  S  E  I  A  W  G
312
         1510           1520           1530           1540           1550          1560
GGCGACTGCTGGCCCCGCAAGATGTGGTGGACATATATCAGGAGAAATTGAACCCCTCGCG
   A  T  A  G  P  P  Q  D  V  V  D  I  Y  Q  E  K  L  N  P  S  R
332
         1570           1580           1590           1600           1610          1620
TGCCCGATCAGTACTGGTTCAACAATGCCTGGCGCACGATGGAGCAGCGCAAGGAACGTAT
   A  D  Q  Y  W  F  N  N  A  W  R  T  M  E  Q  R  K  E  R  I
352
         1630           1640           1650           1660           1670          1680
CCAGGTACGCGGTCAGGCTGATCGGGGAAATGACGATCTGGCGCGTGCACGGCCCCTGT
   Q  V  R  G  Q  A  D  R  E  M  T  I  W  R  T  V  H  G  P  V
372
         1690           1700           1710           1720           1730          1740
GATGCAGTTTGATTACGATCAGGGCGCGTACAGCAAGAAACGCAGCTGGGATGGCTA
   M  Q  F  D  Y  D  Q  G  A  A  Y  S  K  K  R  S  W  D  G  Y
392
```

FIG. 5C

```
        1750        1760        1770        1780        1790        1800
TGAGGTGCAGTCCTTGCTAGCCTGGTTGAACGTGGCCAAGGCCCGCAACTGGACGGAGTT
  E  V  Q  S  L  L  A  W  L  N  V  A  K  A  R  N  W  T  E  F
 412

1810        1820        1830        1840        1850        1860
TCTGGATCAAGCCAGCAAGATGGCGATTTCGATCAACTGTACTACGCCGACAAGCACGG
  L  D  Q  A  S  K  M  A  I  S  I  N  W  Y  Y  A  D  K  H  G
 432

1870        1880        1890        1900        1910        1920
CAATATTGGTTATGTCTCGCCGGCCTTCCTGCCCCAGCGTCCTGCCGATCAGGACATCCG
  N  I  G  Y  V  S  P  A  F  L  P  Q  R  P  A  D  Q  D  I  R
 452

1930        1940        1950        1960        1970        1980
TGTCCCTGCCAAGGGGGATGGCAGCATGGAGTGGCTGGGCATCAAGAGTTTCGACGCGAT
  V  P  A  K  G  D  G  S  M  E  W  L  G  I  K  S  F  D  A  I
 472

1990        2000        2010        2020        2030        2040
TCCCAAAGCCTACAATCCACCCCAGGGCTATCTGGTCAACTGGAACAACAAGCCTGCGCC
  P  K  A  Y  N  P  P  Q  G  Y  L  V  N  W  N  N  K  P  A  P
 492

2050        2060        2070        2080        2090        2100
GGACAAAACCAATACGGATACTTACTATTGGACCTATGGCGACCGCATGAATGAACTGGT
  D  K  T  N  T  D  T  Y  Y  W  T  Y  G  D  R  M  N  E  L  V
 512

2110        2120        2130        2140        2150        2160
CAGTCAGTACCAGCAGAAAGACCTCTTCAGTGTGCAGGAGATCTGGGAGTTCAATCAAAA
  S  Q  Y  Q  Q  K  D  L  F  S  V  Q  E  I  W  E  F  N  Q  K
 532
```

FIG. 5D

```
       2170        2180        2190        2200        2210        2220
AGCCTCCTATAGCGATGTGAACTGGCGCTACTTCCGCCCACATCTGGAAAAGCTGGCGCA
 A  S  Y  S  D  V  N  W  R  Y  F  R  P  H  L  E  K  L  A  Q
552
       2230        2240        2250        2260        2270        2280
ACAGCTGCCGGCCGACGATAGCAGCAAGGCGGCCGATGATGTTGCTCGCCTGGGATGG
 Q  L  P  A  D  D  S  S  K  A  A  L  T  M  L  L  A  W  D  G
572
       2290        2300        2310        2320        2330        2340
AATGGAACAGGATCAGGGAGGGCAAATGCCGGCGGTGCTCTTCAAGACCTG
 M  E  Q  D  Q  G  G  Q  N  A  G  P  A  R  V  L  F  K  T  W
592
       2350        2360        2370        2380        2390        2400
GCTGGAAGAAATGTACAAGCAGGTCTTGATGCCGGTGGTGCCTGAATCGCGCCAT
 L  E  E  M  Y  K  Q  V  L  M  P  V  V  P  E  S  H  R  A  M
612
       2410        2420        2430        2440        2450        2460
GTATAGCCAGACTGGTTTGCCACGCAGCAAGTCCCAACCCCGGTTCCATCAACTTGAG
 Y  S  Q  T  G  F  A  T  Q  Q  G  P  N  P  G  S  I  N  L  S
632
       2470        2480        2490        2500        2510        2520
CATGGCACCAAGGTCTTGTTGCCGTGCCTTGGTGTGGAAGCCCATCCCGATCCCAAGCG
 M  G  T  K  V  L  L  R  A  L  V  L  E  A  H  P  D  P  K  R
652
       2530        2540        2550        2560        2570        2580
TGTGAATGTCTTTGGTGAGCGTTCGTCTCAGAAATCATGCACACAGCTTTGCAAAATGC
 V  N  V  F  G  E  R  S  S  Q  E  I  M  H  T  A  L  Q  N  A
672
```

FIG. 5E

```
           2590           2600           2610           2620           2630           2640
GCAGGCCCCGCTTGAGCAGGAGCAGGGCCGCTCAGATGGCCGCTGGACCATGCCGACCTC
   Q  A  R  L  S  Q  E  Q  G  A  Q  M  A  R  W  T  M  P  T  S
  692
           2650           2660           2670           2680           2690           2700
CGTGCATCGTTTCAGGAGTTCTGCGACGCAAGAACTTCACGGGAACCCCGCAGATGCCTGGCAATAC
   V  H  R  F  S  D  K  N  F  T  G  T  P  Q  T  M  P  G  N  T
  712
           2710           2720           2730           2740           2750           2760
CTTTGCCTTTACCGGCTATCAGAATCGAGGCACGGAAAATAACCGCGTGGTGTTTGATGC
   F  A  F  T  G  Y  Q  N  R  G  T  E  N  N  R  V  V  F  D  A
  732
           2770           2780           2790           2800           2810           2820
CAAGGGCGTGGAGTTCTGCGACGCCATGCCGCCCCCGGCCAAAGCGGTTTCACGACCGCAA
   K  G  V  E  F  C  D  A  M  P  P  G  Q  S  G  F  D  T  R  N
  752
           2830           2840           2850           2860           2870           2880
TGGAGTGCGCAGCCCGCATTATGAGGATCAGTGTGAAGTTGTACGAGAACTTCGAGTGCAA
   G  V  R  S  P  H  Y  E  D  Q  L  K  L  Y  E  N  F  E  C  K
  772
           2890           2900           2910           2920           2930           2940
GACGATGGATGTGACGCATGCCGGACATTCGTCGTAATGCCAAGCAGCACGATGCTGTT
   T  M  D  V  T  H  A  D  I  R  R  N  A  Q  S  S  T  M  L  L
  792
           2950           2960
GATTCAGCCTCAGCCTTAA
   I  Q  P  Q  P  *
  812
```

FIG. 5F

```
111                        131            141              151               161
ATGCTGAGAGTTCTGCACCGGGCCGCTCCGCCTTGGTTGTTATGGCGACTGTGATCGGCTT
 M  L  R  V  L  H  R  A  A  S  A  L  V  M  A  T  V  I  G  L 171        181             191              201              211              221
GCGCCCCGCGTCGCCTTTGCCTGGCCAGCCGACCTCGACGCCAGGCCGATTGCG
 A  P  A  V  A  F  A  L  A  E  P  T  S  T  P  Q  A  P  I  A 231        241              251              261              271              281
GCCTATAAACCGAGAAGCAATGAGATCCTGTGGACGGTACGGCGTCCCGACATCTAC
 A  Y  K  P  R  S  N  E  I  L  W  D  G  Y  G  V  P  H  I  Y 291        301              311              321              331              341
GGGGTCGACGCGCCCTCAGCCTTCTACGGCTATGGCTGGGCCCAGGCGCGCAGCCAGGGC
 G  V  D  A  P  S  A  F  Y  G  Y  G  W  A  Q  A  R  S  Q  G 351        361              371              381              391              401
GACAATATCCTGCGCCTGTATGGAGAAGCGCGGGGCAAGGGGGCCGAATACTGGGGCCCG
 D  N  I  L  R  L  Y  G  E  A  R  G  K  G  A  E  Y  W  G  P 411        421              431              441              451              461
GATTACGAACAGACGACCGTCTGGCTGCTGACCAACGGCGTGCCGAGCGGCTCAGCAG
 D  Y  E  Q  T  T  V  W  L  L  T  N  G  V  P  E  R  A  Q  Q 471        481              491              501              511              521
TGGTATGCGCAGCAGTCGCCTGATTCCGGCCAACCTCGACGCCCTTCGCGGCGGCATC
 W  Y  A  Q  Q  S  P  D  F  R  A  N  L  D  A  F  A  A  G  I 531        541              551              561              571              581
AACGGCTATGCCGCAGCAGAACCCGACGACATCTCGCCCGACGTGCGGCAGGTGCTGCCG
 N  A  Y  A  Q  Q  N  P  D  D  I  S  P  D  V  R  Q  V  L  P
```

FIG. 13A

```
591                  601                  611                  621                  631                  641
GTTTCCGGCCGACGTGGTGGCCCACGCCCACCGCCCTGATGAACTTCCTCTATGTCGCA
 V  S  G  A  D  V  V  A  H  R  L  M  N  F  L  Y  V  A 651                  661                  671                  681                  691                  701
TCGCCCGGCGACCCTGGGCGAGGGCGACCCGCCTGACCTCGCCGATCAAGGATCCAAC
 S  P  G  R  T  L  G  E  G  D  P  P  D  L  A  D  Q  G  S  N 711                  721                  731                  741                  751                  761
TCCTGGCGGTGGCCCCGGAAAGACGGCGAACGGGAACCCCTGTCTGCAGAACCCG
 S  W  A  V  A  P  G  K  T  A  N  G  N  A  L  L  Q  N  P 771                  781                  791                  801                  811                  821
CACCTGTCCTGGACGACGACTACTTCACCTACTACGAGGCGCATCTCGTCACGCCGAC
 H  L  S  W  T  T  D  Y  F  T  Y  Y  E  A  H  L  V  T  P  D 831                  841                  851                  861                  871                  881
TTCGAAATCTATGGCCGACCCAGATCGGCCGTCCTGCCGGTCATCCGCTTCGCCTTCAACCAG
 F  E  I  Y  G  A  T  Q  I  G  L  P  V  I  R  F  A  F  N  Q 891                  901                  911                  921                  931                  941
CGGATGGCAATCACCAATACCGTCAACGGCATGGTGGGGCCACCAACTATCGGCTGACG
 R  M  G  I  T  N  T  V  N  G  M  V  G  A  T  N  Y  R  L  T 951                  961                  971                  981                  991                  1001
CTTCAGGACGGCTATCTCTATGACGGTCAGGTCCGCCCGTTCGAGCGGCCTCAGGCC
 L  Q  D  G  Y  L  Y  D  G  Q  V  R  P  F  E  R  P  Q  A
```

FIG. 13B

```
1011                1021         1031         1041         1051         1061
TCGTATCGCCTGCCTCAGGCGGACGACGGTCGACAACGGTCGACAAGCCGTTGAGATCCGTCC
 S   Y   R   L   R   Q   A   D   G   T   T   V   D   K   P   L   E   I   R   S 1071                1081         1091         1101         1111         1121
AGCGTCCATGGCCCGGTCTTCGAGCGCGGACGCCACGGCACCGCCGTTCGGGTCGCC
 S   V   H   G   P   V   F   E   R   A   D   G   T   A   V   A   V   R   V   A 1131                1141         1151         1161         1171         1181
GGTCTGGACCGGCCCGGCATGCTCGAGCAGTATTTCGACATGATCACGGCGACAGCTTC
 G   L   D   R   P   G   M   L   E   Q   Y   F   D   M   I   T   A   D   S   F 1191                1201         1211         1221         1231         1241
GACGACTACGAAGCCGCTTTGGCCCGGATGCAGGTGCCGACCTTCAACATCGTCTACGCC
 D   D   Y   E   A   A   L   A   R   M   Q   V   P   T   F   N   I   V   Y   A 1251                1261         1271         1281         1291         1301
GACCGCGAAGGGACCATCAACTACAGCTTCAACGGCGTGGCCCCAAACGGGCCGAGGGC
 D   R   E   G   T   I   N   Y   S   F   N   G   V   A   P   K   R   A   E   G 1311                1321         1331         1341         1351         1361
GACATCGCCTTCTGGCAGGGCCTCGTGCCCGGCGATTCCTCGCGTTACCTGTGGACCGAG
 D   I   A   F   W   Q   G   L   V   P   G   D   S   S   R   Y   L   W   T   E 1371                1381         1391         1401         1411         1421
ACACACCCGCTGGACGATCTGCCGCGTCACCAATCCCCGGGCGGCTTCGTGCAGAAC
 T   H   P   L   D   D   L   P   R   V   T   N   P   P   G   G   F   V   Q   N
```

FIG. 13C

```
1431                1441                1451                1461                1471                1481
TCCAATGATCCGGCCTGGACGCCGACCTGGCCGTCCGTGGCCCGTCACCTACACGCCCAAGGACTTCCCC
 S   N   D   P   P   W   T   P   T   W   P   V   T   Y   T   P   K   D   F   P 1491                1501                1511                1521                1531                1541
TCCTATCTGGCGCCCCAGACGCCCCATTCCCTGCGTGCCAACAAAGCGTGCGTCTGATG
 S   Y   L   A   P   Q   T   P   H   S   L   R   A   Q   Q   S   V   R   L   M 1551                1561                1571                1581                1591                1601
TCCGAGAACGACGACCTGACGCTGGAGCGCTTCATGGCGCTGCAGTTGAGCCATCGCGCC
 S   E   N   D   D   L   T   L   E   R   F   M   A   L   Q   L   S   H   R   A 1611                1621                1631                1641                1651                1661
GTCATGGCCGACCGCACCTTGCCGGACCTGATCCCCGCCGCCCTGATCGACCCCGATCCC
 V   M   A   D   R   T   L   P   D   L   I   P   A   A   L   I   D   P   D   P 1671                1681                1691                1701                1711                1721
GAGGTCCAGGCGGCGGCCCGCCTGCTGGCCGCGGTGGATCGCGAGTTCACCAGCGACAGC
 E   V   Q   A   A   A   R   L   L   A   A   W   D   R   E   F   T   S   D   S 1731                1741                1751                1761                1771                1781
CGGCGCCGCCCTGTCGTTGAGGAATGGGCGCGTCGTTCGCCGGCCAGAATTCGCAGGC
 R   A   A   L   L   F   E   E   W   A   R   L   F   A   G   Q   N   P   A   G 1791                1801                1811                1821                1831                1841
CAGGCCGGCTTCGCCACGCCCTGGTCGCTGGATAAGCCGGTCAGCACGCCTTACGGCGTC
 Q   A   G   F   A   T   P   W   S   L   D   K   P   V   S   T   P   Y   G   V
```

FIG. 13D

Alignment of Type-II acylases signal sequence

```
E.col   M KNRNRMIVN CVTASLMYYWSL PALA                          26
K.cit   * *******GI ICCS S***                          26
A.fae   *Q*GLV*    TGL*A*G*ILG*AGA*TH*                         26
SE-83   *                                                       1
SY-77   *LRVLH*AASALVMATVIGLAPAVAF***                          29
```

α-subunit

```
                              ---D-----H--
E.col                         EQSSSEIKIVRDEYGMPHIY             46
K.cit                         ASPPT*V*************             46
A.fae                         QVQSVEVM*S*V**VF             44
SE-83   TMAAKTDREALQAALPPLSGSLSIPGL*APVRVQ**GW*I***K            45
SY-77       EPTST PQAPIAAYKP RSNEIL   W*G***V*****             60

E.col  ANDTWHLFYGYGYVVAQDRLFQME MAR  RSTQGTVAEVLG  KDFVKFDKDIRRNY   99
K.cit  *DYR************** *  ******S**  *AS*Q    99
A.fae  *DSHYG*Y****A*****D *  FVT*A*PGEQDAYY*MQV*Q*F 101
SE-83  *SGEADAYRAL*F*H********* LT*  *KAL*RAW  AEAAEA*ILV**LG    98
SY-77  GV*APSA******W  **A*S HGDNIL*LYGEAR*KG**YW*  P*YEQTTVWLLT*G  113
```

FIG. 14A

```
E.col  WPDAIRAQIAALSPEDMSILQGYADGMNAWIDKVNTNPETLLPKQFNTGFTPKRWEPFD  159
K.cit  *S**SAK************************AS*DK*QS**KH*****  159
A.fae  T*AS*QR*****KDERD*FR*****Y**YLEQ*RRR**  ****EYVD*D*Q*EPLTD**  160
SE-83  MEKVC*RDFE**GA*AKDM*RA*VA*V**FL  ASGA*   **IEYGLL*AE*EP***WH  153
SY-77  V*ERAQQWY*QQ**DFRAN*DAF*A*IY   AQQD   DISPEVRQVL*VSGADVV  167

S
E.col  VAMIFVGTMANRFSDSTSEIDNLAL    LTALKDKYGVSQGMAVFNQLKWLVNPSAPT  214
K.cit  **************************    *V***DE*******************  214
A.fae  *VWS*****TNL*VTA***M    RQS*EKQH*PER*R*L*DE*L*INDTT***  215
SE-83  SIAVMRRLGLLMG*VWFKLWRM***PVVGAAN***LR*DDGGQ    D*LCIPPGVEAE  208
SY-77  AHAHRLMNFLYVA*PGRTLGEGDPPDLADQG                                198

E.col  TIAVQ        ESNYPLKFNQQNSQTA                                    235
K.cit  *AR        S***DLT***                                    235
A.fae  *VPAP   AAEHK*   QA*AGT*DLA                                      236
SE-83  RLEADLAAALRPAVDAL**AMGGDASD*AGGG                                 239
SY-77                                                                   198 connecting peptide
E.col  ALL  PRYDLPAPMLDRPAK     GADGALLALTAGKNRETIVAQFAQGGANGLAGYPTT   289
K.cit  *VQ**********    *T***VI****A* N**********   289
A.fae       HVSSPV* ATE*E*QD*HW*GR*PDF*PK*                             265
SE-83                                                                   239
SY-77                                                                   198
```

FIG. 14B

```
ß-subunit
-----S-------------
E.col  SNMWVIGKSKAQDAKAIMVNGPQFGWYAPAYTYGIG LHGAGYDVTGNTPFAYPGLGFGH   348
K.cit  ******N*****************A************************V***         348
A.fae  **L*STRPERV*EGSTVLI*****************N*****************IVL**T   324
SE-83  **N*AVAPGRTATGRP*LAGD*H RVFEIPGM*AQHH*ACDRF*MI*L*VPGV**FPHFA    298
SY-77  **S*AVAPG*TANGN*LLLQN*HLS*TTDYF***YEAH**VTPDFEIY*A*QIGL* VIRFA  257

E.col  NGVISWGSTAGFGDDVDIFAERLSAE   KPGYYLHNG KWV KMLSREETITVKNGQAE    403
K.cit  ***************K***   *Q* E *K*ADP*    403
A.fae  *SE*AA**PQ*V***YQ*K*NPS  RADQ*WF*N A*R T*EQ*K*R*Q*RGQADR    379
SE-83  HKVAYCVM*IH*LYL* QF**DGRTARFG *E FE PVAW*RDR*A*RG*ADR       353
SY-77  F*QRMGITN*VNGMVGATNY   **TLQDGGYL*DG QVRPFERRQA*YRLRQADGTTVDK   314

E.col  TFTVWRT VHGNILQTDQTTQTAYAKSRAWDGKE VASLLAWTHQMKA   KNWQEWTQQA   459
K.cit  ***** LDVIKTR****AA* A******   *P******  459
A.fae  EM*IW** ***PVM*F*YDQGA**S*K*S**Y* *Q*****LNVA** R**T*FLD**     435
SE-83  E DIVE* R**PVIAG* PLEG*ALTL*SVQFA*THL*FDCLTRMPG*S TVA*LYDATR   409
SY-77  PLEI *SS***PVFER   ADG***V* V*VA *LD RPGM*EQYFD*ITADSFDDYEAAL*  368
                                 -D---

E.col  AKQALTINWYYADVNGNIGYVHTGAYPDRQSGHDPRLP  VPG TGKWDWKGLLPFEMNP    516
K.cit  ****************************P******    ** D***********S*DL**   515
A.fae  S*M*IS*****KH*****SPAFL*Q*PADQ*I*V*     AK* D*SME*L*IKS*DAI*   492
SE-83  GWGLIDH*LVAG**A*S**HLVRARV*S* PRENGW**  ****WS*EHE*R*WI*H*AM*  466
SY-77  RM*VPTF*IV****RE*T*N*SFN*VA*K*AE*DIAFWQGL***DSSRYL*TETH*LDDL*  428
```

FIG. 14C

```
E.col  KVYNPQSGYIANWNNSPQKDYPASDLFAFLWGGADRVTEIDRLLEQKPRLTADQAWDVIR  576
K.cit  ****************************************************TI*DKQ***F**********  575
A.fae  *AYPQLV****K*APLV**K*AP**KTNT*TYYWTY*  **MN*LVSQYQ**DLFSVQEI*EFNQ  550
SE-83  R*ID*PG*L*VTA**RVVA*  DHP*YLCTDCHPPY*AER*MER*VAS*AFAV*H*AAIHA  525
SY-77  R*T**PG*FVQ*S*DP*TTPTWPVTYTPKD FPSYLAPQTPHS*RA   QQSVRLMSENDD  485

-D-

E.col  QT SRQDLNLRLFLPTLQAATSGLTQSDPRRQLVETLTRWDGINLLNDDGKTWQQPGSAI  635
K.cit  ** *LR** ******A KD**AN*AEN*****DK*AS****E*V******Y********  633
A.fae  KA *YS*V*W*Y*R*HLEKLAQQ*PAD*SSKAALTM*LA***MEQ  *Q*GQNAG*AR V  606
SE-83  D*L*PHVGL**AR*EAL     *IQG*L*AEE*RQIA*RMDAGSQAASAYNAFRRA  580
SY-77  L*LE*FMALQLSHR AV     MADRTL* DLIPAA*  I*PD EVQA AARLLAAWDRE  534

E.col  KRTVVAAVP  MPFDKWYSASGYETTQDGPTGSLNISVGAKILYE  687
K.cit  *L*  A*G*********I*L*M*T*V*LR  685
A.fae  *QVLMPV  ESHRAM*QT*FA*Q*GPNP***I*L*M*T*V*LR  659
SE-83  *TRL*TAR*G*EQAIAHPF****PGVS*QGQVWW*VPTLLRN* DA*M*KGWSNDEA*S*  639
SY-77  FTSDSRA AL*FEEWARFL*   GQNFAGQAGF*TPTSL  *K*VSTPYGVRDP*AAVD  587
```

FIG. 14D

```
E.col  AVQGDKSPIPQAVDLFAGKPQQEVVLAALEDTWETLSKRYGNNVSNWKTPAMALTFRANN    747
K.cit  *L***************G****E****I****D*A*Q*******D*TG***********    745
A.fae  *LVLEAH*D*KR*NV*GERSSIMHTQNAQAR**QEQ*AQMAR*TM*TSVHR*SDKN    719
SE-83  *LSVATQNLTGRGWGEEHR*RFTHP*S*QFPA*AA*    L*P** RPIGGDGD*VLA*    693
SY-77  QLRTAIANLTKRKYGAIDR*FGDASRMI*N*VNVPGAAG***LG*FRVFTTS D PDE*    644

-----------S------------
E.col  FFGVPQAAAEETRHQAEYQNRGTENDMIVFSPTTSDRPVLAWDVVAPGQSGFIAPDGTVD    807
K.cit  *************K*A****************SGN****************KA*        805
A.fae  *T*T**TMPGN*FAFTG******NRV**DAKGVE    FC *AMP*****TDNR*VRS     775
SE-83   GL**S*GP*     *T*    *  ALSRY***DVGNW*  NSR* **FH*A**HP*    S 735
SY-77  GVRT*VHG *           TW    V AMIE  **T  **R*YGLMSY*N*RQPG    T 681

-----H--D------
E.col  KHYEDQLKMYENFGRKSLWLTKQDVEA   HKESQEVLHVQR                      846
K.cit  ****D*****S*******P***DE     **********Q***                    844
A.fae  PEL**EC*TMDV*HA*IRR  NAQ*STM*LI*PQP                    816
SE-83  PA NAPWSDCAIVPM*YSW*RI*AEAVT*** * *PA                      773
SY-77  TSIERVSRADFRE*L*RREQ*      AVRTPFNFKP                  720
```

FIG. 14E

Amino acid residue selection in the A. faecalis α-subunit

Number of Residues selection 1: identical and similar
(hydrophobic + charged + polar)                          169 (80%)
selection 2: identical and similar
(selection 1 minus Asp, Glu, Arg, Lys)                   119 (57%)
selection 3: identical and similar
(selection 2 minus conserved Gly and Pro)                102 (49%)
selection 4: identical and similar hydrophobic
residues                                                  74 (35%)
selection 5: identical hydrophobic residues               44 (21%)

The one-letter code preceding the numbers in the row represents
the amino acids in the Alcaligenes faecalis Type-IIA acylase.

|   | 1 | 2 | 3 | 4 | 5 |   | 1 | 2 | 3 | 4 | 5 |   | 1 | 2 | 3 | 4 | 5 |
|---|---|---|---|---|---|---|---|---|---|---|---|---|---|---|---|---|---|
| Q | 29 | 29 | 29 |    |    | Q | 61 | 61 | 61 |    |    | F | 101 | 101 | 101 | 101 |     |
| S | 30 |    |    |    |    | D | 62 |    |    |    |    | P | 103 | 103 |     |     |     |
| V | 31 | 31 | 31 | 31 |    | R | 63 |    |    |    |    | S | 105 | 105 | 105 |     |     |
| E | 32 |    |    |    |    | L | 64 | 64 | 64 | 64 | 64 | I | 106 | 106 | 106 | 106 | 106 |
| V | 33 | 33 | 33 | 33 |    | F | 65 | 65 | 65 | 65 | 65 | Q | 107 |     |     |     |     |
| H | 34 | 34 | 34 | 34 |    | Q | 66 | 66 | 66 |    |    | Q | 109 | 109 | 109 |     |     |
| R | 35 |    |    |    |    | M | 67 | 67 | 67 | 67 | 67 | I | 110 | 110 | 110 | 110 | 110 |
| D | 36 |    |    |    |    | D | 68 |    |    |    |    | A | 111 | 111 | 111 | 111 | 111 |
| S | 37 |    |    |    |    | M | 69 | 69 | 69 | 69 | 69 | A | 112 | 112 | 112 |     |     |
| Y | 38 | 38 | 38 | 38 | 38 | A | 70 | 70 | 70 | 70 | 70 | L | 113 | 113 | 113 | 113 | 113 |
| G | 39 | 39 |    |    |    | R | 71 |    |    |    |    | S | 114 | 114 | 114 |     |     |
| V | 40 | 40 | 40 | 40 |    | R | 72 |    |    |    |    | D | 116 |     |     |     |     |
| P | 41 | 41 |    |    |    | S | 73 | 73 | 73 |    |    | E | 117 |     |     |     |     |
| H | 42 | 42 | 42 |    |    | G | 76 | 76 |    |    |    | D | 119 |     |     |     |     |
| V | 43 | 43 | 43 | 43 |    | T | 77 | 77 | 77 |    |    | I | 120 | 120 | 120 | 120 | 120 |
| F | 44 | 44 | 44 | 44 |    | V | 78 |    |    |    |    | R | 122 |     |     |     |     |
| A | 45 | 45 | 45 | 45 | 45 | A | 79 | 79 | 79 |    |    | G | 123 | 123 |     |     |     |
| D | 46 |    |    |    |    | V | 81 | 81 | 81 | 81 | 81 | Y | 124 | 124 | 124 | 124 | 124 |
| S | 47 |    |    |    |    | L | 82 | 82 | 82 | 82 | 82 | A | 125 | 125 | 125 | 125 | 125 |
| H | 48 | 48 | 48 |    |    | G | 83 | 83 |    |    |    | D | 126 |     |     |     |     |
| Y | 49 | 49 | 49 | 49 |    | D | 88 |    |    |    |    | G | 127 | 127 |     |     |     |
| L | 51 | 51 | 51 | 51 | 51 | Y | 90 | 90 | 90 | 90 |    | N | 129 | 129 | 129 |     |     |
| Y | 52 | 52 | 52 | 52 |    | V | 91 | 91 | 91 | 91 | 91 | A | 130 | 130 | 130 | 130 | 130 |
| Y | 53 | 53 | 53 | 53 | 53 | K | 92 |    |    |    |    | Y | 131 | 131 | 131 | 131 |     |
| G | 54 | 54 |    |    |    | Y | 93 | 93 | 93 | 93 |    | L | 132 | 132 | 132 | 132 |     |
| Y | 55 | 55 | 55 | 55 | 55 | D | 94 |    |    |    |    | E | 133 |     |     |     |     |
| G | 56 | 56 |    |    |    | Q | 96 |    |    |    |    | Q | 134 |     |     |     |     |
| Y | 57 | 57 | 57 | 57 | 57 | V | 97 | 97 | 97 | 97 |    | V | 135 | 135 | 135 | 135 | 135 |
| A | 58 | 58 | 58 | 58 |    | R | 98 |    |    |    |    | R | 136 |     |     |     |     |
| V | 59 | 59 | 59 | 59 | 59 | Q | 99 |    |    |    |    | R | 138 |     |     |     |     |
| A | 60 | 60 | 60 | 60 | 60 | N | 100 | 100 | 100 |   |    | P | 139 | 139 |     |     |     |

FIG. 15A

|   | 1 | 2 | 3 | 4 | 5 |
|---|---|---|---|---|---|
| E | 140 | | | | |
| L | 141 | 141 | 141 | 141 | 141 |
| L | 142 | 142 | 142 | 142 | 142 |
| P | 143 | 143 | | | |
| K | 144 | | | | |
| E | 145 | | | | |
| Y | 146 | 146 | 146 | 146 | |
| D | 148 | | | | |
| F | 149 | 149 | 149 | 149 | 149 |
| F | 151 | 151 | 151 | 151 | 151 |
| Q | 152 | | | | |
| P | 153 | 153 | | | |
| E | 154 | | | | |
| L | 156 | 156 | 156 | 156 | |
| T | 157 | | | | |
| F | 159 | 159 | 159 | 159 | 159 |
| D | 160 | | | | |
| V | 161 | 161 | 161 | 161 | 161 |
| V | 162 | 162 | 162 | 162 | |
| H | 163 | 163 | 163 | 163 | 163 |
| I | 164 | 164 | 164 | 164 | 164 |
| W | 165 | 165 | 165 | 165 | |
| V | 166 | 166 | 166 | 166 | 166 |
| G | 167 | 167 | | | |
| S | 168 | 168 | 168 | | |

|   | 1 | 2 | 3 | 4 | 5 |
|---|---|---|---|---|---|
| M | 169 | 169 | 169 | 169 | 169 |
| A | 170 | 170 | 170 | 170 | 170 |
| N | 171 | 171 | 171 | | |
| R | 172 | | | | |
| F | 173 | 173 | 173 | 173 | 173 |
| S | 174 | 174 | 174 | | |
| D | 175 | | | | |
| T | 176 | 176 | 176 | | |
| N | 177 | 177 | 177 | | |
| E | 179 | | | | |
| V | 180 | 180 | 180 | 180 | |
| T | 181 | | | | |
| L | 183 | 183 | 183 | 183 | 183 |
| A | 184 | 184 | 184 | 184 | 184 |
| M | 185 | 185 | 185 | 185 | |
| Q | 187 | 187 | 187 | | |
| S | 188 | 188 | 188 | | |
| L | 189 | 189 | 189 | 189 | |
| E | 190 | | | | |
| K | 191 | | | | |
| Q | 192 | | | | |
| G | 194 | 194 | | | |
| E | 196 | | | | |
| R | 197 | | | | |
| G | 198 | 198 | | | |

|   | 1 | 2 | 3 | 4 | 5 |
|---|---|---|---|---|---|
| A | 200 | 200 | 200 | 200 | 200 |
| L | 201 | 201 | 201 | 201 | |
| F | 202 | 202 | 202 | 202 | 202 |
| D | 203 | | | | |
| E | 204 | | | | |
| L | 205 | 205 | 205 | 205 | 205 |
| W | 207 | 207 | 207 | 207 | 207 |
| I | 208 | 208 | 208 | 208 | |
| D | 210 | | | | |
| T | 211 | 211 | 211 | | |
| T | 212 | 212 | 212 | | |
| A | 213 | 213 | 213 | 213 | 213 |
| P | 214 | 214 | | | |
| T | 215 | 215 | 215 | | |
| T | 216 | 216 | 216 | | |
| V | 217 | 217 | 217 | 217 | |
| P | 218 | 218 | 218 | 218 | |
| A | 219 | 219 | 219 | 219 | |
| E | 223 | | | | |
| H | 224 | 224 | 224 | | |
| P | 226 | 226 | | | |
| T | 232 | 232 | 232 | | |
| Q | 233 | 233 | 233 | | |
| D | 234 | | | | |
| L | 235 | 235 | 235 | 235 | |

FIG. 15B

Amino acid residue selection in the A. faecalis β-subunit

Number of Residues selection 1: identical and similar
(hydrophobic + charged + polar)                                 416 (75%)
selection 2: identical and similar
(selection 1 minus Asp, Glu, Arg, Lys)                          304 (55%)
selection 3: identical and similar
(selection 2 minus conserved Gly and Pro)                       258 (47%)
selection 4: identical and similar hydrophobic
residues                                                        162 (29%)
selection 5: identical hydrophobic residues                     81 (15%)

The one-letter code preceding the numbers in the row represents the amino acids in the *Alcaligenes faecalis* Type-IIA acylase.

|   | 1 | 2 | 3 | 4 | 5 |   | 1 | 2 | 3 | 4 | 5 |   | 1 | 2 | 3 | 4 | 5 |
|---|---|---|---|---|---|---|---|---|---|---|---|---|---|---|---|---|---|
| S | 266 | 266 | 266 |     |     | G | 306 | 306 |     |     |     | L | 347 | 347 | 347 | 347 | 347 |
| N | 267 | 267 | 267 |     |     | F | 307 | 307 | 307 | 307 |     | N | 348 | 348 | 348 |     |     |
| L | 268 | 268 | 268 | 268 |     | D | 308 |     |     |     |     | P | 349 | 349 | 349 | 349 |     |
| W | 269 | 269 | 269 | 269 | 269 | V | 309 | 309 | 309 | 309 | 309 | S | 350 |     |     |     |     |
| E | 274 |     |     |     |     | V | 310 | 310 | 310 |     |     | R | 351 |     |     |     |     |
| R | 275 |     |     |     |     | G | 311 | 311 |     |     |     | A | 352 | 352 | 352 | 352 |     |
| V | 276 | 276 | 276 | 276 |     | N | 312 | 312 | 312 |     |     | Y | 355 | 355 | 355 | 355 | 355 |
| Q | 277 | 277 | 277 |     |     | T | 313 | 313 | 313 |     |     | N | 358 | 358 | 358 |     |     |
| E | 278 |     |     |     |     | P | 314 | 314 |     |     |     | W | 361 | 361 | 361 | 361 | 361 |
| G | 279 | 279 | 279 | 279 |     | F | 315 | 315 | 315 | 315 | 315 | T | 363 |     |     |     |     |
| S | 280 |     |     |     |     | A | 316 | 316 | 316 | 316 | 316 | M | 364 | 364 | 364 | 364 | 364 |
| T | 281 | 281 | 281 |     |     | Y | 317 | 317 | 317 | 317 | 317 | Q | 366 | 366 | 366 |     |     |
| V | 282 | 282 | 282 | 282 |     | P | 318 | 318 |     |     |     | R | 367 |     |     |     |     |
| L | 283 | 283 | 283 | 283 |     | V | 320 | 320 | 320 | 320 |     | K | 368 |     |     |     |     |
| I | 284 | 284 | 284 | 284 |     | F | 322 | 322 | 322 | 322 | 322 | E | 369 |     |     |     |     |
| N | 285 | 285 | 285 |     |     | G | 323 | 323 |     |     |     | R | 370 |     |     |     |     |
| G | 286 | 286 |     |     |     | T | 324 | 324 | 324 |     |     | I | 371 | 371 | 371 | 371 | 371 |
| P | 287 | 287 |     |     |     | N | 325 | 325 | 325 |     |     | V | 373 | 373 | 373 | 373 | 373 |
| Q | 288 | 288 | 288 |     |     | S | 326 | 326 | 326 |     |     | R | 374 |     |     |     |     |
| F | 289 | 289 | 289 | 289 | 289 | I | 328 | 328 | 328 | 328 | 328 | R | 379 |     |     |     |     |
| G | 290 | 290 |     |     |     | A | 329 | 329 | 329 |     |     | E | 380 |     |     |     |     |
| W | 291 | 291 | 291 | 291 | 291 | W | 330 | 330 | 330 | 330 | 330 | M | 381 | 381 | 381 | 381 |     |
| P | 294 | 294 |     |     |     | G | 331 | 331 |     |     |     | T | 382 | 382 | 382 |     |     |
| A | 295 | 295 | 295 | 295 | 295 | A | 332 | 332 | 332 |     |     | I | 383 | 383 | 383 | 383 |     |
| Y | 296 | 296 | 296 | 296 | 296 | T | 333 | 333 | 333 |     |     | W | 384 | 384 | 384 | 384 | 384 |
| T | 297 | 297 | 297 |     |     | A | 334 | 334 | 334 | 334 | 334 | R | 385 |     |     |     |     |
| Y | 298 | 298 | 298 | 298 | 298 | G | 335 | 335 |     |     |     | T | 386 | 386 | 386 |     |     |
| G | 299 | 299 |     |     |     | D | 338 |     |     |     |     | V | 387 | 387 | 387 | 387 |     |
| I | 300 | 300 | 300 | 300 | 300 | V | 340 | 340 | 340 | 340 | 340 | H | 388 |     |     |     |     |
| G | 301 | 301 |     |     |     | D | 341 |     |     |     |     | G | 389 | 389 |     |     |     |
| L | 302 | 302 | 302 | 302 | 302 | I | 342 | 342 | 342 | 342 | 342 | V | 391 | 391 | 391 | 391 |     |
| H | 303 | 303 | 303 |     |     | Y | 343 | 343 | 343 | 343 |     | M | 392 | 392 | 392 | 392 |     |
| G | 304 | 304 |     |     |     | E | 345 |     |     |     |     | Q | 393 |     |     |     |     |
| A | 305 | 305 | 305 | 305 | 305 | K | 346 |     |     |     |     | D | 395 |     |     |     |     |

FIG. 16A

| | 1 | 2 | 3 | 4 | 5 | | 1 | 2 | 3 | 4 | 5 | | 1 | 2 | 3 | 4 | 5 |
|---|---|---|---|---|---|---|---|---|---|---|---|---|---|---|---|---|---|
| D | 397 | | | | | V | 456 | 456 | 456 | 456 | 456 | Y | 523 | 523 | 523 | 523 | |
| Q | 398 | 398 | 398 | | | S | 457 | 457 | 457 | | | G | 524 | 524 | | | |
| A | 400 | 400 | 400 | | | P | 458 | 458 | 458 | | | D | 525 | | | | |
| A | 401 | 401 | 401 | 401 | 401 | A | 459 | 459 | 459 | 459 | | R | 526 | | | | |
| Y | 402 | 402 | 402 | 402 | 402 | P | 462 | 462 | | | | M | 527 | 527 | 527 | 527 | |
| S | 403 | 403 | 403 | | | Q | 463 | | | | | N | 528 | 528 | 528 | | |
| K | 404 | | | | | R | 464 | | | | | E | 529 | | | | |
| R | 406 | | | | | A | 466 | 466 | 466 | | | L | 530 | 530 | 530 | 530 | |
| S | 407 | 407 | 407 | | | Q | 468 | 468 | 468 | | | S | 532 | | | | |
| W | 408 | 408 | 408 | 408 | 408 | D | 469 | | | | | Q | 535 | | | | |
| G | 410 | 410 | | | | R | 471 | | | | | Q | 536 | | | | |
| E | 412 | | | | | V | 472 | 472 | 472 | 472 | | K | 537 | | | | |
| V | 413 | 413 | 413 | 413 | 413 | P | 473 | 473 | | | | S | 541 | 541 | 541 | | |
| S | 415 | 415 | 415 | | | A | 474 | 474 | 474 | 474 | | V | 542 | 542 | 542 | 542 | |
| L | 416 | 416 | 416 | 416 | 416 | D | 477 | | | | | Q | 543 | | | | |
| L | 417 | 417 | 417 | 417 | 417 | G | 478 | 478 | | | | E | 544 | | | | |
| A | 418 | 418 | 418 | 418 | 418 | S | 479 | | | | | I | 545 | 545 | 545 | 545 | |
| W | 419 | 419 | 419 | 419 | 419 | E | 481 | | | | | W | 546 | 546 | 546 | 546 | 546 |
| N | 421 | 421 | 421 | | | W | 482 | 482 | 482 | 482 | 482 | E | 547 | | | | |
| A | 423 | 423 | 423 | 423 | | G | 484 | 484 | | | | Q | 550 | | | | |
| K | 424 | | | | | I | 485 | 485 | 485 | 485 | | K | 551 | | | | |
| A | 425 | 425 | 425 | 425 | 425 | S | 487 | 487 | 487 | | | A | 552 | 552 | 552 | | |
| R | 426 | | | | | F | 488 | 488 | 488 | 488 | 488 | S | 553 | 553 | 553 | | |
| N | 427 | 427 | 427 | | | D | 489 | | | | | D | 556 | | | | |
| W | 428 | 428 | 428 | 428 | 428 | A | 490 | 490 | 490 | 490 | | V | 557 | 557 | 557 | 557 | |
| T | 429 | 429 | 429 | | | P | 492 | 492 | | | | R | 560 | | | | |
| F | 431 | 431 | 431 | 431 | | K | 493 | | | | | F | 562 | 562 | 562 | 562 | |
| D | 433 | | | | | A | 494 | 494 | 494 | 494 | | P | 564 | 564 | | | |
| Q | 434 | 434 | 434 | | | Y | 495 | 495 | 495 | 495 | 495 | H | 565 | 565 | 565 | | |
| A | 435 | 435 | 435 | 435 | 435 | N | 496 | 496 | 496 | | | E | 567 | | | | |
| S | 436 | 436 | 436 | | | P | 497 | 497 | | | | L | 569 | 569 | 569 | 569 | |
| K | 437 | | | | | Q | 499 | 499 | 499 | | | A | 570 | 570 | 570 | | |
| A | 439 | 439 | 439 | 439 | 439 | G | 500 | 500 | | | | L | 573 | 573 | 573 | 573 | 573 |
| I | 440 | 440 | 440 | 440 | | Y | 501 | 501 | 501 | 501 | 501 | P | 574 | 574 | 574 | | |
| S | 441 | 441 | 441 | | | L | 502 | 502 | 502 | 502 | | D | 576 | | | | |
| I | 442 | 442 | 442 | 442 | 442 | V | 503 | 503 | 503 | 503 | | D | 577 | | | | |
| N | 443 | 443 | 443 | | | N | 504 | 504 | 504 | | | S | 578 | 578 | 578 | | |
| W | 444 | 444 | 444 | 444 | 444 | W | 505 | 505 | 505 | 505 | 505 | S | 579 | | | | |
| Y | 445 | 445 | 445 | 445 | 445 | N | 506 | 506 | 506 | | | K | 580 | | | | |
| Y | 446 | 446 | 446 | 446 | 446 | N | 507 | 507 | 507 | | | A | 582 | 582 | 582 | 582 | |
| A | 447 | 447 | 447 | 447 | 447 | K | 508 | | | | | L | 583 | 583 | 583 | 583 | |
| D | 448 | | | | | P | 509 | 509 | | | | T | 584 | | | | |
| H | 450 | 450 | 450 | | | D | 512 | | | | | L | 586 | 586 | 586 | 586 | 586 |
| G | 451 | 451 | | | | T | 514 | 514 | 514 | | | W | 589 | 589 | 589 | 589 | 589 |
| N | 452 | 452 | 452 | | | T | 516 | 516 | 516 | | | D | 590 | | | | |
| I | 453 | 453 | 453 | 453 | 453 | D | 517 | | | | | G | 591 | 591 | | | |
| G | 454 | 454 | | | | Y | 519 | 519 | 519 | 519 | | E | 593 | | | | |
| Y | 455 | 455 | 455 | 455 | 455 | W | 521 | 521 | 521 | 521 | | D | 595 | | | | |

FIG. 16B

| | 1 | 2 | 3 | 4 | 5 | | 1 | 2 | 3 | 4 | 5 | | 1 | 2 | 3 | 4 | 5 |
|---|---|---|---|---|---|---|---|---|---|---|---|---|---|---|---|---|---|
| Q | 596 | | | | | H | 666 | 666 | 666 | | | Y | 737 | 737 | 737 | 737 | 737 |
| G | 597 | 597 | | | | P | 667 | 667 | | | | Q | 738 | 738 | 738 | | |
| Q | 599 | 599 | 599 | | | P | 669 | 669 | | | | N | 739 | 739 | 739 | | |
| P | 603 | 603 | | | | K | 670 | | | | | R | 740 | | | | |
| A | 604 | 604 | 604 | 604 | | V | 672 | 672 | 672 | 672 | 672 | G | 741 | 741 | | | |
| R | 605 | | | | | N | 673 | | | | | T | 742 | 742 | 742 | | |
| V | 606 | 606 | 606 | 606 | | V | 674 | 674 | 674 | 674 | | E | 743 | | | | |
| L | 607 | 607 | 607 | 607 | 607 | F | 675 | 675 | 675 | 675 | 675 | N | 744 | 744 | 744 | | |
| K | 609 | | | | | G | 676 | 676 | 676 | 676 | | N | 745 | | | | |
| W | 611 | 611 | 611 | 611 | 611 | R | 678 | | | | | V | 747 | 747 | 747 | 747 | |
| L | 612 | 612 | 612 | 612 | 612 | S | 679 | 679 | 679 | | | V | 748 | 748 | 748 | 748 | 748 |
| E | 613 | | | | | S | 680 | | | | | F | 749 | 749 | 749 | 749 | 749 |
| E | 614 | | | | | Q | 681 | 681 | 681 | | | D | 750 | | | | |
| M | 615 | 615 | 615 | 615 | 615 | E | 682 | | | | | A | 751 | 751 | 751 | 751 | |
| K | 617 | | | | | I | 683 | 683 | 683 | 683 | | G | 753 | 753 | 753 | | |
| O | 618 | | | | | M | 684 | 684 | 684 | 684 | | V | 754 | | | | |
| V | 619 | | | | | T | 686 | 686 | 686 | | | E | 755 | | | | |
| L | 620 | 620 | 620 | 620 | | A | 687 | 687 | 687 | 687 | 687 | C | 757 | 757 | 757 | 757 | |
| H | 621 | 621 | 621 | 621 | | L | 688 | 688 | 688 | 688 | 688 | D | 758 | | | | |
| P | 622 | 622 | 622 | 622 | | Q | 689 | | | | | A | 759 | 759 | 759 | 759 | |
| V | 623 | 623 | 623 | 623 | | N | 690 | | | | | M | 760 | 760 | 760 | 760 | |
| V | 624 | 624 | 624 | 624 | 624 | A | 691 | 691 | 691 | | | P | 761 | 761 | 761 | 761 | |
| P | 625 | 625 | | | | R | 694 | | | | | P | 762 | 762 | | | |
| S | 627 | 627 | 627 | | | L | 695 | 695 | 695 | 695 | 695 | G | 763 | 763 | | | |
| Y | 632 | 632 | 632 | 632 | 632 | S | 696 | 696 | 696 | | | Q | 764 | 764 | 764 | | |
| S | 633 | 633 | 633 | | | Q | 697 | | | | | S | 765 | 765 | 765 | | |
| T | 635 | 635 | 635 | | | E | 698 | | | | | G | 766 | 766 | | | |
| G | 636 | 636 | | | | G | 700 | 700 | | | | F | 767 | 767 | 767 | 767 | 767 |
| F | 637 | 637 | 637 | 637 | | Q | 702 | | | | | R | 771 | | | | |
| T | 639 | 639 | 639 | | | H | 703 | 703 | 703 | 703 | | G | 772 | 772 | | | |
| O | 640 | 640 | 640 | | | A | 704 | 704 | 704 | | | H | 777 | 777 | 777 | | |
| Q | 641 | 641 | 641 | | | W | 706 | 706 | 706 | 706 | 706 | Y | 778 | 778 | 778 | 778 | 778 |
| G | 642 | | | | | P | 709 | 709 | | | | E | 779 | | | | |
| P | 643 | 643 | 643 | 643 | | T | 710 | 710 | 710 | | | D | 780 | | | | |
| P | 645 | 645 | 645 | | | V | 712 | 712 | 712 | 712 | | Q | 781 | 781 | 781 | | |
| G | 646 | 646 | | | | R | 714 | | | | | L | 782 | 782 | 782 | 782 | 782 |
| S | 647 | 647 | 647 | | | F | 715 | 715 | 715 | 715 | 715 | K | 783 | | | | |
| I | 648 | 648 | 648 | 648 | | S | 716 | | | | | L | 784 | 784 | 784 | 784 | 784 |
| N | 649 | 649 | 649 | | | K | 718 | | | | | Y | 785 | 785 | 785 | 785 | 785 |
| L | 650 | 650 | 650 | 650 | | N | 719 | 719 | 719 | | | E | 786 | | | | |
| S | 651 | 651 | 651 | | | F | 720 | 720 | 720 | 720 | 720 | N | 787 | 787 | 787 | | |
| M | 652 | 652 | 652 | 652 | | G | 722 | 722 | | | | F | 788 | 788 | 788 | 788 | 788 |
| G | 653 | 653 | | | | T | 723 | | | | | K | 791 | | | | |
| K | 655 | | | | | P | 724 | 724 | | | | T | 792 | 792 | 792 | | |
| V | 656 | 656 | 656 | 656 | | Q | 725 | 725 | 725 | | | M | 793 | 793 | 793 | 793 | |
| L | 657 | 657 | 657 | 657 | 657 | T | 726 | 726 | 726 | | | V | 795 | 795 | 795 | 795 | |
| R | 659 | | | | | P | 728 | 728 | 728 | 728 | | T | 796 | 796 | 796 | | |
| A | 660 | 660 | 660 | 660 | 660 | N | 730 | | | | | D | 799 | | | | |
| L | 661 | 661 | 661 | 661 | | T | 731 | 731 | 731 | | | I | 800 | 800 | 800 | 800 | |
| E | 664 | | | | | T | 735 | 735 | 735 | | | R | 801 | | | | |

FIG. 16C

|   | 1 | 2 | 3 | 4 | 5 |
|---|---|---|---|---|---|
| N | 803 | 803 | 803 | | |
| Q | 805 | | | | |
| S | 806 | 806 | 806 | | |
| S | 807 | 807 | 807 | | |
| T | 808 | | | | |
| M | 809 | 809 | 809 | 809 | |
| L | 810 | 810 | 810 | 810 | 810 |
| I | 812 | 812 | 812 | 812 | |
| Q | 813 | 813 | 813 | | |

FIG. 16D

Amino acid residue selection in the SY-77 α-subunit

| | Number of Residues |
|---|---| selection 1: identical and similar                                    108 (64%)

(hydrophobic + charged +polar)

selection 2: identical and similar                                     87 (51%)

(selection 1 minus positions which can accomodate
a charged residue such as Arg, Lys, His, Glu and
Asp in both Type-IIA and Type-IIB acylases. Only
when Type-IIA acylases show Asp or Glu and Type-
IIB acylases show Arg, Lys or His, the position
is maintained).

selection 3: identical and similar                                     76 (45%)

(selection 2 minus conserved Gly and Pro)

selection 4: identical and similar                                     23 (14%)

(selection 3 minus identical and similar hydrophobic
 residues)

selection 5: identical and similar                                      9 ( 5%)

(selection 4 without positions that can accomodate a
 polar residue in both Type-IIA and Type-IIB acylases)

selection 6: positions in Type-IIB acylase which show
residues that unlike residues at the similar position
in Type-IIA acylases may accomodate the negatively
charged glutaryl side chain.                                                3 ( 2%)

The one-letter code preceding the numbers in the row
represents the amino acids in the SY-77 Type-IIB acylase.

FIG. 17A

| | 1 | 2 | 3 | 4 | 5 | 6 |
|---|---|---|---|---|---|---|
| P | 31 | 31 | 31 | | | |
| T | 32 | 32 | 32 | 32 | 32 | |
| S | 33 | 33 | 33 | 33 | 33 | |
| T | 34 | 34 | 34 | 34 | 34 | |
| Q | 36 | | | | | |
| A | 37 | 37 | 37 | | | |
| A | 40 | 40 | 40 | | | |
| A | 41 | 41 | 41 | | | |
| Y | 42 | 42 | 42 | | | |
| P | 44 | 44 | | | | |
| S | 46 | 46 | 46 | 46 | 46 | |
| E | 48 | 48 | 48 | 48 | | |
| I | 49 | 49 | 49 | | | |
| D | 52 | | | | | |
| G | 53 | 53 | | | | |
| Y | 54 | 54 | 54 | | | |
| G | 55 | 55 | | | | |
| V | 56 | 56 | 56 | | | |
| P | 57 | 57 | | | | |
| H | 58 | | | | | |
| I | 59 | 59 | 59 | | | |
| G | 61 | 61 | 61 | | | |
| V | 62 | 62 | 62 | 62 | | |
| P | 65 | 65 | 65 | | | |
| S | 66 | | | | | |
| A | 67 | 67 | 67 | | | |
| F | 68 | 68 | 68 | | | |
| Y | 69 | 69 | 69 | 69 | | |
| G | 70 | 70 | 70 | | | |
| Y | 71 | 71 | 71 | | | |
| G | 72 | 72 | | | | |
| W | 73 | 73 | 73 | | | |
| A | 74 | 74 | 74 | | | |
| Q | 75 | 75 | 75 | 75 | | |
| R | 77 | | | | | |
| H | 79 | 79 | 79 | 79 | | |
| D | 81 | | | | | |
| I | 83 | 83 | 83 | | | |
| R | 85 | | | | | |
| E | 89 | | | | | |
| A | 90 | 90 | 90 | | | |
| G | 92 | 92 | | | | |
| K | 93 | 93 | 93 | 93 | 93 | 93 |
| G | 94 | 94 | 94 | | | |
| A | 95 | 95 | 95 | | | |
| E | 96 | | | | | |

| | 1 | 2 | 3 | 4 | 5 | 6 |
|---|---|---|---|---|---|---|
| Y | 97 | 97 | 97 | | | |
| W | 98 | 98 | 98 | | | |
| G | 99 | 99 | | | | |
| P | 100 | 100 | 100 | | | |
| D | 101 | | | | | |
| Y | 102 | 102 | 102 | | | |
| Q | 104 | | | | | |
| T | 105 | 105 | 105 | 105 | 105 | |
| T | 106 | | | | | |
| V | 107 | | | | | |
| W | 108 | 108 | 108 | | | |
| L | 109 | 109 | 109 | | | |
| T | 111 | | | | | |
| G | 113 | 113 | | | | |
| V | 114 | 114 | 114 | | | |
| E | 116 | | | | | |
| A | 118 | 118 | 118 | | | |
| Q | 119 | 119 | 119 | 119 | | |
| Q | 120 | | | | | |
| Y | 122 | 122 | 122 | | | |
| S | 126 | 126 | 126 | 126 | | |
| P | 127 | 127 | 127 | | | |
| D | 128 | | | | | |
| F | 129 | 129 | 129 | 129 | 129 | 129 |
| R | 130 | | | | | |
| L | 133 | 133 | 133 | | | |
| D | 134 | | | | | |
| A | 135 | 135 | 135 | | | |
| F | 136 | 136 | 136 | | | |
| A | 137 | 137 | 137 | | | |
| A | 138 | 138 | 138 | 138 | 138 | 138 |
| G | 139 | 139 | | | | |
| I | 140 | 140 | 140 | | | |
| N | 141 | 141 | 141 | 141 | | |
| A | 142 | 142 | 142 | | | |
| Y | 143 | 143 | 143 | | | |
| A | 144 | 144 | 144 | | | |
| Q | 145 | 145 | 145 | 145 | | |
| Q | 146 | 146 | 146 | 146 | | |
| P | 148 | 148 | | | | |
| I | 151 | 151 | 151 | | | |
| S | 152 | | | | | |
| V | 155 | 155 | 155 | | | |
| V | 158 | 158 | 158 | | | |
| P | 160 | 160 | | | | |
| S | 162 | 162 | 162 | 162 | | |

| | 1 | 2 | 3 | 4 | 5 | 6 |
|---|---|---|---|---|---|---|
| V | 166 | 166 | 166 | | | |
| A | 168 | 168 | 168 | 168 | | |
| A | 170 | 170 | 170 | | | |
| L | 177 | 177 | 177 | | | |
| Y | 178 | 178 | 178 | | | |
| V | 179 | 179 | 179 | | | |
| A | 180 | 180 | 180 | | | |
| S | 181 | 181 | 181 | 181 | | |
| P | 182 | 182 | 182 | | | |
| T | 185 | 185 | 185 | 185 | | |
| L | 186 | 186 | 186 | 186 | 186 | |
| E | 188 | | | | | |
| P | 191 | 191 | 191 | | | |
| L | 194 | 194 | 194 | | | |
| A | 195 | 195 | 195 | | | |
| G | 198 | 198 | 198 | | | |

FIG. 17B

Amino acid residue selection in the SY-77 β-subunit

|  | Number of Residues |
|---|---|
| selection 1: identical and similar | 323 (62%) |
| (hydrophobic + charged +polar) | |
| selection 2: identical and similar | 258 (50%) |

(selection 1 minus positions which can accomodate a charged residue such as Arg, Lys, His, Glu and Asp in both Type-IIA and Type-IIB acylases. Only when Type-IIA acylases show Asp or Glu and Type-IIB acylases show Arg, Lys or His, the position is maintained.)

selection 3: identical and similar  225 (43%)

(selection 2 minus conserved Gly and Pro)

selection 4: identical and similar  80 (15%)

(selection 3 minus identical and similar hydrophobic residues)

selection 5: identical and similar  35 ( 7%)

(selection 4 without positions that can accomodate a polar residue in both Type-IIA and Type-IIB acylases)

selection 6: positions in Type-IIB acylase which show residues that unlike residues at the similar position in Type-IIA acylases may accomodate the negatively charged glutaryl side chain.  9 ( 4%)

The one-letter code preceding the numbers in the row represents the amino acids in the SY-77 Type-IIB acylase.

FIG. 18A

|   | 1 | 2 | 3 | 4 | 5 | 6 |   | 1 | 2 | 3 | 4 | 5 | 6 |   | 1 | 2 | 3 | 4 | 5 | 6 |
|---|---|---|---|---|---|---|---|---|---|---|---|---|---|---|---|---|---|---|---|---|
| S | 199 | 199 | 199 | 199 |   |   | A | 257 | 257 | 257 |   |   |   | V | 339 | 339 | 339 | 339 |   |   |
| N | 200 | 200 | 200 | 200 |   |   | N | 259 | 259 | 259 | 259 |   |   | A | 340 | 340 | 340 |   |   |   |
| S | 201 | 201 | 201 | 201 | 201 |   | R | 261 |   |   |   |   |   | L | 342 |   |   |   |   |   |
| W | 202 | 202 | 202 |   |   |   | M | 262 | 262 | 262 |   |   |   | D | 343 |   |   |   |   |   |
| A | 203 | 203 | 203 |   |   |   | G | 263 | 263 | 263 |   |   |   | R | 344 | 344 | 344 | 344 | 344 | 344 |
| V | 204 | 204 | 204 |   |   |   | I | 264 | 264 | 264 |   |   |   | P | 179 | 179 | 179 |   |   |   |
| A | 205 | 205 | 205 |   |   |   | T | 265 | 265 | 265 | 265 | 265 |   | A | 345 | 345 | 345 |   |   |   |
| P | 206 | 206 |   |   |   |   | T | 267 | 267 | 267 | 267 |   |   | G | 346 | 346 | 346 | 346 |   |   |
| G | 207 | 207 |   |   |   |   | M | 271 | 271 | 271 |   |   |   | M | 347 | 347 | 347 |   |   |   |
| K | 208 |   |   |   |   |   | T | 275 |   |   |   |   |   | T | 356 | 356 | 356 | 356 | 356 |   |
| T | 209 | 209 | 209 | 209 | 209 |   | Y | 277 | 277 | 277 |   |   |   | A | 357 | 357 | 357 | 357 | 357 |   |
| A | 210 | 210 | 210 |   |   |   | L | 281 | 281 | 281 |   |   |   | S | 359 | 359 | 359 | 359 |   |   |
| N | 211 | 211 | 211 | 211 | 211 | 211 | Q | 282 |   |   |   |   |   | F | 360 | 360 | 360 |   |   |   |
| G | 212 | 212 |   |   |   |   | D | 283 |   |   |   |   |   | D | 362 |   |   |   |   |   |
| N | 213 |   |   |   |   |   | G | 284 | 284 |   |   |   |   | Y | 363 | 363 | 363 |   |   |   |
| A | 214 | 214 | 214 |   |   |   | L | 287 |   |   |   |   |   | A | 366 | 366 | 366 |   |   |   |
| L | 215 | 215 | 215 |   |   |   | G | 290 | 290 |   |   |   |   | M | 370 | 370 | 370 |   |   |   |
| L | 216 | 216 | 216 |   |   |   | Q | 291 | 291 | 291 | 291 |   |   | V | 372 | 372 | 372 |   |   |   |
| L | 217 | 217 | 217 |   |   |   | F | 295 | 295 | 295 |   |   |   | P | 373 | 373 | 373 |   |   |   |
| N | 219 |   |   |   |   |   | E | 296 |   |   |   |   |   | T | 374 |   |   |   |   |   |
| P | 220 | 220 |   |   |   |   | P | 298 | 298 |   |   |   |   | N | 376 | 376 | 376 |   |   |   |
| H | 221 | 221 | 221 | 221 | 221 | 221 | A | 300 | 300 | 300 |   |   |   | I | 377 | 377 | 377 |   |   |   |
| S | 223 | 223 | 223 | 223 | 223 |   | R | 303 |   |   |   |   |   | V | 378 | 378 | 378 |   |   |   |
| W | 224 | 224 | 224 |   |   |   | R | 305 |   |   |   |   |   | Y | 379 | 379 | 379 |   |   |   |
| T | 226 |   |   |   |   |   | A | 307 | 307 | 307 |   |   |   | A | 380 | 380 | 380 |   |   |   |
| U | 231 | 231 | 231 |   |   |   | T | 310 | 310 | 310 | 310 |   |   | D | 381 |   |   |   |   |   |
| Y | 232 | 232 | 232 |   |   |   | T | 311 | 311 | 311 | 311 |   |   | G | 384 | 384 |   |   |   |   |
| E | 233 |   |   |   |   |   | V | 312 | 312 | 312 |   |   |   | T | 385 | 385 | 385 | 385 |   |   |
| H | 235 | 235 | 235 | 235 | 235 | 235 | D | 313 |   |   |   |   |   | I | 386 | 386 | 386 |   |   |   |
| L | 236 | 236 | 236 |   |   |   | K | 314 |   |   |   |   |   | F | 390 | 390 | 390 |   |   |   |
| V | 237 | 237 | 237 |   |   |   | E | 317 |   |   |   |   |   | N | 391 | 391 | 391 |   |   |   |
| T | 238 | 238 | 238 |   |   |   | I | 318 | 318 | 318 |   |   |   | G | 392 | 392 | 392 |   |   |   |
| D | 240 |   |   |   |   |   | R | 319 |   |   |   |   |   | A | 394 | 394 | 394 |   |   |   |
| F | 241 | 241 | 241 |   |   |   | S | 320 | 320 | 320 | 320 |   |   | P | 395 | 395 |   |   |   |   |
| E | 242 |   |   |   |   |   | H | 323 |   |   |   |   |   | K | 396 |   |   |   |   |   |
| I | 243 | 243 | 243 |   |   |   | G | 324 | 324 |   |   |   |   | R | 397 |   |   |   |   |   |
| Y | 244 | 244 | 244 |   |   |   | P | 325 | 325 |   |   |   |   | D | 401 |   |   |   |   |   |
| G | 245 | 245 |   |   |   |   | V | 326 | 326 | 326 |   |   |   | A | 403 | 403 | 403 |   |   |   |
| H | 246 | 246 | 246 |   |   |   | F | 327 | 327 | 327 |   |   |   | F | 404 | 404 | 404 |   |   |   |
| T | 247 | 247 | 247 | 247 |   |   | A | 330 | 330 | 330 |   |   |   | W | 405 | 405 | 405 |   |   |   |
| G | 250 | 250 |   |   |   |   | T | 333 | 333 | 333 | 333 |   |   | V | 409 | 409 | 409 |   |   |   |
| L | 251 | 251 | 251 |   |   |   | A | 334 | 334 | 334 |   |   |   | P | 410 | 410 |   |   |   |   |
| P | 252 | 252 |   |   |   |   | V | 335 | 335 | 335 |   |   |   | G | 411 | 411 |   |   |   |   |
| V | 253 | 253 | 253 |   |   |   | A | 336 | 336 | 336 |   |   |   | S | 413 | 413 | 413 | 413 |   |   |
| R | 255 | 255 | 255 | 255 | 255 | 255 | V | 337 | 337 | 337 |   |   |   | S | 414 | 414 | 414 | 414 | 414 |   |
| F | 256 | 256 | 256 |   |   |   | R | 338 |   |   |   |   |   | R | 415 |   |   |   |   |   |

FIG. 18B

| | 1 | 2 | 3 | 4 | 5 | 6 | | 1 | 2 | 3 | 4 | 5 | 6 | | 1 | 2 | 3 | 4 | 5 | 6 |
|---|---|---|---|---|---|---|---|---|---|---|---|---|---|---|---|---|---|---|---|---|
| W | 418 | 418 | 418 | | | | M | 492 | 492 | 492 | | | | A | 561 | 561 | 561 | | | |
| T | 419 | | | | | | A | 493 | 493 | 493 | | | | F | 563 | 563 | 563 | | | |
| P | 423 | 423 | | | | | L | 494 | 494 | 494 | | | | A | 564 | 564 | 564 | | | |
| D | 425 | | | | | | S | 497 | 497 | 497 | | | | T | 565 | 565 | 565 | 565 | | |
| L | 427 | 427 | 427 | | | | H | 498 | 498 | 498 | 498 | 498 | 498 | P | 566 | 566 | | | | |
| P | 428 | 428 | | | | | A | 500 | 500 | 500 | | | | T | 567 | 567 | 567 | 567 | 567 | |
| R | 429 | | | | | | V | 501 | 501 | 501 | | | | L | 569 | 569 | 569 | | | |
| V | 430 | 430 | 430 | | | | A | 503 | 503 | 503 | | | | D | 570 | | | | | |
| N | 432 | | | | | | D | 504 | | | | | | V | 573 | 573 | 573 | | | |
| P | 433 | 433 | | | | | T | 506 | 506 | 506 | | | | S | 574 | 574 | 574 | 574 | 574 | |
| P | 434 | 434 | | | | | L | 507 | 507 | 507 | | | | G | 578 | 578 | | | | |
| G | 435 | 435 | | | | | P | 508 | 508 | | | | | V | 579 | 579 | 579 | | | |
| G | 436 | 436 | | | | | D | 509 | | | | | | R | 580 | 580 | 580 | 580 | 580 | |
| F | 437 | 437 | 437 | | | | I | 511 | 511 | 511 | | | | K | 583 | | | | | |
| V | 438 | 438 | 438 | | | | A | 514 | 514 | 514 | 514 | | | A | 584 | 584 | 584 | | | |
| N | 440 | 440 | 440 | 440 | | | L | 515 | 515 | 515 | | | | A | 585 | 585 | 585 | | | |
| S | 441 | 441 | 441 | 441 | 441 | | I | 516 | 516 | 516 | | | | V | 586 | 586 | 586 | 586 | 586 | |
| N | 442 | 442 | 442 | 442 | | | D | 519 | | | | | | D | 587 | | | | | |
| D | 443 | | | | | | A | 524 | 524 | 524 | | | | L | 589 | 589 | 589 | | | |
| P | 445 | 445 | 445 | | | | A | 525 | 525 | 525 | | | | R | 590 | 590 | 590 | 590 | | |
| T | 446 | 446 | 446 | 446 | | | R | 526 | 526 | 526 | 526 | | | T | 591 | 591 | 591 | 591 | 591 | |
| T | 447 | 447 | 447 | 447 | | | L | 527 | 527 | 527 | | | | A | 592 | 592 | 592 | | | |
| V | 452 | 452 | 452 | | | | L | 528 | 528 | 528 | | | | N | 595 | 595 | 595 | 595 | 595 | |
| T | 453 | | | | | | A | 530 | 530 | 530 | | | | L | 596 | 596 | 596 | | | |
| Y | 454 | 454 | 454 | | | | W | 531 | 531 | 531 | | | | T | 597 | 597 | 597 | 597 | 597 | |
| P | 456 | 456 | 456 | | | | D | 532 | | | | | | R | 599 | | | | | |
| K | 457 | 457 | 457 | 457 | 457 | | R | 533 | 533 | 533 | 533 | 533 | 533 | Y | 601 | 601 | 601 | | | |
| D | 458 | | | | | | F | 535 | 535 | 535 | | | | G | 602 | 602 | | | | |
| P | 460 | 460 | | | | | T | 536 | 536 | 536 | 536 | | | D | 605 | | | | | |
| S | 461 | 461 | 461 | 461 | 461 | | S | 537 | 537 | 537 | | | | R | 606 | | | | | |
| Y | 462 | 462 | 462 | | | | S | 539 | 539 | 539 | 539 | | | P | 607 | 607 | | | | |
| A | 464 | 464 | 464 | | | | R | 540 | 540 | 540 | 540 | 540 | | D | 610 | | | | | |
| Q | 466 | 466 | 466 | 466 | 466 | | A | 541 | 541 | 541 | | | | S | 612 | 612 | 612 | 612 | 612 | |
| H | 469 | | | | | | A | 542 | 542 | 542 | 542 | | | I | 615 | 615 | 615 | | | |
| S | 470 | 470 | 470 | 470 | | | L | 544 | 544 | 544 | | | | V | 619 | 619 | 619 | | | |
| L | 471 | 471 | 471 | | | | E | 546 | 546 | 546 | 546 | 546 | | V | 621 | 621 | 621 | | | |
| A | 473 | 473 | 473 | | | | W | 548 | 548 | 548 | | | | P | 622 | 622 | 622 | | | |
| S | 476 | 476 | 476 | 476 | | | A | 549 | 549 | 549 | | | | G | 623 | 623 | 623 | | | |
| V | 477 | 477 | 477 | | | | R | 550 | 550 | 550 | 550 | 550 | 550 | N | 629 | 629 | 629 | 629 | | |
| R | 478 | | | | | | F | 551 | 551 | 551 | | | | S | 632 | 632 | 632 | 632 | | |
| M | 480 | 480 | 480 | | | | L | 552 | 552 | 552 | | | | R | 634 | 634 | 634 | 634 | 634 | 634 |
| S | 481 | 481 | 481 | 481 | 481 | | A | 553 | 553 | 553 | | | | V | 635 | 635 | 635 | | | |
| T | 487 | 487 | 487 | 487 | | | G | 554 | 554 | | | | | G | 636 | 636 | 636 | | | |
| L | 488 | 488 | 488 | | | | H | 556 | 556 | 556 | 556 | | | T | 637 | 637 | 637 | 637 | 637 | |
| E | 489 | | | | | | G | 559 | 559 | | | | | T | 638 | 638 | 638 | 638 | | |
| | | | | | | | Q | 560 | 560 | 560 | 560 | | | S | 639 | | | | | |

FIG. 18C

|   | 1 | 2 | 3 | 4 | 5 | 6 |
|---|---|---|---|---|---|---|
| D | 640 | | | | | |
| P | 641 | 641 | 641 | | | |
| N | 644 | | | | | |
| V | 646 | 646 | 646 | | | |
| T | 648 | 648 | 648 | 648 | | |
| P | 649 | 649 | | | | |
| V | 650 | 650 | 650 | 650 | | |
| G | 652 | 652 | | | | |
| E | 653 | | | | | |
| T | 654 | 654 | 654 | 654 | | |
| W | 655 | 655 | 655 | | | |
| V | 656 | 656 | 656 | | | |
| A | 657 | 657 | 657 | | | |
| H | 658 | 658 | 658 | | | |
| E | 660 | | | | | |
| F | 661 | 661 | 661 | | | |
| S | 662 | | | | | |
| T | 663 | 663 | 663 | 663 | 663 | |
| R | 666 | 666 | 666 | 666 | 666 | |

|   | 1 | 2 | 3 | 4 | 5 | 6 |
|---|---|---|---|---|---|---|
| Y | 668 | 668 | 668 | | | |
| L | 670 | 670 | 670 | | | |
| M | 671 | 671 | 671 | | | |
| G | 674 | 674 | | | | |
| S | 676 | 676 | 676 | 676 | | |
| P | 679 | 679 | | | | |
| G | 680 | 680 | 680 | | | |
| T | 681 | 681 | 681 | 681 | | |
| T | 682 | 682 | 682 | 682 | | |
| H | 683 | | | | | |
| Y | 684 | 684 | 684 | | | |
| S | 685 | 685 | 685 | 685 | | |
| D | 686 | | | | | |
| Q | 687 | 687 | 687 | 687 | | |
| E | 689 | | | | | |
| V | 691 | | | | | |
| R | 693 | 693 | 693 | 693 | | |
| F | 696 | 696 | 696 | | | |
| L | 700 | 700 | 700 | | | |

|   | 1 | 2 | 3 | 4 | 5 | 6 |
|---|---|---|---|---|---|---|
| L | 701 | 701 | 701 | | | |
| R | 703 | | | | | |
| Q | 705 | | | | | |
| A | 708 | | | | | |
| A | 709 | 709 | 709 | 709 | | |
| V | 710 | 710 | 710 | 710 | | |
| Q | 711 | 711 | 711 | 711 | | |
| E | 712 | | | | | |
| F | 716 | 716 | 716 | | | |
| F | 718 | 718 | 718 | | | |

MUTATED β-LACTAM ACYLASE GENES

CROSS-REFERENCE TO RELATED APPLICATIONS

This application is a continuation of U.S. application Ser. No. 07/731,157 filed May 9, 1991 now U.S. Pat. No. 5,457,032, issued Oct. 10, 1995, which disclosure is hereby incorporated by reference. Additionally, this application claims the priority of European Patent Application No. 90200962.0 filed in the Netherlands on Apr. 18, 1990.

FIELD OF THE INVENTION

The present invention relates to mutations of genes encoding acylases, resulting in alterations in the substrate specificity of acylase enzymes. Some of these mutant enzymes exhibit catalytic properties which make them particularly suitable for the deacylation/acylation of β-lactam derivatives. Among those is a preferred group which is designed for a one-step conversion of Cephalosporin C and derivatives to 7-aminocephalosporanic acid and derivatives.

BACKGROUND OF THE INVENTION

The basic antibiotics of the P-lactam type are principally obtained by fermentation. Fungi of the genus Penicillium and Cephalosporium (Acremonium) are used for the production of raw material for β-lactam antibiotics as Penicillin G, Penicillin V and Cephalosporin C. These fermentation products, also referred to as PenG, PenV and CefC, respectively, are the starting materials for nearly all currently marketed penicillins and cephalosporins. The side-chains of these compounds, phenylacetyl, phenoxyacetyl and aminoadipyl, respectively, are removed by cleavage of an amide linkage (deacylation), resulting in 6-aminopenicillanic acid (6-APA) in case of the two penicillin molecules and 7-aminocephalosporanic acid (7-ACA) in case of the cephalosporin. The particular enzymes which accomplish these conversions are referred to herein as "acylases" or "amidases". These denominations as used in this specification have the same meaning.

Also, the conversion of Cephalosporin G to 7-amino 3-deacetoxycephalosporanic acid (7-ADCA) is mentioned. However, Cephalosporin G (CefG) is not a fermentation product but is usually produced chemically from Penicillin G. The basic structures of the various penicillins and cephalosporins discussed above are shown in FIG. 1.

Synthetic manipulation to produce the various penicillins and cephalosporins of choice basically starts from 6-APA, 7-ACA and 7-ADCA, respectively.

The conversion of Penicillin G and Penicillin V to 6-APA may be performed both chemically and enzymatically. The classical way is the chemical cleavage, but enzymatic processes are preferred nowadays (for review, see Lowe [1]). Costs and environmental considerations are arguments in favour of an enzymatic process.

The cleavage of the CefC side-chain to 7-ACA is usually carried out chemically, according to the so-called iminohalide process. However, this process has serious disadvantages, since it is complex, requiring inter alia multiple steps, extremely low temperatures and expensive reagents.

The conversion of β-lactam intermediates to the desired semi-synthetic antibiotics may also be performed chemically and enzymatically, the enzymatic route being basically preferred if a suitable enzyme is available. Penicillin acylases are such enzymes in a number of cases. The enzymatic conversion takes advantage of the fact that any enzymatic reaction is reversible, if the correct conditions are applied (Abbott B. J. [2]).

Various types of microorganisms have been proposed in the literature as acylase producing strains useful for the deacylation of β-lactam derivatives obtained by fermentation and/or the acylation of 6-APA and 7-ACA to semi-synthetic β-lactam antibiotics of choice. Examples of such acylase producing microorganisms are certain strains of the species *Escherichia coli, Kluyvera citrophila, Proteus rettgeri*, Pseudomonas sp., *Alcaligenes faecalis, Bacillus megaterium, Bacillus sphaericus*, and *Arthrobacter viscosus*.

According to the literature several types of acylases may be envisaged, based on their molecular structure and substrate specificity (Vandamme E. J. [3]).

Type-I acylases are specific for Penicillin V. These enzymes are composed of four identical subunits, each having a molecular weight of 35 kDa. A complete nucleotide sequence of the cloned gene from *Bacillus sphaericus* has been reported (Ollson A. [4]).

Type-II acylases all share a common molecular structure: these enzymes are heterodimers composed of a small subunit ($\alpha$; 20–25 kDa) and a large subunit ($\beta$; 60–65 kDa). With respect to the substrate specificity, Type-II acylases may be further divided into two groups:

Type-IIA acylases are very specific for Penicillin G. In general, they are not so much specific for the moiety adjacent to the nitrogen atom of the amide group (this might be a cephem group, a penem group, an amino acid, etc.), but the substrate specificity resides in the acyl moiety of the substrate. This acyl moiety must be very hydrophobic and is preferably benzyl or (short) alkyl. Examples of substrates which are not hydrolyzed by Type-IIA acylases are those with dicarboxylic acids as acyl moiety: succinyl, glutaryl, adipyl and also aminoadipyl, the side-chain of CefC. Examples of Type-IIA acylases are the enzymes from *Escherichia coli, Kluyvera citrophila, Proteus rettgeri* and *Alcaligenes faecalis*. Type-IIB acylases have been reported to be capable of hydrolyzing cephalosporins (including the desacetoxy-derivative) with succinyl, glutaryl and adipyl as an acyl moiety and even in one case CefC to a very limited degree (Shibuya Y. [5]; Matsuda A. [6]). So far these acylases have only been found in Pseudomonas species, and in certain strains of *Bacillus megaterium* and Arthrobacter viscosus.

The literature relates mainly to penicillin acylases. The synthetic potential of penicillin acylases, however, is limited due to the specificity of the enzyme. In more recent years also publications relating to Cephalosporin C acylases have appeared, but the activity of the reported enzymes was relatively low. No commercial enzymatic process for the conversion of Cephalosporin C to 7-ACA is available up to now, despite intensive efforts to find a suitable enzyme (cf. Walton R. B. [7]).

There is, therefore, a substantial interest in developing acylase enzymes which are highly efficient in deacylation/acylation reactions to produce desired chemical entities. Of particular interest are the enzymatic deacylation of β-lactams and especially PenG, PenV and CefC, and derivatives thereof, to 6-APA and 7-ACA and derivatives, respectively, and the acylation of the latter compounds to produce semi-synthetic pencillins and cephalosporins of interest. It is of major importance in this connection to dispose of an efficient acylase enzyme which is capable of catalyzing the conversion of CefC (and derivatives) to 7-ACA (and derivatives).

The invention aims to provide such efficient enzymes.

RELEVANT PRIOR ART

Mahajan [8] gives a review of various penicillin acylases and distinguishes PenG and PenV specific acylases.

European Patent Application EP-A-0283218 discloses an enzymatic one step conversion of CefC and derivatives to 7-ACA and derivatives, using an enzyme derived from *Arthrobacter viscosus* strain ATCC 53594.

EP-A-0322032 discloses the same enzymatic one step conversion, using an enzyme derived from *Bacillus megaterium* strain ATCC 53667.

U.S. Pat. No. 4,774,179 discloses basically the same conversion, using Pseudomonas sp. SE-83 or SE-495, or material obtained from these microorganisms by subjecting them to chemical and/or physical treatment.

As already stated before, the low activities of these enzymes stands in the way of a commercial use up till now.

The use of recombinant DNA methods has enabled an increase of the production levels of commercially used penicillin acylases (Mayer [9]) and has enlarged the insight into the processing of these enzymes (Schumacher [10]). The penicillin acylase of *E. coli* was found to be produced as a large precursor protein, which was further processed into the periplasmic mature protein constituting a small (α) and a large (β) subunit. Cloning and sequencing of the *Kluyvera citrophila* acylase gene has revealed a close homology with the *E. coli* acylase gene (Barbero [11]). Also for *Proteus rettgeri* penicillin G acylase a small and a large subunit has been described (Daumy [12]).

Williams [33] describes substrate specificity modifications of the PenG acylase of *E. coli* ATCC 9637 occurring in a natural variant. The method was based on replacement subcloning of regions in the wild-type gene with equivalent regions of the gene of a natural mutant.

Forney [34, 35] describes the selection of amidases with novel substrate specificities from penicillin amidase of *E. coli* and the alteration of catalytic efficiency of such a penicillin amidase (of *E. coli* ATCC 11105) by propagation of a recombinant plasmid in a *E. coli* strain with a high mutation frequency. D-(-)-α-aminophenylacetyl-(L)-leucine was used as a substrate analog of ampicillin and cephalexin. It was found possible to alter the substrate specificity of penicillin amidase and obtain enzymes that, at low pH, hydrolyze amides with α-aminophenylacetyl moieties more rapidly.

These publications neither teach nor suggest the instant invention.

SUMMARY OF THE INVENTION

The present invention relates to mutations of acylase genes, some of which result in alterations in the substrate specificity of acylase enzymes. Mutations are created at specific nucleotides of the acylase genes, and, in various specific embodiments, the mutant enzymes show altered biochemical properties, which may result in, but are not limited to, increased specificity towards the deacylation of certain β-lactam antibiotics.

In a preferred embodiment new mutant enzymes are provided which are particularly suitable for a one-step conversion of CefC and derivatives to 7-ACA and derivatives.

In another preferred embodiment new mutant enzymes are provided which are particularly suitable for the acylation of 6-APA and 7-A(D)CA, resulting in the production of desired penicillin and cephalosporin derivatives.

In an embodiment of the invention genes encoding known Type-IIA or Type-IIB acylases, for example PenG acylases from *Escherichia coli*, *Kluyvera citrophila*, *Alcaligenes faecalis* or any other organism producing such enzymes, and glutaryl-Cef acylases from Pseudomonas SE-83 AcyII, Pseudomonas SY-77 or any other organism producing such enzymes, are mutated in such a way that the enzymes obtain an altered specifity for their substrates.

These and other embodiments will hereinafter be outlined in further detail.

BRIEF DESCRIPTION OF THE DRAWINGS

FIG. 5A–5F: nucleotide sequence (SEQ. ID NO:3) and derived amino acid sequence (SEQ. ID NO:4) of the penicillin acylase gene of *Alcaligenes faecalis*. Amino acids are indicated in the 1-letter code.

FIG. 13A–13D: nucleotide sequence (SEQ. ID NO:4) and derived amino acid sequence (SEQ. ID NO:2) of the complete Pseudomonas SY-77 glutaryl-Cef acylase gene.

FIG. 14A–14E: alignment of Type-II acylases from *E. coli* (e.col) (SEQ. ID NO:5), *Kluvvera citrophila* (K.cit) (SEQ. ID NO:7), *Alcaligenes faecalis* (a.fae) (SEQ. ID NO:4), Pseudomonas SE-83 AcyII (AcyII) (SEQ. ID NO:7) and Pseudomonas SY-77 (SY-77). An asterix denotes that the sequence contains the same amino acid at that position as the sequence from the *E. coli* acylase.

FIG. 15A–15B: region selection in the *Alcaligenes faecalis* α-subunit.

FIG. 16A–16D: region selection in the *Alcaligenes faecalis* β-subunit.

FIG. 17A–17B: amino acid residue selection in the SY-77 α-subunit.

FIG. 18A–18D: amino acid residue selection in the SY-77 β-subunit.

DETAILED DESCRIPTION OF THE INVENTION

Figure 1A:
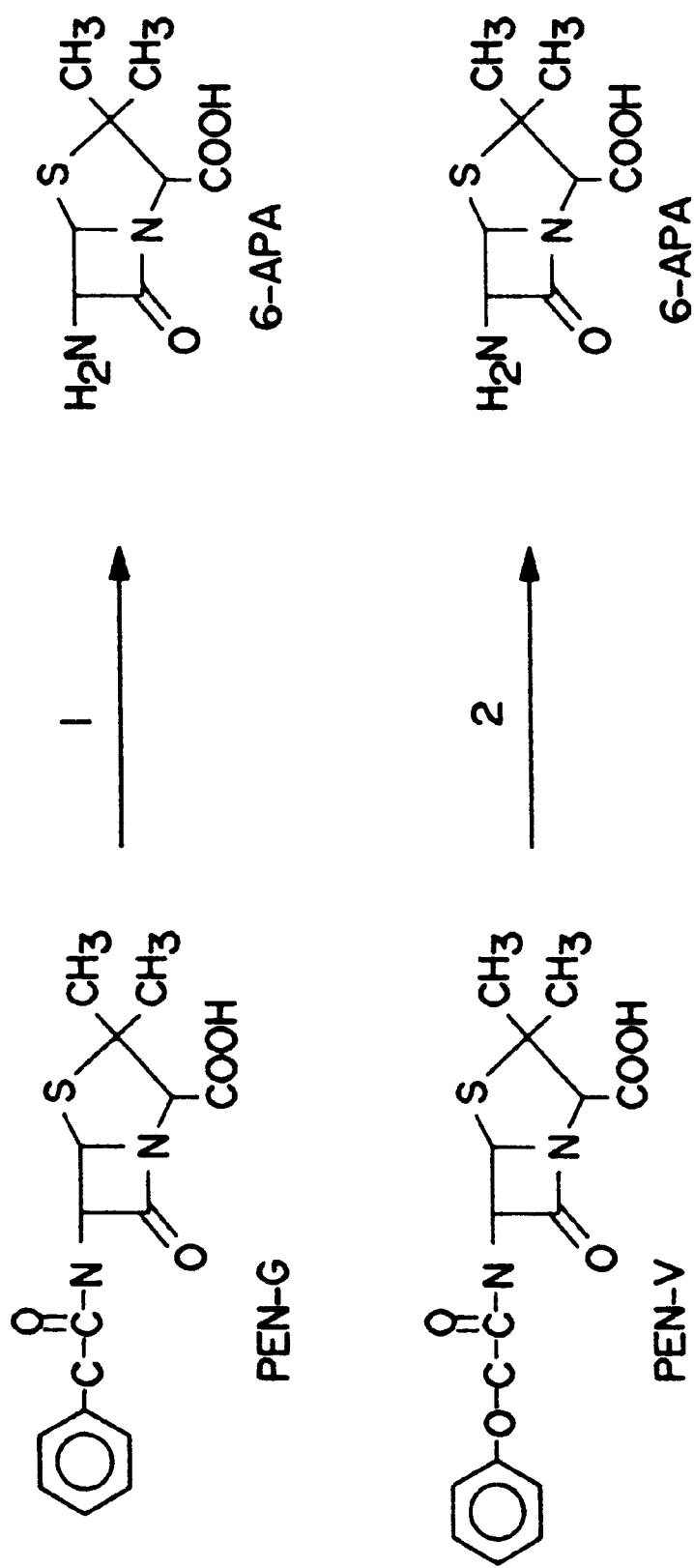
FIG 1A–1B: reaction schemes of certain β-lactam conversions. Reaction 1 is the deacylation of PenG resulting in 6-APA and phenylacetic acid. Reaction 2 reflects the deacylation of PenV resulting in 6-APA and phenoxyacetic acid. Reaction 3 is the deacylation of CefC into 7-ACA and (β-)aminoadipic acid. Reaction 4 reflects the deacylation of CefG into 7-ADCA and phenylacetic acid.

The present invention uses protein engineering as a tool to develop acylases with an altered substrate specificity. The invention is based on the finding that the genes encoding various (known) acylases show a significant degree of homology at certain regions. A comparative analysis was made which has indicated that certain mutations may alter the biochemical properties of the acylases. According to the method which will be outlined below a number of potential mutation sites will become apparent.

It has been observed that the tertiary structures in homologous proteins are much more conserved in evolution than the primary structures and considerably more than the DNA-sequences. This is for example illustrated by the globin-family (Dickerson [13]). The globin fold is encoded by many different amino acid sequences, some differing from others in as many as 86% (130 out of 150 residues). Nevertheless, their closely similar conformation support the current assumption that they diverged from a common evolutionary ancestor.

When organisms divert in the course of the evolution, their genes will gradually accumulate mutations to produce proteins with quite different amino acid sequences. The more they divert, the less the sequence homology. The frequency of mutations is high at sites which are irrelevant for folding, stability or catalytic properties. Usually, these sites occur at positions in the polypeptide chain where the side chain is on the surface. Only at reversed turns, there is a tendency for residues to have one of the short polar side chains, or to be glycine or proline, the residues most freqently found at this position. Interior residues are changed less frequently and the non-polar nature of -the side chain is conserved fairly well. Since mutation during evolution is a random process, there will be also substitutions that affect functional properties. Only when these substitutions do not cause a disadvantage to the organism, they will be tolerated. As a consequence, variation of these amino acids is much less. Usually, residues directly involved in catalysis are found to be highly conserved. Insertions and deletions tend to occur in surface loops between secondary structure units, with little perturbation of the interior. Usually, in the diverged molecules, elements of secondary structure are arranged in a similar three dimensional topology.

The sequence homology found among the Type-II acylases, as well as the similarity in the molecular architecture of these molecules suggest that Type-IIA and Type-IIB acylases evolved from a single ancestral gene. Also the typical maturation process suggests a common origin. The comparison of sequences of proteins which diverged from a common ancestor can reveal those residues that are involved directly in the functional properties of the enzyme.

In an embodiment of the invention genes encoding known Type-IIA or Type-IIB acylases, for example PenG acylases from *Escherichia coli*, *Kluyvera citrophila*, *Alcaligenes faecalis* or any other organisms producing such enzymes, and glutaryl-Cef acylases from Pseudomonas SE-83 AcyII, Pseudomonas SY-77 or any other organisms producing such enzymes, are mutated in such a way that the enzymes obtain an altered specificity for their substrates.

The alteration of the substrate specificity of PenG acylases (Type-IIA) is achieved in such a way that the mutant enzymes are able to cleave or synthesize penicillin and cephalosporin derivatives possessing side-chains other than phenylacetyl, which is the natural side-chain of Penicillin G. Examples of side-chains which are presently not significantly affected by PenG acylases are acyl groups derived from the dicarboxylic acids succinic acid, glutaric acid, adipic acid and aminoadipic acid (the latter being the natural side-chain of CefC).

In another embodiment of the invention the alteration of the substrate specificity of Cef acylases (Type-IIB) is performed in such a way that the mutant enzymes cleave or synthesize penicillin and cephalosporin derivatives possessing side-chains other than the glutaric acid moiety. Examples of suitable side-chains which may be cleaved or synthesized by such new mutant enzymes are those which are presently not substantially affected by Cef acylases such as the moieties derived from adipic acid and aminoadipic acid (which is the natural side-chain of Cephalosporin C), hydrophobic side-chains such as the moiety derived from phenylacetic acid, the natural side-chain of Penicillin G, and alkyl side-chains.

In still another aspect the alteration of the specificity and activity of acylases (Type-IIA and IIB) is performed for side-chains which are already existing substrates for the said acylases. Using protein engineering the affinity for a substrate may be altered (e.g. increased, expressed by a lower $K_m$ for said substrate) or the catalytic turnover may be altered (e.g. increased, expressed by a higher $k_{cat}$ for said substrate).

In order to achieve alterations in the enzyme molecule, it is of course highly desirable to avail of the 3D structure of said enzyme. Sofar, no high-resolution, 3D-structures of acylases have been published. However, several genes encoding acylases have been sequenced, viz. the genes from *E. coli* and *Kluyvera citrophila* (both Type-IIA) and Pseudomonas SE-83 AcyII (Type-IIB) and this has gained insight into the biological processing of these enzymes. Amino and carboxy terminal sequencing of the isolated subunits revealed that the gene encodes a precursor protein consisting of a signal sequence followed by the α-subunit, a connecting peptide (spacer) and finally the β-subunit.

According to an embodiment of the invention protein engineering of the acylases is carried out following two strategies, depending on the availability of a 3D-structure of the selected acylases. The procedure for determining a 3D-structure is known in the art.

In the absence of a 3D-structure substantially the following strategy is followed:

First, a number of selected acylase genes are cloned into a suitable expression host organism. Preferred microorganisms include *E. coli*, Bacillus, Pseudomonas. Then, the DNA-sequence of each cloned acylase is determined. The DNA-sequences are translated into the corresponding amino acid sequences and these amino acid sequences are then aligned in such a way as to obtain a homology which is as high and relevant as possible. For sequence alignment the types of amino acids may be suitably used as parameters, based on identity but also on similarity. For example, serine is similar to threonine, aspartic acid is similar to glutamic acid, etc. Further suitable parameters are, for example, secondary structure predictions (according to several "standard" procedures, e.g. Chou Fassman), and charge distribution over the sequences. In a is further step, regions are selected for mutation.

The randomly generated mutants are selected by allowing only those mutants to grow which are capable of cleaving a specific substrate. These substrates usually comprise an amide derivative containing as an acyl moiety the side-chain for which the specificity of the said acylase is desired, and as an amine moiety an L-amino acid which is indispensible for growth of the expression host. Therefore, only those hosts, expressing an acylase with the desired substrate specifity, are able to cleave the said amide compound, thereby liberating the essential amino acid. For example, D-α-aminoadipyl L-leucine (hereinafter referred to as aminoadipyl leucine, which compound is in the D-form) can be used as the amide compound to select for a CefC acylase using leucine auxotrophic expression organisms. Another example of an amine moiety is ammonia, which may serve as the sole nitrogen source for the expression host.

The "positive" mutant acylases which reveal the desired substrate specificity, on the basis of the selection procedure used, are then purified and tested. The sites of mutagenesis are identified by sequencing the gene of the mutant acylases. Examples of such mutants are the mutants V62L, Y178H, V179G of SY-77 acylase. Other mutations (including amino acid replacements, deletions and insertions) may also be performed at or around these sites in order to further increase the activity of the mutant acylase. Thus, it will be understood that any combinations of the above-mentioned mutations are included within the present invention. An example of such combination is the mutant L177I/Y178H of SY-77 acylase.

When a 3D-structure of an acylase is available, the first (four) steps of the above procedure still need to be done, but the selection may be based on the 3D-structure. Two approaches may be envisaged:

a) A rational approach, in which one or a few amino acids are mutated into other amino acids. This does not create a large amount of mutants and therefore, all mutants can be handled with respect to purification and testing for their substrate specificity. From the three-dimensional structure one or more amino acids in the active site may be selected in order to be mutated in such a way that the desired side-chain can be accomodated optimally in the active site. For example, accomodating the aminoadipyl side-chain of CefC into a PenG acylase, requires that the binding pocket is first of all enlarged in order to fit in the longer alkyl chain, and secondly that it is supplied with the proper electrostatic environment to bind the amino and/or carboxy group of the aminoadipyl side-chain. As another example, the introduction of the proper electrostatic environment in order to accomodate the positively charged amino group of the side-chain of CefC may change the specificity of a glutaryl-Cef acylase (which already shows some activity with aminoadipyl Cephalosporin) to a CefC acylase.

b) a "targeted random mutagenesis (TRM) approach". Despite the 3D-structure it may be difficult to make predictions. If it is possible to assess that a few amino acids are involved in substrate binding, a targeted random mutagenesis is advantageously performed followed by a selection test as indicated above. This approach yields for example 8000 possible mutants when a set of 3 sites is mutated randomly (with respect to the amino acids, 20*20*20; on DNA level—where the mutants have to be made - this is as many as $(4*4*4)^3=262,000$ possible mutants!).

In a further aspect of the invention it was found that the acylase enzyme from *Alcalipenes faecalis* showed a surprising high degree of homology with the acylases from *E. coli* and *Kluyvera citrophila*. The acylase encoding gene from *Alcaligenes faecalis* was isolated and sequenced and compared with the genes of the two other species. It appeared that a common feature of the sequences is that the genes encode a large polypeptide precursor which may be composed as is depicted in Table 1. The question marks relating to *Alcaligenes faecalis* indicate only that the end of the sequences could not yet be determined unambiguously.

TABLE 1

Number of amino acids per acylase peptide

| Acylase from | signal seq. | α-subunit | connecting peptide | β-subunit |
|---|---|---|---|---|
| *Escherichia coli* | 26 | 209 | 54 | 557 |
| *Kluyvera citrophila* | 26 | 209 | 54 | 555 |
| *Alcaligenes faecalis* | 26 | 210 (?) | 29 (?) | 551 |
| Pseudomonas SE-83 AcyII | 0 | 239 (?) | ? | 535 |
| Pseudomonas SY-77 | 28 | 169 (?) | ? | 521 |

In another aspect of the invention it was found that α- and β-subunit of the acylase from Pseudomonas SY-77 depicted regions with a high sequence homology both with Type-IIA acylases and the Type-IIB SE-83 AcyII acylase. The acylase encoding gene of Pseudomonas SY-77 was isolated and the complete sequence of the gene was obtained. For both Pseudomonas acylases there is no evidence for a connecting peptide between α- and β-subunit. The SY-77 enzyme appeared to have a signal peptide whereas N-terminal sequencing of the SE-83 AcyII showed that the mature α-subunit commenced just after the initiating methionine (Matsuda A. [6]).

The kinetics of Type-II acylases are consistent with catalysis proceeding via an acyl-enzyme intermediate (Mahajan [8]).

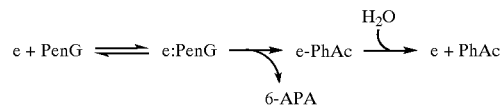

In the first step of the mechanism, the substrate PenG binds to the enzyme to form the non-covalent Michaelis-Menten complex e:PenG. In the subsequent step, the covalent intermediate is formed between the enzyme and the acyl moiety of the substrate (e-PhAc=acylated enzyme; PhAc=phenylacetic acid) with the concomitant release of the first product 6-APA. Deacylation occurs with the aid of a water molecule thereby liberating the second product PhAc and regenerating the enzyme. This mechanism is also in accordance with the observations that PhAc acts as a competitive inhibitor and 6-APA as a non-competitive one.

The above mechanism, which is identical to the one postulated for the serine proteases, together with the finding that phenylmethylsulfonylfluoride (PMSF, a potent inhibitor of serine proteases) inhibits the enzyme (Mahajan [8]), suggests that these enzymes are also serine hydrolases containing a catalytic triad consisting of a serine, histidine and aspartic acid. Such a catalytic triad is not only found in the serine proteases of the trypsin- and subtilisin family, but was recently also discovered in two, structurally different, triacylglycerol lipases (Blow D. [14]; Winkler F. K. [15]; Brady L. [16]) from human pancreas and the fungus *Rhizomucor miehei*. Based on the sequence alignment Ser765 of *Alcaligenes faecalis* acylase is most likely the active site serine. Based on this finding further mutants are provided with altered activity.

In a further aspect of the present invention, the genes coding for the acylases from *Escherichia coli, Alcaligenes faecalis*, Pseudomonas SY-77 and Pseudomonas SE-83 AcyII, respectively, were cloned into the expression host organism *E. coli*.

The DNA sequences of the acylases from *E. coli, Kluyvera citrophila*, Pseudomonas SE-83 AcyII and the partial DNA sequence for Pseudomonas SE-77 were taken from the literature. The DNA sequence for the acylase from *Alcaligenes faecalis* was determined as well as the remainder of the DNA sequence of the Pseudomonas SE-77.

The alignment of the five amino acid sequences revealed a close homology between the PenG acylases (>45%), whereas the homology between the PenG acylases and the glutaryl-Cef acylases was lower (25–35%) while also the homology between the glutaryl-Cef acylases was of that same order. Yet regions of high homology between all five sequences could be detected which points to a possible similar 3D-structure (already supported by the heterodimeric structure).

Regions of particular interest to mutate are the α- and β-subunits of the acylase.

It is to be understood that all amino acids, as used in this specification, are in the L-form, unless otherwise stated. The term "aminoadipyl" is used to indicate the D-α-aminoadipyl moiety.

Mutant β-lactam acylases may also be cloned and expressed in a β-lactam producing microorganism. This would have the advantage that the deacylated β-lactam intermediate can be recovered directly from the fermentation broth. Cephalosporium and Penicillium strains are preferred hosts for this application of mutant β-lactam acylases.

The following Examples are offered by way of illustration and not by way of limitation.

MATERIALS AND METHODS

Cloning and Detection of Acylase Genes

General cloning techniques were performed as described by Maniatis [17], Ausubel [18] and Perbal [19]. These handbooks describe in detail the protocols for construction and propagation of rDNA molecules, the procedures for making gene libraries and the protocols for mutating DNA in a site-directed or random fashion. Enzymes used for DNA manipulations were purchased from commercial suppliers and used according to their instructions. Plasmids and *E. coli* cloning hosts were obtained from public culture collections.

Construction of Plasmid pUNN1

Plasmid pUNN1 was constructed as follows: Plasmid pUB110 (*S. aureus*) was cut with SnaBI and TaaI and the fragment carrying the neomycin resistance gene was cloned into SmaI, AccI digested pUC19 resulting in pPNeo. The small EcoRI-ScaI fragment of pPNeo was exchanged for the small EcoRI-ScaII fragment of pUC18 resulting in pPNeoII. Then the small Pst-Pst fragment of pPNeoII was cloned into the single PstI site of pUN121 (Nilsson [20]). After KinI, XbaI digestion, nuclease S1 treatment and ligation, plasmid PUNNI was recovered. This plasmid can be used as a positive selection vector (Nilsson, ibid.) and has the advantage over common cloning vectors that it does not contain a β-lactamase gene, which may destroy β-lactam antibiotics.

Enzyme Assays

Acylase activity was assayed by a spectrophotometric method based on the detection of primary amino groups with the fluorophor fluorescamine (S. Underfriend et al. [32]). For the detection of 7-ACA the method was adapted by Reyes et al. [21].

In order to determine enzymatic activity the enzyme was incubated with substrate at room temperature. The composition of the reaction mixture was: 20 mM sodium phosphate buffer pH 7.5, 1.2 mM substrate, 1.0 mM P-lactamase inhibitor 6-bromo-penicillanic acid and enzyme. The reaction was stopped by adding 0.5 N HCl. Slow reactions were assayed immediately without prior stopping the reaction with HCl. From the reaction mixture 100 microliters were taken and mixed with 800 μl 0.2 M sodium acetate buffer pH 4.5 and 100 μl of fluorescamine which was prepared in AR acetone (1 mg/ml). When the substrate contained an amino acid instead of 7-ACA, the sodium acetate buffer was replaced by 0.2 M sodium phosphate pH 7.5. After 15 minutes the absorption at 378 nm was determined with an Uvicon 860 spectrophotometer and corrected for the appropriate blancs. Through a calibration curve the absorption at 378 nm can be related to the number of free amino groups released by hydrolysis of the substrate.

Mutagenesis of Acylase Genes

Site-directed mutagenesis of cloned DNA fragments was carried out as described by Stanssens [22] with the aid of the phasmid pMa/c system. Suitable gapped duplex molecules of acylase genes were constructed. With specific mismatch oligonucleotides site directed mutations were introduced. Expression of acylase genes was obtained in *E. coli* WK6 either from the homologous expression signals or from the *E. coli* lac, tac or trp promoter (De Boer [23]). Gapped duplex molecules were annealed with "spiked" oligonucleotides to obtain a region-targeted random mutagenesis (Hermes [24]. These "spiked" oligonucleotides were prepared by including traces of all 4 nucleotides during the synthesis of oligonucleotides on an Applied Biosystems DNA synthesizer. Alternatively, random mutagenesis of the gapped DNA was performed enzymatically with a method modified from Leethovaara [25]. By the choice of the gap the region to be mutagenised enzymatically was selected.

In another type of experiments targeted random mutagenesis was performed. This comprises the inclusion of all four bases at the codon for a specific amino acid during the synthesis of the oligonucleotide. In doing so, a mutagenic oligonucleotide which can mutate any amino acid is all other possible amino acids can be synthesized. A single amino acid position or a combination of several positions can be mutagenized in that way. Alternatively, random mutagenesis based on the PCR technology can be used [36].

Selective Media

Selective media for phenylacetyl leucine ("fal") were prepared as described by Garcia [26]. Minimal plates are as follows: M63 minimal agar, 2 g/l glucose, 1 mg/l thiamine, 10 mg/l proline and the appropriate antibiotic (50 μg/ml chloramphenicol (cap) or 25 μg/ml ampicillin (amp)). For selections on side-chain specificity (e.g adipyl or aminoadipyl) of acylases, 100 μg/l of the corresponding acyl leucine was included into minimal plates. Transformants or mutants of *E. coli* HB101 (Leu) growing exclusively in the presence of the acyl leucine are considered to harbor an acylase gene with the desired specificity. Instead of leucine the amino acid moiety of the selective substrate was varied.

In such case a suitable auxotrophic mutant of E. coli was used for selection. For example, selection on the substrate N-adipyl serine was carried out with E. coli strain PC2051 as a host (obtained from Phabagen, Utrecht, the Netherlands). Phenylacetyl leucine, aminoadipyl leucine, glutaryl leucine, adipyl alanine and adipyl serine were purchased from LGSS, Transferbureau Nijmegen, the Netherlands.

Phenylacetyl amide was added to a final concentration of 15 mM to minimal M63 medium supplemented with 0.2% of either succinate, glycerol or glucose as carbon source, and thiamine (1 $\mu$g/ml)$_1$ proline (10 $\mu$g/ml), and the appropriate antibiotic. All salts in the basal medium were replaced by the corresponding salts containing either Na$^+$ or K$^+$ ions in order to ensure selective growth on the amide (Daumy [12]). Amides with the desired side-chains were purchased from commercial suppliers or prepared according to standard techniques. E. coli strains JM101, WK6, HB101, PC2051 and PC1243 were used as hosts to select for mutant genes with specificity for the selective amides.

Isolation Procedure Wild-type and Mutant Glutaryl Acylases

Cells were harvested by centrifugation and resuspended in 10 mM sodium phosphate buffer pH 7.4 containing 140 mM NaCl. The cells were disrupted through sonification (6×20 sec, 100 W, 100 mm bar, Labsonic 1510; after every 20 seconds the cells were cooled on ice for 30 seconds). Subsequently, the suspension was centrifugated. The sonification procedure was repeated with the resuspended pellet and finally the cell debris was removed by centrifugation. Supernatants were pooled and ammonium sulphate was added upto a 30% saturation. After 30 minutes stirring precipitated material was removed by centrifugation. The ammonium sulphate concentration of the supernatant was increased to 60% saturation and after 30 minutes the precipitate was collected by centrifugation. The pellet was dissolved in 20 mM sodium phosphate buffer pH 7.5 and extensively dialyzed against the same buffer.

EXAMPLE 1

Cloning of an E. coli Penicillin Acylase Gene

From the published restriction map and sequence of E. coli ATCC 11105 penicillin acylase gene (Sang-Jin [27]) it was concluded that the HindIII-SmaI fragment of 2.9 kb comprises the acylase gene ("pac"). Chromosomal DNA was digested with HindIII and SmaI and fractionated on a 0.5% agarose gel. Fractions from 2 to 4 kb were purified with Geneclean (BI0101, La Jolla, Calif.) and hybridized with the following oligonucleotide DNA probe (SEQ. ID NO:8:

TCGTACATTTTCAGCTGATCTTCATAGTGCTTATC derived from the sequence of E. coli pac.

Figure 3:
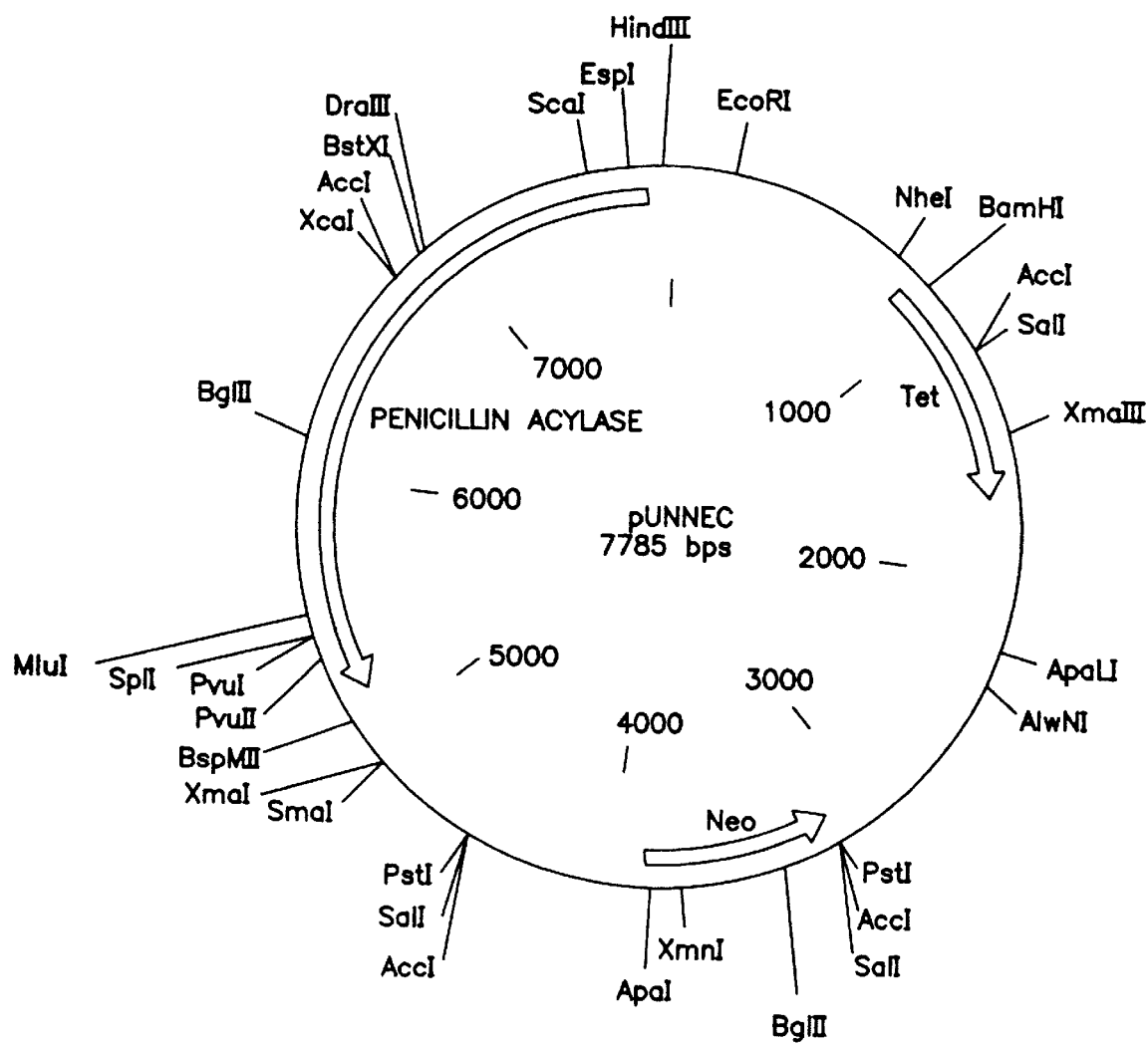
FIG. 3: restriction map of plasmid pUNNEC harboring the *E. coli* ATCC 11105 penicillin acylase gene.

The positively hybridizing fraction was then ligated into vector pUNN1 and transformed into E. coli HB101. Filter hybridization of 2000 transformants with the above-mentioned oligo probe resulted in the identification of plasmid pUNNEC1. The structure is shown in FIG. 3.

Colonies carrying pUNNEC1 were grown on HI-agar plates for 24 hours at 30° C. Then the plates were overlayered with 5 ml nutrient broth topagar containing Penicillin G (5 mg/ml) and 0.5 ml of an overnight culture of Serratia marcescens ATCC 27117 and incubated for another 24 hours. Penicillin acylase activity of the transformants can be seen from the inhibition zone around the colony, which results from a high sensitivity of Serratia marcescens for 6-APA (Meevootisom [28]).

EXAMPLE 2

Cloning of an Alcaligenes faecalis Penicillin Acylase Gene

Figure 4:
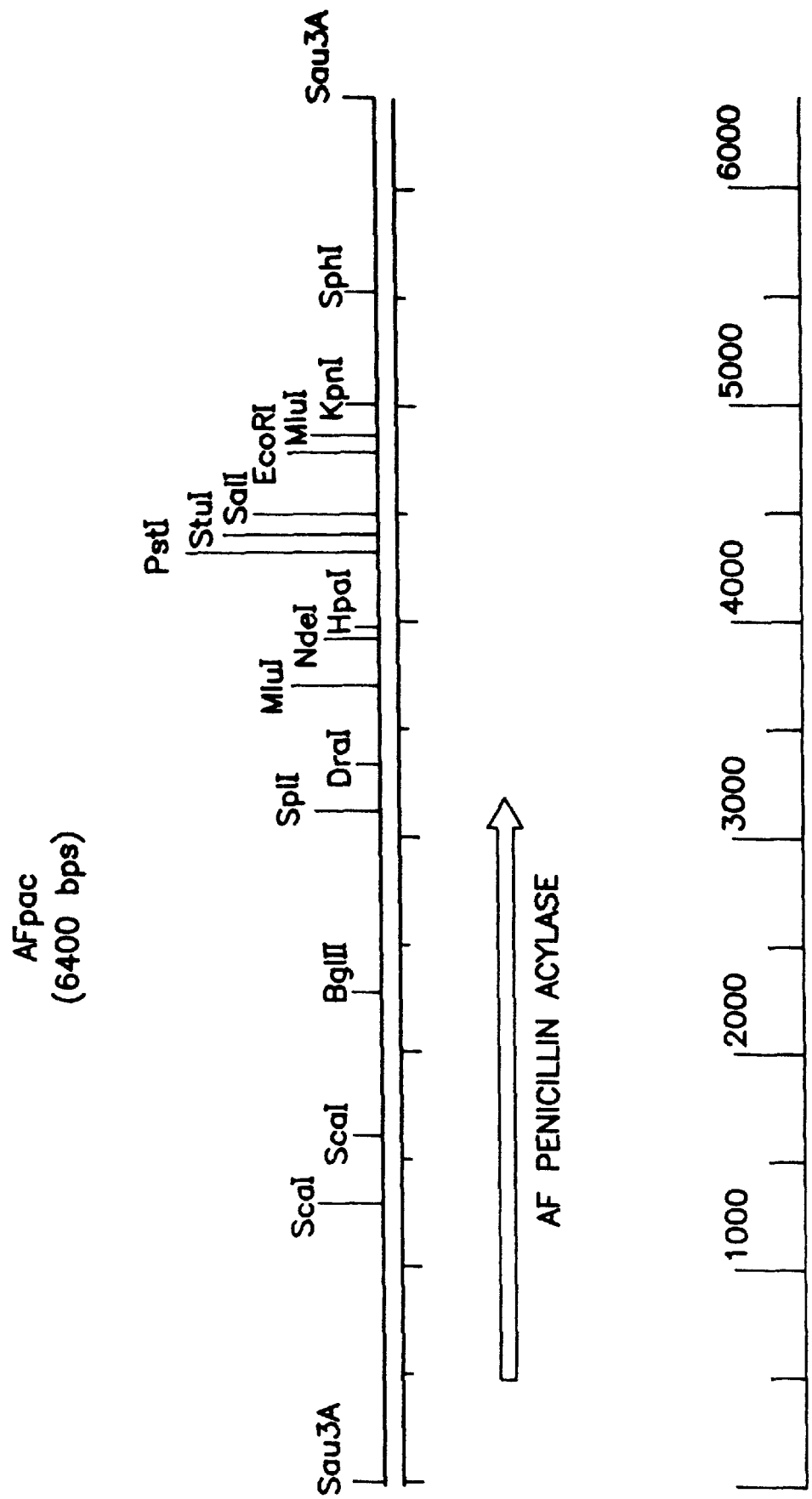
FIG. 4: restriction map of the 6.4 kb insert of plasmid pAF1.

Chromosomal DNA of Alcaligenes faecalis strain ATCC 19018 (=NCTC415) was isolated and partially digested with Sau3A. Fractions ranging from 4 kb to 7 kb were purified and ligated into vector pACY184, which was digested with BamHI. DNA was transformed into E. coli HB101 and plated onto fal-plates (see methods). Two positive clones, pAF1 and pAF2, could be identified. These clones were also tested with positive result in the Serratia marcescens overlay technique. The 6.4 kb insert of the pAF1 plasmid is shown in FIG. 4.

The localization of the gene was determined with the aid of an oligonucleotide designed on the NH$_2$ terminal sequence of the β-subunit of A. faecalis penicillin acylase. The amino acid sequence (SEQ. ID NO:9)reads:

S-N-L-W-S-T/R-(C)-P-E-(C)-V

The following oligonucleotide (SEQ ID NO:10) was used as a hybridization probe on the pAF1 insert:

AGC AAC CTG TGG AGC A/C C/G C TGC CCG GAG TGC GT

From the position of the hybriding signal on the restriction map the orientation of the A. faecalis pac gene was determined (FIG. 4). The 3.9 kb Sau3A-NdeI subclone of the 6.4 kb insert, was shown to give penicillin acylase activity, whereas the 3.1 kb Sau3A-Sph1 fragment was inactive (FIG. 4). The DNA sequence of the 3.9 kb insert was determined by dedeoxy sequencing of suitable fragments in pTZ18R and pTZ19R (Pharmacia). The encoding DNA sequence and the derived amino acid sequence for A. faecalis penicillin acylase are shown in FIG. 5.

EXAMPLE 3

Cloning of a Pseudomonas Glutaryl-cephalosporin acylase gene (A)

Pseudomonas SY-77 produces an enzyme capable of hydrolyzing glutaryl amidocephalosporanic acid into 7-ACA and glutaric acid. The gene encoding this enzyme was cloned (Matsuda [29]). DNA extracted from Pseudomonas SY-77 was digested with HDAI and SmaI and cloned into SmaI linearized vector pUNN1 in strain HB101. Transformants were selected on neomycin plates and hybridized with a probe derived from the DNA sequence (SEQ ID NO:11) (Matsuda [29], ibid.):

ATG CTG AGA GTT CTG CAC CGG GCG GCG TCC GCC TTG

Figure 6:
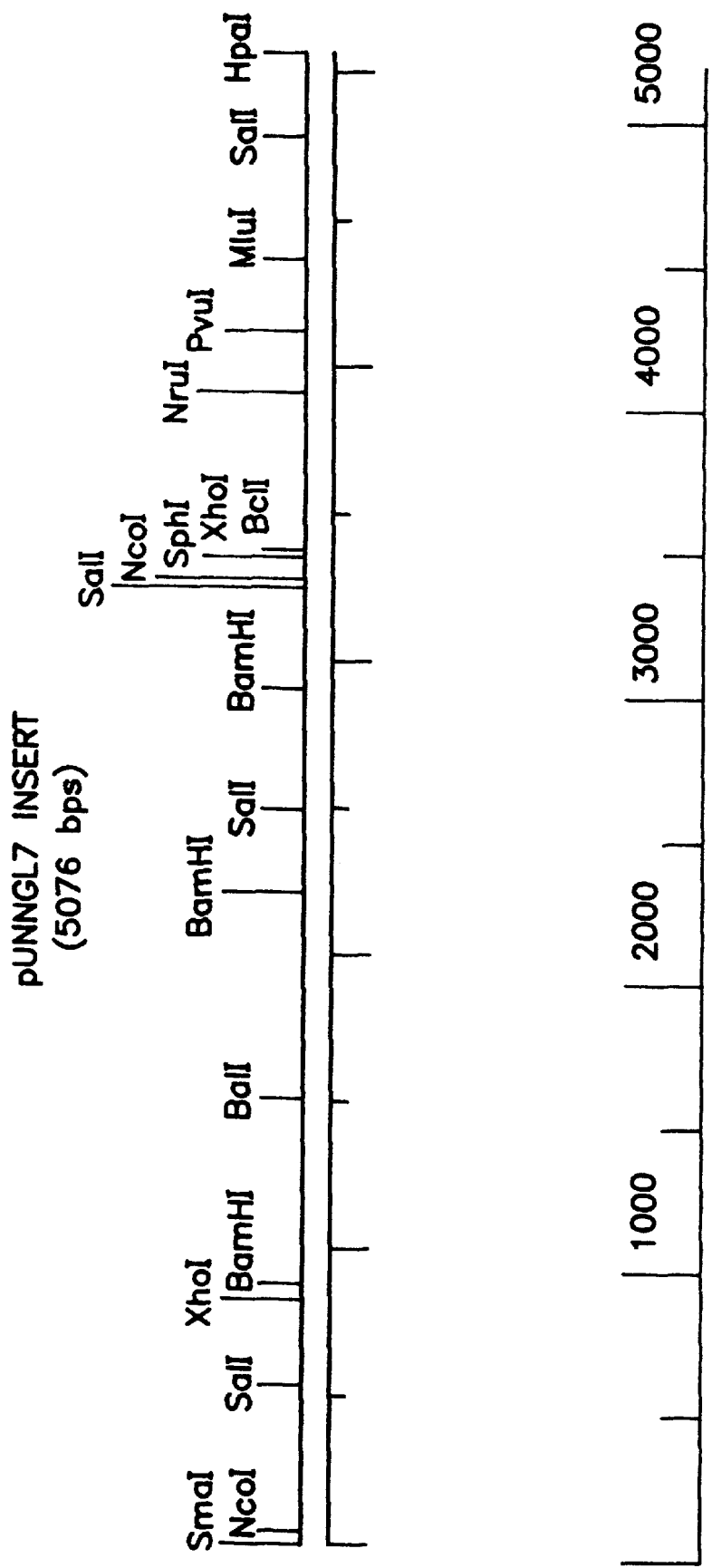
FIG. 6: insert of pUNNGL7 harboring the Pseudomonas SY-77 glutaryl-Cef acylase gene.
Figure 7:
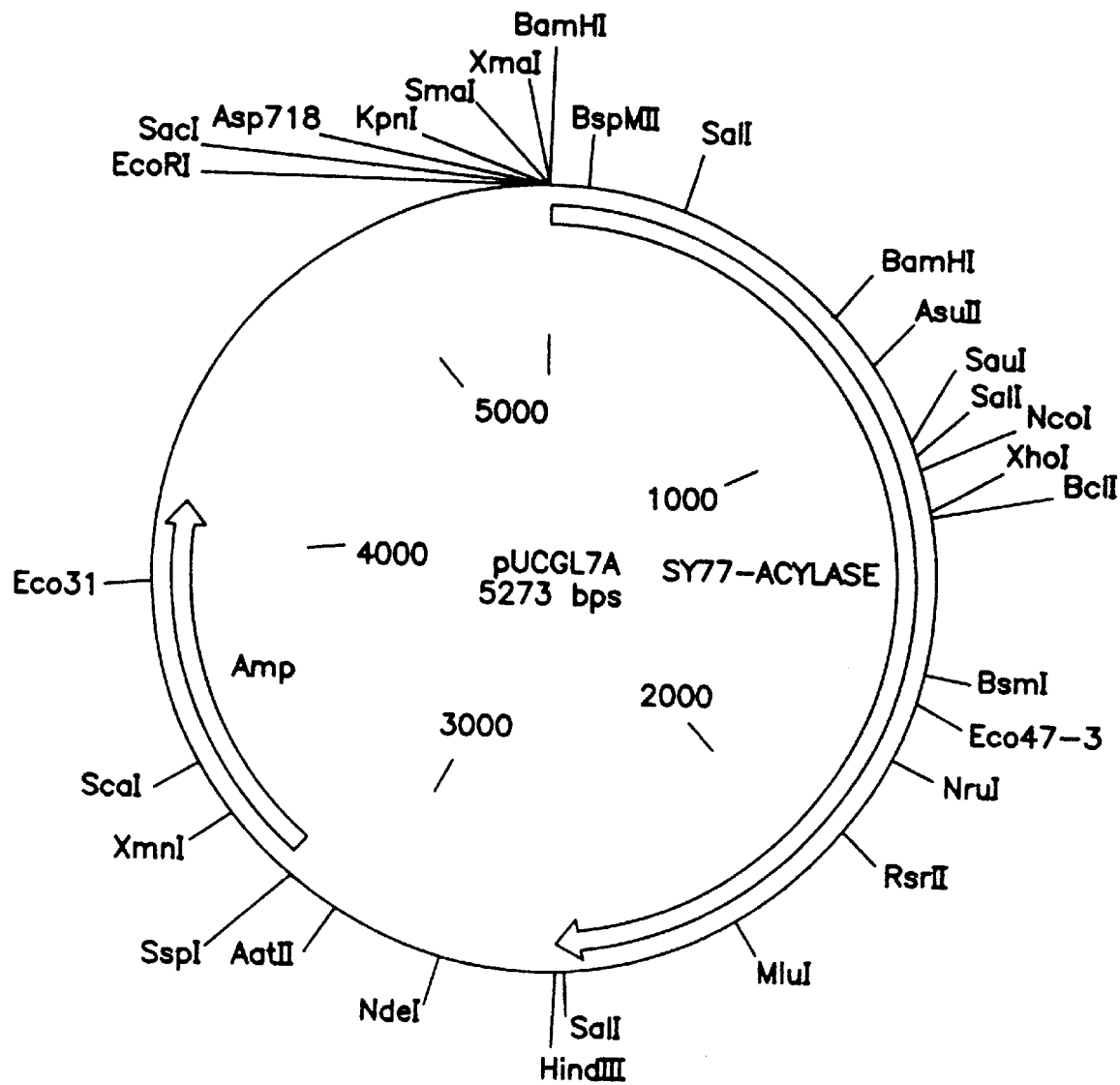
FIG. 7: restriction map of plasmid pUCGL7A: plasmid pUC18 harboring the glutaryl-Cef acylase gene of Pseudomonas SY-77.

The hybridizing plasmid pUNNGL-7 was shown to harbor the acylase encoding fragment of Pseudomonas SY-77 by restriction mapping (FIG. 6). This plasmid was purified and partially digested with BamHI and SalI. Fragments of 2.6 kb were purified from agarose gel (Geneclean) and ligated into BamHI, SalI linearized pUC18 (Pharmacia). The resulting plasmid i5 was characterized as shown in FIG. 7. Colonies were grown in LBC medium and analyzed for acylase activity (see Methods). It was shown that plasmid pUCGL-7A produces 5 Units/g cell pellet.

The same EmHI-SalI fragment was also cloned into plasmid pTZ19R (Pharmacia) resulting in plasmid pTZ19GL-7A. The total DNA sequence of the 2.6 kb BamHI-SalI fragment was determined (see FIG. 13A–13D) and the complete amino acid sequence of SY-77 acylase was derived. The first 311 residues (out of the total of 850) are identical to the published partial sequence of SY-77 acylase (Matsuda [29], ibid.).

EXAMPLE 4

Cloning of a Pseudomonas Glutaryl-cephalosporin acylase gene (B)

Pseudomonas SE-83 produces an acylase capable of hydrolyzing glutaryl amidocephalosporanic acid and cephalosporin C into 7-ACA and glutaric acid. A gene encoding the responsible enzyme was cloned from the chromosomal DNA of Pseudomonas SE-83 (AcyII in Matsuda [30]). From these data it was decided to clone a 6.0 kb =II fragment of Pseudomonas SE-83 into BclI linearized pUN121 (Nilsson [20]). Resulting transformants in JM101 were hybridized with an oligonucleotide (SEQ ID NO:12) derived from the DNA sequence of AcyII (Matsuda [30], ibid.):

GG CCG ATG CTC CTC GCC CCA GCC GCG CCC GGT CAG GTT CTG CGT CGC GAC GGA

Figure 8:
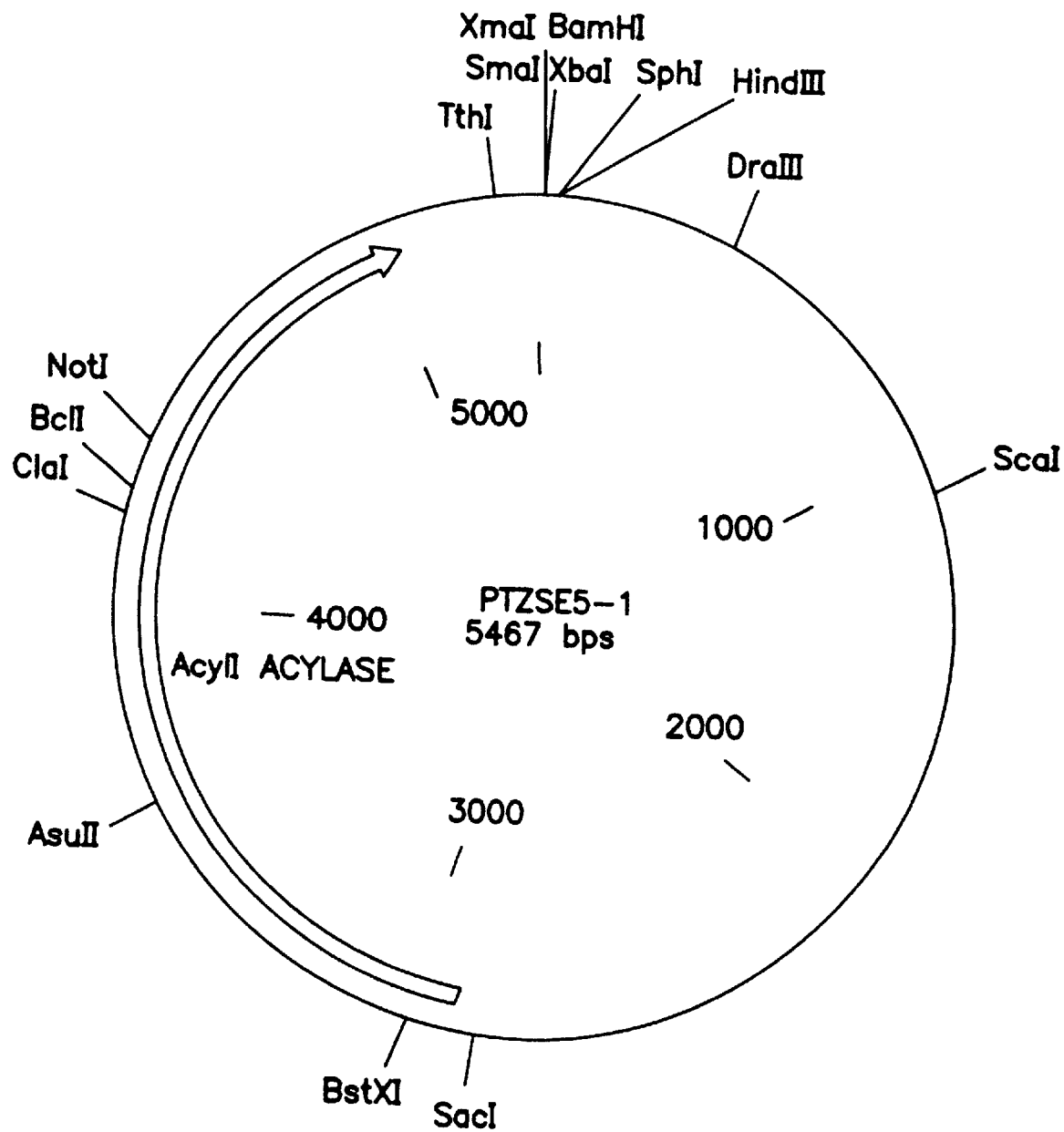
FIG. 8: restriction map of plasmid pTZSE5-1: plasmid pTZ18R harboring the Pseudomonas SE-83 AcyII gene.

A positive clone, pUNSE-5, was isolated. A 2.3 kb SacI-SmaI fragment of plasmid pUNSE-5 was purified and subcloned into vector pTZ18 to give pTZ18SE5-1 (FIG. 8).

EXAMPLE 5

Homology Comparison of Type-II Acylases

In FIG. 14 the amino acid sequence of the precursor form of various acylases are aligned, with respect to the sequence of the acylase of *Escherichia coli*.

The acylases originating from *Escherichia coli* (*E.col*), *Kluvvera citroihila* (*K.cit*) and *Alcaligenes faecalis* (*A.fae*) are Type-IIA acylases (PenG acylase), whereas the acylases from Pseudomonas (SE-83 and SY-77) are the Type-IIB acylases (glutaryl-Cef acylase).

Also indicated in FIG. 14A–14E are the positions where the leader, α-subunit, connecting peptide and β-subunit are starting. These positions were deduced from the peptide-sequencing data summarized in Table 2. Where no peptide sequencing data were available, positions were deduced from the corresponding positions in *E. coli*.

TABLE 3

Homology matrix of the α-subunits of Type-II acylases

| | 1. | 2. | 3. | 4. |
|---|---|---|---|---|
| Type-IIA | | | | |
| 1. E. col | 100 | | | |
| 2. K. cit | 83 (89) | 100 | | |
| 3. A. fae | 47 (60) | 46 (61) | 100 | |
| Type-IIB | | | | |
| 4. SE-83 | 26 (38) | 26 (45) | 32 (42) | 100 |
| 5. SY-77 | 30 (40) | 29 (42) | 28 (38) | 25 (32) |

TABLE 4

Homology matrix of the β-subunits of Type-II acylases

| | 1. | 2. | 3. | 4. |
|---|---|---|---|---|
| Type-IIA | | | | |
| 1. E. col | 100 | | | |
| 2. K. cit | 86 (91) | 100 | | |
| 3. A. fae | 41 (56) | 41 (55) | 100 | |
| Type-IIB | | | | |
| 4. SE-83 | 22 (35) | 23 (36) | 27 (34) | 100 |
| 5. SY-77 | 26 (35) | 27 (39) | 22 (32) | 28 (36) |

The values in parentheses denote the homology based on similar residues whereas the values in front of the brackets are for identical residues.

It can be seen from Tables 3 and 4 that there is a high degree of homology within the Type-IIA acylases ranging from 46–83% for the α-subunits to 41–86% for the β-subunits. This becomes even higher if similarity between residues (e.g. Ser/Thr, Asp/Glu, Arg/Lys etc.) is taken into account. This high degree of homology suggests that the 3D-structure of the three PenG acylases will be very similar.

The homology between Type-IIA and Type-IIB acylases is lower (22–30%). Again these values become higher if the similarity between amino acids is taken into account (35–45%). Therefore, the Type-IIB acylases appear to be structurally related to the Type-IIA acylases. The homology is not equally distributed over the amino acid sequences, but certain areas of high homology do occur.

The homologies between the amino acid sequences were calculated for the (putative) α-subunits and the β-subunits (Tables 3 and 4, respectively).

The determination of the sequences of the *Alcaligenes faecalis* and Pseudomonas SY-77 acylases makes it possible to identify residues which may be directly involved in catalysis.

TABLE 2

Peptide sequencing data of α- and β-subunits of Type-II acylases

| | α-subunit | | β-subunit | |
|---|---|---|---|---|
| Enzyme | N-terminus | C-terminus | N-terminus | Ref. |
| E. col | H₂N-EQSSS (SEQ ID NO: 13) | QTA-COOH (SEQ ID NO: 14) | H₂N-SNM (SEQ ID NO: 15) | [10] |
| E. col | H₂N-EQSSSEI (SEQ ID NO: 16) | NQQNSQTA-COOH (SEQ ID NO: 17) | H₂N-SNMVIG (SEQ ID NO: 18) | [31] |
| K. cit | H₂N-ASPPTEVK (SEQ ID NO: 19) | TOTA-COOH (SEQ ID NO: 20) | H₂N-SNMWVIGK (SEQ ID NO: 21) | [11] |
| A. fae | H₂N-Q?Q?VEVM?T (SEQ ID NO: 22) | not determined | H₂N-SNLWST?PE?V (SEQ ID NO: 23) | |
| SE-83 | H₂N-TMAAKT (SEQ ID NO: 24) . . . | not determined | H₂N-SNNWA (SEQ ID NO: 25) . . . | [8] |
| SY-77 | H₂N-EPTSTPQA (SEQ ID NO: 26) . . . | not determined | H₂N-SNS?AVA (SEQ ID NO: 27) . . . | [29] |

The observation that Type-II acylases are inhibited by PMSF suggests strongly that an activated serine is involved in catalysis. Activated serines have been observed in serine proteases, and in lipases. They are always found together with a histidine and an aspartic acid, forming a catalytic triad.

The alignment of the sequences in FIG. 14 shows only 3 conserved serines: Ser174, Ser266 and Ser765 (*A. faecalis* numbering).

Ser174 is located in the α-subunit in a rather well conserved region within the Type-IIA acylases which, however, is poorly conserved in the Type-IIB acylases (FIG. 14A–14E). Taking also into account the experimental observation that the PMSF-sensitive amino acid is located on the β-subunit (Daumy [12]), Ser174 is unlikely to be the active site serine.

Ser266 is located at the N-terminus of the β-subunit and most likely conserved because it is essential for the maturation of the enzyme. It is therefore also an unlikely candidate to be the active site serine.

Ser765 is located on the β-subunit (confirming the experimental result that the PMSF-sensitive amino acid is located at the β-subunit) and therefore very likely the active site serine. The consensus sequence around this serine is . . . -Gly-XXX-Ser- . . .

The glycine preceding the serine is common to all serine hydrolases (Blow [14]).

Two different histidines are conserved throughout the five sequences (FIG. 14A–14E): His42 and His777. They both are in a region which is highly conserved in all sequences. His777, however, is rather close to the postulated active site serine at position 765 and therefore an unlikely candidate. On the contrary, His42 is in a region of high homology. Assuming that this His42 is the active site histidine, being localized on the α-subunit, is also in accordance with the experimental observations that only the heterodimer is the active form of the enzym (i.e. the serine on the β- and the histidine on the α-subunit).

With respect to the third residue of the proposed catalytic triad, there are three candidates found in the β-subunit: Asp448, Asp590, Asp780 and one in the α-subunit: Asp36. The latter is contained at the start of a highly conserved region, yet close to the proposed active site His42. Similarly, the Asp780 is contained in a highly conserved region, but close to the proposed active Ser765. Asp448 and Asp590 are both in a moderately conserved region and therefore both are likely candidates to be the active site aspartic acid.

EXAMPLE 6

Selection of Residues for Mutagenesis based on Type-IIA acylases

In this Example the amino acid residues are selected which may be mutated in order to obtain acylases with altered biochemical properties. These altered properties may result in an alteration of the substrate specificity of Type-II acylases towards the acylation and/or deacylation of certain β-lactam antibiotics.

The criteria for the selection are outlined while at the same time reference is made to FIGS. 15A–15B and FIGS. 16A–16B which contain all selected positions. For reasons of simplicity, the residues given are those for the Type-IIA acylase from *Alcaligenes faecalis*. The corresponding residues in the other acylases may be found using the aligned sequence data from FIG. 14.

The selection of the regions for mutagenesis was based on the following criteria:

1) In order to change the substrate specificity of the Type-II acylases, the mutations were restricted to the mature α- and β-subunits. This means residues 27–236 (α-subunit) and 266–816 (β-subunit), resulting in a total of 210 and 551 residues, respectively.

2) The amino acids of the PenG-acylases (Type-IIA) which are binding the hydrophobic phenylacetyl sidechain of PenG will be conserved in the Type-IIA acylases and, due to the different substrate specificities, probably not in the Type-IIB acylases. Therefore, from the α- and β-subunits those residues are preferably selected which, in the alignment of FIG. 14A–14E, are identical or similar in the Type-IIA acylases from *E. coli, Kluyvera citrophila* and *Alcaligenes faecalis*.

A position is said to contain a similar amino acid residue when the residues found at that position belong to one of the following groups:

a) Hydrophobic residues—This group includes the amino acids isoleucine, valine, leucine, cysteine, methionine, alanine, phenylalanine, tryptophan and tyrosine.

b) Small, non-bulky residues with a high Propensity to be in a flexible segment—This group includes alanine, glycine, serine, threonine, proline, valine and cysteine.

c) Polar or charged residues—This group includes serine, threonine, histidine, glutamine, asparagine, aspartic acid, glutamic acid, arginine and lysine.

The number of positions to be considered for matagenesis in the α-subunit is restricted by these selection criteria to 169 (80%) and in the β-subunit to 416 (75%). In FIGS. 15*a* and 15*b* these selected residues are summarized in the columns with heading 1. The numbers refer to the positions of the respective amino acids in the sequence of the *Alcaligenes faecalis* acylase as given in FIG. 14A–14E.

3) A preferred group is selected based on the assumption that, since the interactions between the PenG-acylase and the side chain of PenG are supposed to be highly hydrophobic in nature, only those conserved and similar amino acids may be selected which are not charged. This means omission of any selected position that contains at least one charged residue in a conserved or similar set as defined above for group c. This selection criterion further restricts the number of preferred amino acid positions in the α-subunit to 119 (57%) and the β-subunit to 304 (55%). FIGS. 15A–15B and FIGS. 16A–16D summarize these residues in the columns with the heading 2.

4) A further preferred group is selected based on the observation that conserved glycine and proline residues usually fulfill a structural role in a protein rather than a catalytic one. Leaving out the conserved Gly's and Pro's from the selected set of amino acids, results in a more preferred group consisting of 102 amino acids in the α-subunit (49%) and 258 in the β-subunit (47%)—FIGS. 15A–15B and FIGS. 16A–16D summarize this group under heading 3. This set of amino acids consists therefore of conserved and similar residues with the exception of the charged amino acids, conserved glycines and conserved prolines.

5) A still more preferred group of selected amino acids is obtained on the assumption that it is also less probable that polar amino acids such as glutamine, asparigine, threonine, serine and others are involved in the binding of the hydrophobic substrate. Using this further selection criterion 74 amino acids in the α-subunit (35%)

and 162 in the β-subunit (29%). FIGS. 15A–15B and 16A–16D summarize these under the heading 4. This set of amino acids consists only of identical and similar hydrophobic amino acids as they are defined above under a) in paragraph 2.

6) Yet a further selection of amino acids to be mutated or capable of being mutated is made on the assumption that the binding site of the Type-IIA acylases is composed of identical hydrophobic amino acids. This reduces the number of selected amino acids further to a final set of 44 conserved, hydrophobic amino acids in the α-subunit (being 21% of the total number of amino acids in the α-subunit) and of 81 conserved, hydrophobic amino acids in the β-subunit (15% of the total in the β-subunit). Columns 5 in FIGS. 15A–15B and FIGS. 16A–16D show this selected set of amino acids.

EXAMPLE 7

Selection of Residues for Mutagenesis Based on Differences in Polarity Between Type-IIA and Type-IIB Acylases Type-IIB acylases are specific for substrates containing dicarboxylic acids as the acyl moiety, such as succinic, glutaric and adipic acid. This suggests that the binding site is much more polar as compared with the Type-IIA acylases. It might even contain a positive charge to compensate for the negative charge on the substrate side acyl moiety. These features are expected to be conserved among the enzymes revealing this substrate specificity. Therefore, the Type-IIA and Type-IIb acylase sequences were compared in order to find regions which are conserved in both the Type-IIA and the Type-IIB acylase sequences but which have changed polarity in order to obtain a more favorable binding of the negatively charged acyl moiety.

The criteria for the selection are outlined while at the same time reference is made to FIGS. 17A–17B which contain all selected positions. The residues given are those for the Type-IIB acylase SY-77. The corresponding residues in the other acylases can be found using the aligned sequence data from FIG. 14A–14E.

Identification of regions which are conserved in type IIB acylase was performed according to a similar procedure as described in Example 6 for the Type-IIA acylases:

1) Mutations were restricted to the mature α- and β-subunits. This means residues 30–198 (α-subunit) and 199–720 (β-subunit).
2) Select those positions in Type-IIB acylases which contain identical or similar amino acid residues according to the grouping in Example 6. The selected residues are summarized in FIGS. 17A–17B in the columns with heading 1.
3) The further selection is based on the assumption that the interactions between the PenG-acylases (Type-IIA acylases) and the side chain of PenG are highly hydrophobic in nature while for the glutaryl acylase a more polar binding site is assumed which may even harbor positively charged residues. Therefore all positions in the alignment of FIG. 14A–14E which show charge in both the Type-IIA and the Type-IIB acylases were omitted. Only in situations where Type-IIA acylase show an Asp or a Glu while Type-IIB acylases show unambiguously much less negatively charged residues, the position is maintained. Application of this selection further restricts the number of preferred amino acid positions. FIGS. 17A–17B summarize these residues in the columns with the heading 2.
4) A further selection was made by leaving out the conserved Gly's and Pro's from the selected set of amino acids as discussed before in Example 6. See FIGS. 15A–15B and FIGS 16A–16D for a summary of this set of amino acids under heading 3.
5) A further narrowing of the selected amino acids may be obtained by supposing that in Type-IIB glutaryl-Cef acylase it is less likely that hydrophobic amino acids involved in the binding of the negatively charged glutaryl side chain. Therefore positions within the Type-IIB acylases which contain identical or similar hydrofobic residues were omitted from the collection which has remained after step 4. FIGS. 17A–17B summarize the results under the heading 4.
6) The set of residues which has remained contains mainly polar or charged residues. Yet a further selection of amino acids to be mutated or capable of being mutated may be made by assuming that positions which show polar residues in Type-IIA and Type-IIB are likely surface residues not necessarily involved in substrate binding. Therefore these residues were omitted in step 5 in FIGS. 17A–17B.
7) In step 7 those positions were selected which accommodate residues that unlike residues at the corresponding position in Type-IIA acylases may fit in electrostatically with a negatively charged glutaryl side chain. In particular sites which are hydrophobic in Type-IIA and positively charged in Type-IIB acylases were selected for mutagenesis.

EXAMPLE 8

Construction of an Expression/mutagenesis Vector System for Acylase Genes

For the purpose of mutagenesis plasmid pTZ19GL-7A was grown in single stranded DNA form according to the supplier. The following oligonucleotide (SEQ ID NO:28) was used to introduce a NdeI site (CATATG) at the ATG start codon:

CAG AAC TCT CAG CAT ATG TTT CCC CTC TCA

Figure 9:
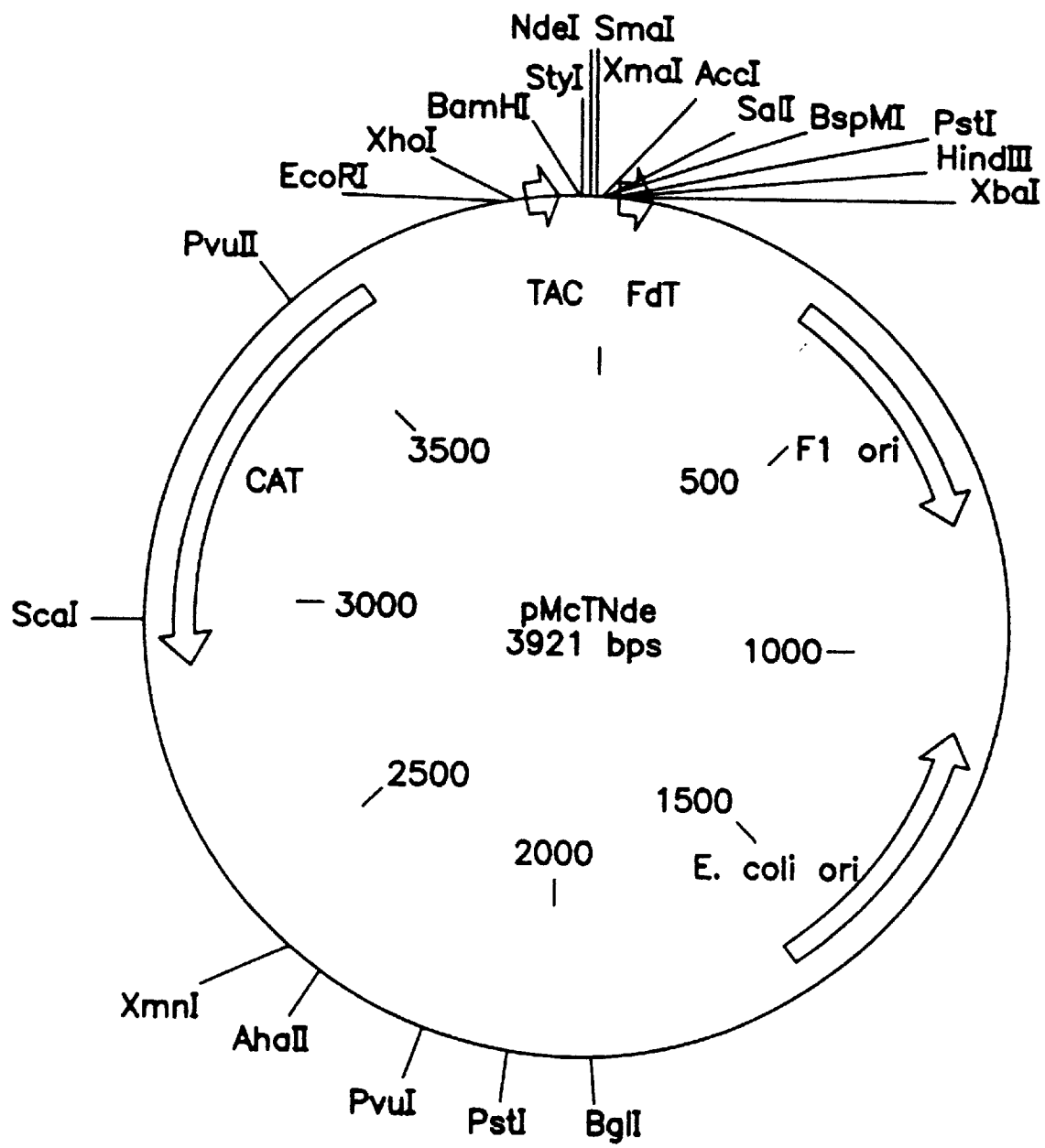
FIG. 9: map of plasmid pMcTNde: a derivative of the mutagenesis expression plasmid pMa/c 5–8 with a NdeI insertion position under control of the TAC promoter.

To enable efficient site-directed and region-directed mutagenesis the NdeI-HindIII fragment of the resulting mutant was subcloned into pMcTNde, a derivative of plasmid pMc-5 (Stanssens [22]). Plasmid pMcTNde was derived from pMc5-8 (EP-A-0351029) by insertion of a fragment encoding the TAC promoter followed by a RBS site and a NdeI cloning site (FIG. 9).

Figure 10:
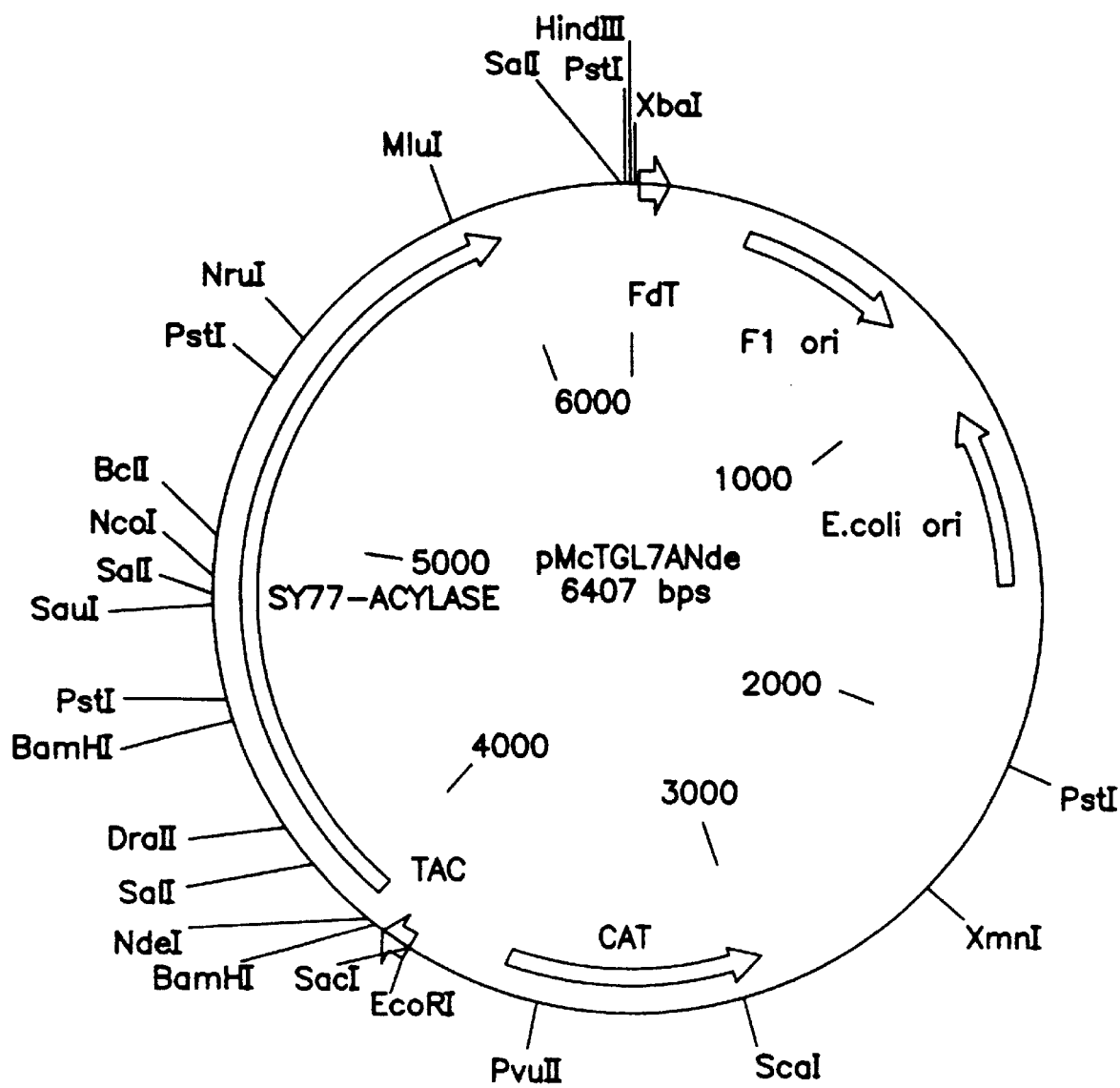
FIG. 10: map of plasmid pMcTGL7ANde, with the SY-77 glutaryl-Cef acylase gene inserted into the NdeI site (harboring the start codon) of plasmid pMcTNde.
Figure 11:
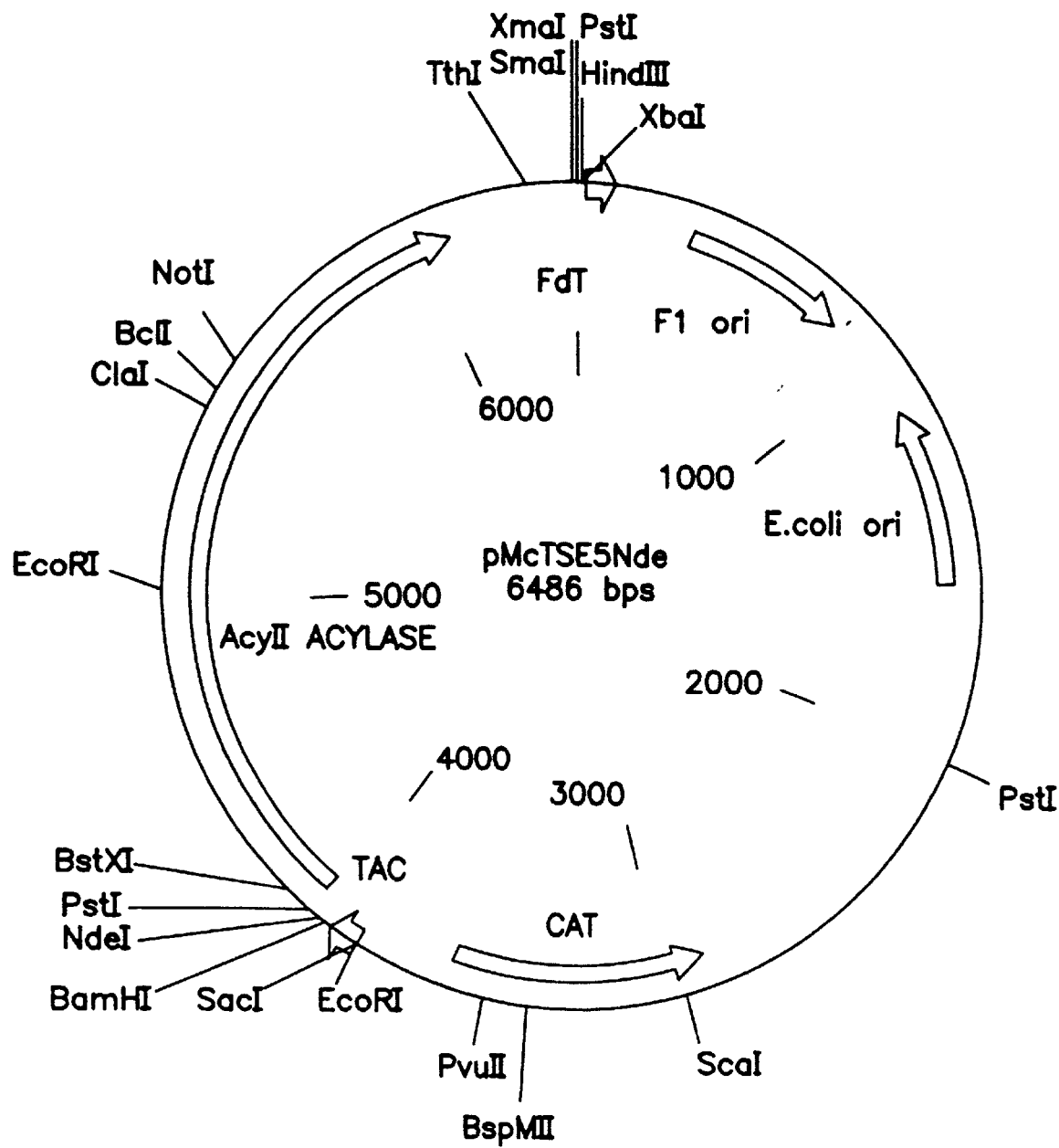
FIG. 11: map of plasmid pMcTSE5Nde: plasmid pMcTNde with the SE-83 AcyII gene inserted in the NdeI site.

In a similar way plasmid pTZSE5-1 was mutagenised with the following oligonucleotide:

AGG TCC AGA CAG CAT ATG ACG ATG GCG to create a NdeI site at the position of the start codon of the acylase gene. The NdeI-SmaI fragment of the resulting mutant was also transferred into plasmid pMcTNde which was cleaved with NdeI and SmaI. The resulting plasmids pMcTGL7ANde (FIG. 10) and pMcTSE5Nde (FIG. 11) direct the synthesis of SY-77 and SE-83 glutaryl-Cef acylase activity, respectively, under the guidance of the strong inducible TAC promoter (De Boer [23]).

Expression levels in *E. coli* WK6 in LBC medium are 2.2 and 12.3 Units/g cell pellet, respectively.

Figure 12:
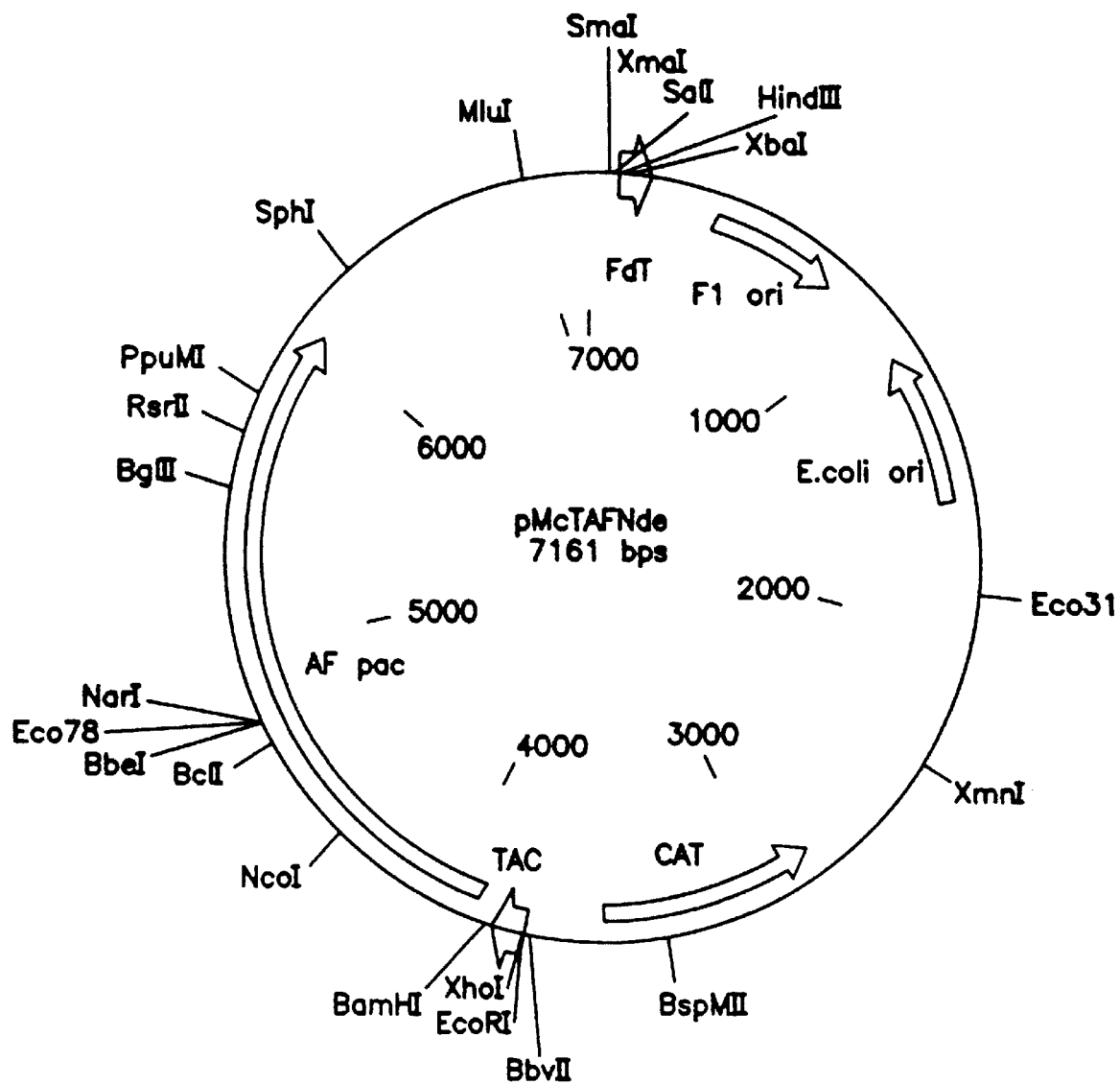
FIG. 12: map of plasmid pMcTAFNde: plasmid pMcTNde with the *A. faecalis* penicillin acylase gene inserted in the NdeI site.

The sequence of the complete acylase encoding region of plasmid pMcTGL7ANde was determined. The result is shown in FIG. 12.

EXAMPLE 9

Mutagenesis of SY-77 Acylase

Plasmid pMaTNdeGL7A was digested with NdeI and NcoI. A gapped duplex with single stranded pMcTNdeGL7A was made and enzymatic mutagenesis on the single stranded gap was performed as described (Methods). The resulting mutant library was transformed into E. coli WK6 MutS and subsequently transformed into E. coli HB101 and selected on aminoadipyl leucine containing minimal plates suplemented with 50 µg/ml cap. Those colonies that were able to grow on these plates and not on minimal plates (because these were leucine revertants) were tested for enzymatic activity on Cephalosporin C. For region directed mutagenesis, spiked oligo's covering various portions of the α-subunit of the acylase gene were incorporated in the same manner as in the site directed mutagenesis protocol (Stanssens [22]).

The following oligonucleotides were used with 2% contamination included during synthesis. Each of the oligo's was designed to harbor a silent mutation allowing the discrimination of wild-type and mutant plasmids based on the occurence or disappearance of a restriction enzyme recognition site. The residues of SY-77 acylase covered by the respective oligonucleotides is given in parenthesis.

AB2237 (residue 50–80)                                    (SEQ ID NO:30)

GCCCTGGCT GCGCGCCTGG GCCCAGCCAT AGCCGTAGAA GGCTGAGGGC

GCGTCTACGC CGTAGATGTG CGGGACGCCG TAGCCGTCCC ACAG

AB2233 (residue 81–109)                                   (SEQ ID NO:31)

CCA GACGGTCGTC TGTTCGTAAT CCGGTCCCCA GTATTCGGCC

CCCTTGCCCC GCGCTTCTCC ATACAGGCGC AGGATATTGT C

AB2234 (residue 109–136)                                  (SEQ ID NO:32)

GAATGCG TCGAGGTTGG CGCGGAAATC AGGCGACTGC TGCGCATACC

ACTGCTGAGC GCGCTCCGGC ACGCCGTTGG TCAGCAG

AB2235 (residue 137–164)                                  (SEQ ID NO:33)

G GCGCCGGAAA CCGGCAGCAC CTGCCGCACG TCGGGCGAGA

TGTCGTCGGG GTTCTGCTGC GCATAGGCGT TGATGCCCGC TGC

AB2236 (residue 165–192)                                  (SEQ ID NO:34)

CGGCG GGTCGCCCTC GCCCAGGGTG CGCCCGGGCG ACGCGACATA

GAGGAAGTTC ATCAGGCGGT GGGCGTGGGC CACCACGTC

For each oligonucleotide a mutant library of >10⁵ independent colonies in E. coli WK6 muts was constructed. These libraries were transformed into E. coli PC2051 for selection on adipyl serine and into E. coli HB101 for selection on aminoadipyl leucine. Colonies selected for growth during 10 days at 30° C. were subsequently tested for reversion to prototrophy and for linkage of growth capability and the presence of plasmid.

The following mutants with good growth capability on adipyl serine were selected:

| Spiked oligo | Mutation (DNA) | Mutation (Amino acid) |
|---|---|---|
| AB 2237 | GTA --> CTA | V62L |
| AB 2236 | TAT --> CAT | Y178H |
|  | GTC --> GGC | V179G |
|  | CTC --> ATC | L177I |
|  | TAT --> CAT | Y178H |

These mutant plasmids were used as starting material for a next round of mutagenesis using spiked oligo's of the α-subunit with a subsequent selection on aminoadipyl leucine (library construction in E. coli HB101).

Since the residues 177, 178 and 179 were identified as crucial for the substrate specificity of SY-77 acylase an approach of targeted random mutagenesis can be applied. For this purpose the following mixed oligonucleotide (SEQ ID NO:35) for Targetted Random Mutagenesis on residues 176, 177, 178, 179 and 180 was synthesized:

```
                                                    187
            GCC CAG GGT GCG GCC GGG CGA NNN NNN NNN
                                                        168
            NNN NNN GTT CAT CAG GCG GTG GGC GTG GGC
```

The same strategy can be applied to the region 60–64 with the following oligo (SEQ. ID. NO. 36):

```
                                                               71
ATA GCC GTA GAA GGC TGA GGG NNN NNN NNN
                                                                                   53
                              NNN NNN GAT GTG CGG GAC GCC GTA GCC
```

Mutant libraries of $10^6$ mutants were generated with the above-mentioned oligonucleotides in E. coli HB101 and selected on aminoadipyl leucine plates.

Targeted random mutagenesis was also performed on the same gapped duplex molecule using the following oligo (SEQ ID NO:37):

GCT GCG CGC CTG NNN NNN GCC NNN GCC NNN GAA NNN TGA GGG CGC GTC

This results in a substitution of amino acid positions 67, 69, 71, 73 and 74 of SY-77 acylase into all possible 20 amino acids. A mutant library of $10^7$ mutants was generated and selected on aminoadipyl leucine plates.

A similar approach as described above for the α-subunit was applied on selected regions of the SY-77 acylase β-subunit. Based on the sequence comparison and selection criteria as described above the following regions were selected for spiked oligo mutagenesis with the following oligo-nucleotides, respectively:

```
AB2399 (residue 253-277)                                       (SEQ ID NO: 38)

ATAGTTGGTG GCCCCCACCA TGCCGTTAAC GGTATTGGTG ATGCCCATCC

GCTGGTTGAA GGCGAAGCGG ATGAC

AB2400 (residue 375-399)                                       (SEQ ID NO: 39)

CTCGGC CCGTTTGGGC GCCACGCCGT TGAAGCTGTA GTTGATGGTA

CCTTCGCGGT CGGCGTAGAC GATGTTGAA

AB2401 (residue 415-442)                                       (SEQ ID NO: 40)

ATTGG AATTCTGCAC GAAGCCGCCC GGCGGATTGG TGACGCGCGG

CAGATCGTCC AGCGGGTGTG TCTCGGTCCA CAGGTAACG

AB2402 (residue 505-529)                                       (SEQ ID NO: 41)

CAGCAG GCGCGCCGCC GCCTGGACCT CGGGATCGGG ATCGATCAGG

GCGGCCGGGA TCAGGTCCGG CAAGGTGCG

AB2403 (residue 668-695)                                       (SEQ ID NO: 42)

GTCG GCGCGCGACA CGCGTTCGAT CTGATCGCTG TAGTGCGTCG

TGCCCGGGTG GCGAGAGTTG CCGTAGCTCA TCAGGCCATA
```

With these oligo's mutant libraries for specific regions of the β-subunit were generated and selected on adipyl serine or aminoadipyl leucine.

Oligo AB2403 encompasses the region around Ser674 which is identified on the basis of sequence comparison with among other A. faecalis Pen-acylase and SY-77 acylase as a candidate for the catalytic serine residue. Mutations around this region are expected to be close to the catalytic site which enhanced the possibility of a change in substrate specificity.

EXAMPLE 10

SY-77 Acylase Mutants with Increased Specificity for Adipyl Serine

Mutants were transformed into a serine auxotroph of E. coli and selected by their ability to grow on a minimal medium which contained adipyl serine as a sole source of carbon. Cells which contained wild-type SY-77 glutaryl acylase did only grow very poorly on such a medium. No significant colonies were observed within 14 days. Colonies which developed within 14 days were selected from the plates and it was verified that they did not grow when adipyl serine was omitted from the plates. Next plasmid DNA was isolated from the selected colonies and transformed to native E. coli cells. It was checked that transformant cells still did grow on the selective medium containing adipyl serine. The following mutants were obtained: V62L, Y178H, V179G and L177I+Y178H.

Figure 19:
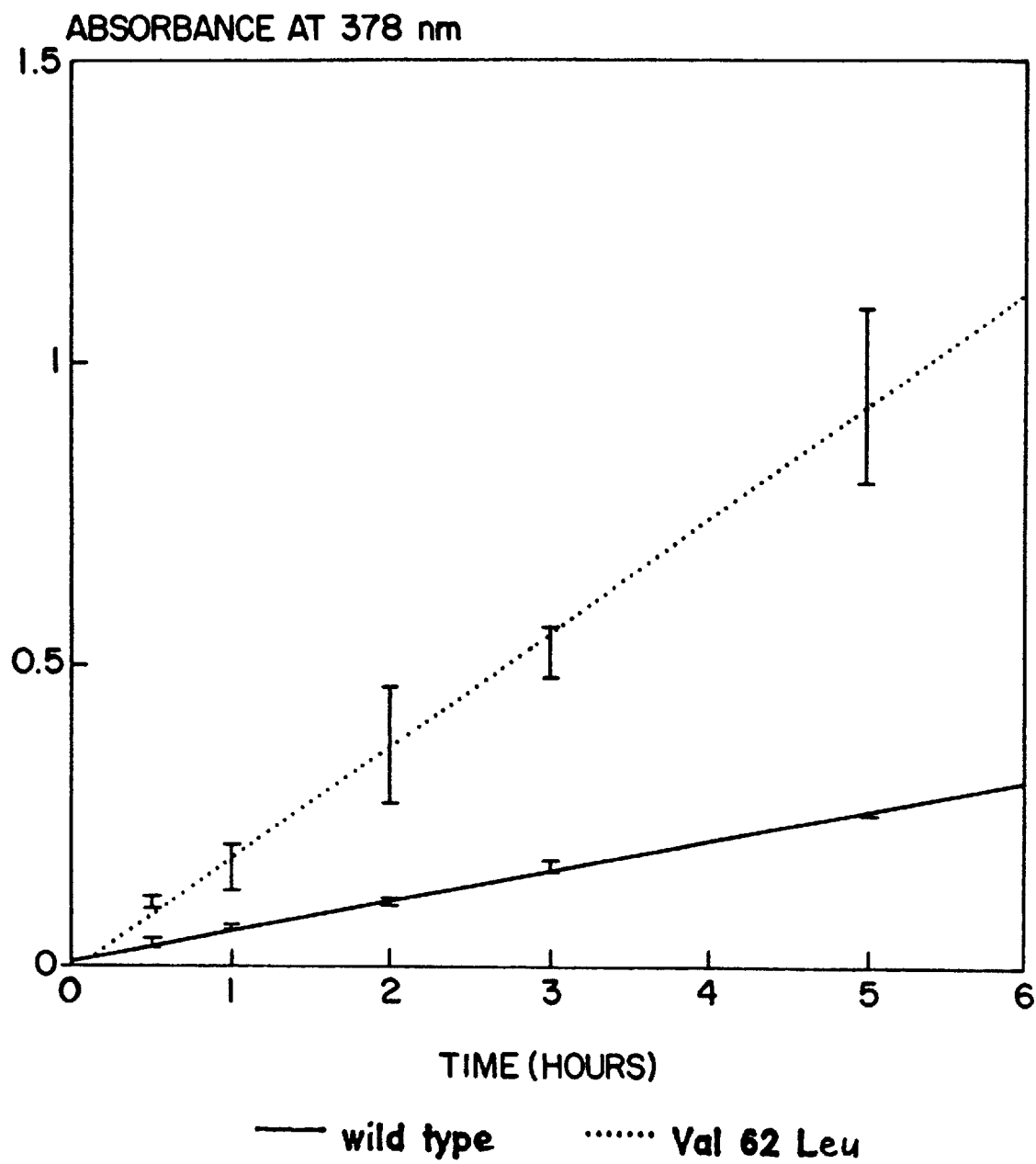
FIG. 19: conversion of adipyl serine by glutaryl acylase SY-77 wild-type and mutant V62L. Enzymes were dosed in such a way that the same activity on glutaryl 7-ACA was obtained.
Figure 20:
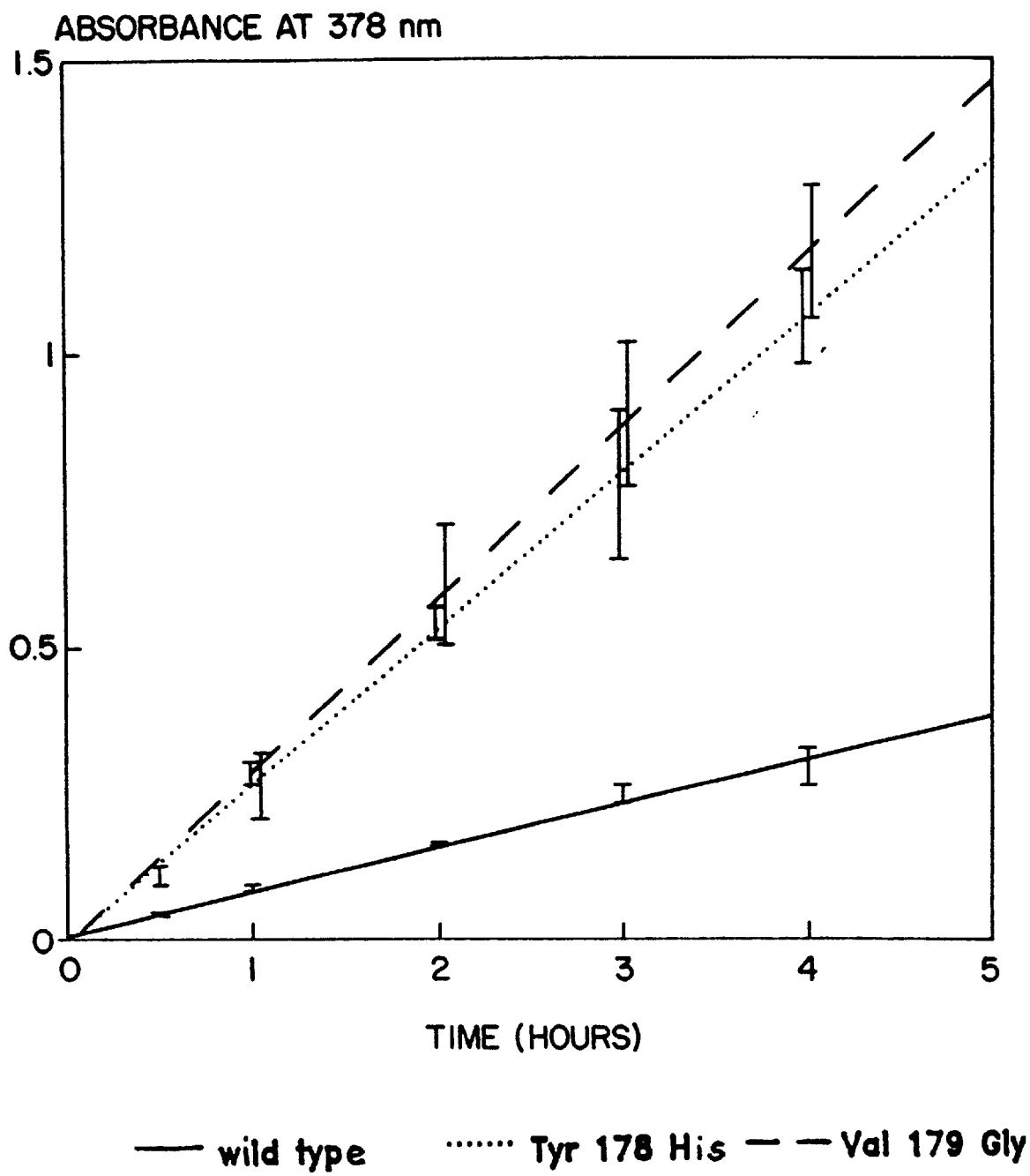
FIG. 20: conversion of adipyl serine by glutaryl acylase SY-77 wild-type and mutants Y178H and V179G. Enzymes were dosed in such a way that the same activity on glutaryl 7-ACA was obtained.
Figure 21:
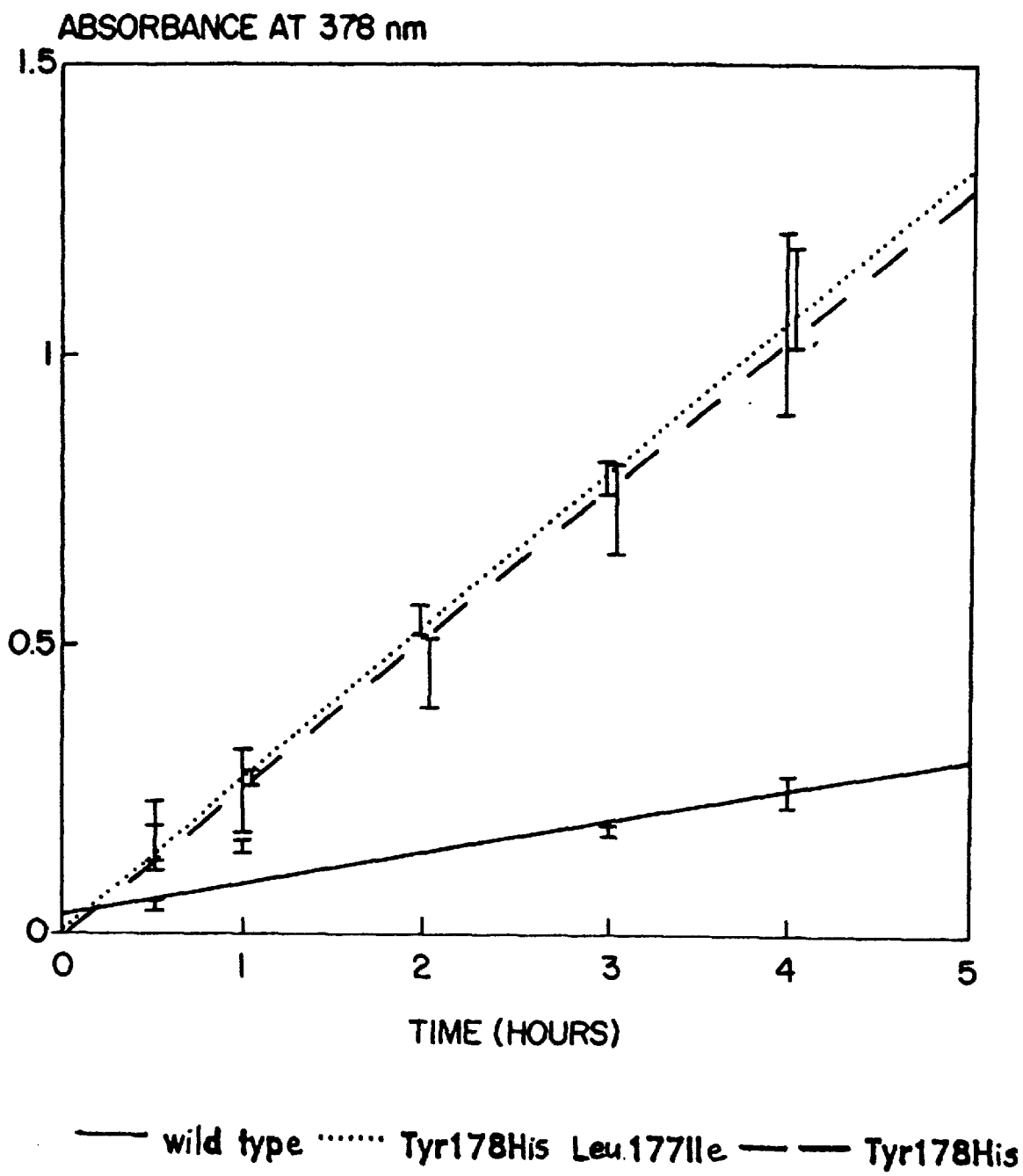
FIG. 21: conversion of adipyl serine by glutaryl acylase SY-77 wild-type and mutants Y178H and L177I+Y178H. Enzymes were dosed in such a way that the same activity on glutaryl 7-ACA was obtained.

Wild-type SY-77 glutaryl acylase and mutant SY-77 glutaryl acylases were assayed with glutaryl 7-ACA, glutaryl leucine and adipyl serine as substrates. Hydrolysis of the substrates was followed by measuring the release of 7-ACA, leucine or serine with fluorescamine at 378 nm. In the activity assays with glutaryl leucine and adipyl serine the mutants and the wild-type enzyme were dosed according to their activity on glutaryl 7-ACA. FIGS. 19–21 show the rate of hydrolysis with adipyl serine for the given mutants. The hydrolysis was followed in time by measuring the increase in absorption at 378 nm upon reaction of fluorescamine with the released serine. The mutants showed a 3 to 5 times higher activity on adipyl serine than the wild-type SY-77 glutaryl acylase. Since the wild-type grows very slowly when adipyl serine is the sole carbon source, it can be concluded that the SY-77 acylase mutants disclosed have a higher specificity on this substrate.

For glutaryl leucine the same assay procedure was followed as for adipyl serine in order to compare activity of mutants and wild-type. Glutaryl leucine is a suitable substrate to check whether mutations affect the specificity for the acyl side chain or for the complementary side, such as the β-lactam moiety or the amino acid. If mutations affect the specificity for the acyl side chain then the activity of

23 wild-type and mutant glutaryl acylase are likely to show the same tendency for substrates such as glutaryl 7-ACA and glutaryl leucine. Because in the assays enzymes are dosed according to their glutaryl 7-ACA activity this implicates that activities on glutaryl leucine should be very similar for mutants and wild-type. Indeed within the error of the measurement all mutants coincide with wild-type activity which indicates that the mutations affect the specificity for the acyl side chain, more specifically increase the specificity for the adipyl moiety.

EXAMPLE 11

Mutagenesis of Pseudomonas SE-83 Acylase

Region-directed and targeted random mutagenesis of pMcTSE5Nde was performed after creation of a gapped duplex molecule with the enzyme EcoRI. A "spiked" oligo covering amino acid positions 30 to 58 of SE-83 was used.

Targeted random (TRM) mutagenesis was carried out with the following oligonucleotide (SEQ ID NO:43):

AAG GCG GCTG NNN NNN GAC NNN GCC NNN CGC NNN ATA NNN ATC GGC CTC GCC

Another TRM mutagenesis was carried out on the region homologous to region 176–180 of SY-77 acylase. The mixed oligonucleotide (SEQ ID NO:44) used was as follows:

CCA GAG CTT GAA CCA GAC GGA NNN NNN NNN NNN NNN CAG CCG CCG CAT CAC GGC

A second gap was created with the enzymes NotI and SmaI. This gapped duplex was mutagenized with a spiked oligonucleotide covering amino acid positions 730 to 746 of SE-83. TRM mutagenesis was carried out with the following oligonucleotide (SEQ ID NO:45):

CAC CAT CGC GCA NNN GCT CCA NNN NNN ATT CTG GTC GGC NNN GTG GGG GCT GGC

Mutants were selected on aminoadipyl leucine or on aminoadipyl amide agar plates.

EXAMPLE 12

Mutagenesis of A. faecalis Acylase

In a pTZ18R subclone of the 4kb Sau3A-HpaI fragment of the pAF1 insert an NdeI site was constructed on the startcodon of the A. faecalis gene with the aid of the following oligonucleotide (SEQ ID NO:46):

G CCC TTT CTG CAT ATG TGT CCC TTA TTT TTA

After NdeI digestion of the resulting mutant plasmid pMaAFnde was constructed. After linearization with HI a gapped duplex with single stranded pMcAFNde was made. A spiked oligo covering region 37–46 was used for region mutagenesis and after transfer into E. coli WK6 Muts and subsequently E. coli HB101 the mutant library was selected on minimal plates with 10 μg/ml glutaryl leucine and 50 μg/ml cap. Those colonies which grew on these plates (and not on minimal plates) were tested for activity on glutaryl cephalosporin. A similar experiment with an oligo covering region 51–72 of A. faecalis was performed.

Targeted random mutagenesis (TRM) was performed on the same gapped duplex molecule using the following oligonucleotide (SEQ ID NO:47):

CAG ACG GTC TTG NNN NNN CGC NNN ACC NNN GCC

24

NNN ATA NNN GCC ATA GTG GCT

The use of this oligo results in a substitution of positions 51, 53, 55, 57, 59 and 60 into all possible amino acids. Another TRM was carried out on the region homologous to positions 176–180 of SY-77 acylase with the following mixed oligonucleotide (SEQ ID NO: 48):

TTC CAG ATT CGr GTC GGA NNN NNN NNN NNN NNN GGA GCC CAC CCA GAT CAT

A mutant library of $10^7$ mutants was generated and selected on aminoadipyl leucine or glutaryl leucine plates.

In another experiment a gapped duplex using NruI and MluI was made. This gapped duplex was mutagenized with a "spiked" oligonucleotide covering amino acid positions 761 to 790. The resulting mutant library was selected on glutaryl leucine and aminoadipyl leucine, respectively.

EXAMPLE 13

Mutagenesis of E. coli Acylase

The insert of plasmid pUNNEC1 was subcloned into vector pTZ18 using restriction sites HindIII and SmaI. With the following specific oligonucleotide (SEQ ID NO:49) an NdeI site was created at the start codon:

TCT ATT TTT CAT ATG ATC CTC TGG CAG

The acylase gene was then subcloned into plasmid pMaTECNde using the restriction enzymes NdeI and SmaI. This plasmid was mutagenized with a "spiked" oligonucleotide covering amino acids 53 to 74 of E. coli acylase and selected in a similar way as described in Example 9.

Targeted random mutagenesis of E. coli Pen-acylase was carried out with a mixed oligo homologous to the positions 176–180 of SY-77 acylase. The following oligo (SEQ ID NO: 50) was used:

TrC GCT AGT GCT ATC AGA NNN NNN NNN NNN NNN GGT GCC CAC AAA TAT CAT

All publications including patents and patent applications mentioned in this specification are indicative of the level of skill of those skilled in the art to which the invention pertains. All publications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

For example, it will be understood that selected mutants can be used for a consecutive round of mutagenesis with any of methods mentioned above or any of the mentioned spiked oligo's. Also a combination of two or more spiked oligo's in a single mutagenesis experiment is within the scope of this invention.

LIST OF REFERENCES

1. Lowe et al., Book Dev. Ind. Microbiol, 22, (1982) 163–180
2. Abbott B. J., Adv. Appl. Microb. 20 (1976), 203
3. Vandamme E. J., "Penicillin acylases and β-lactamases", In: "Microbial Enzymes and Bioconversions", E. H. Rose (Ed.), Economic Microbiology 5 (1980) 467–552, Acad. Press, New York
4. Ollson A. et al., Appl. Env. Microbiol. 49 (1985) 1084
5. Shibuya Y. et al., Agric. Biol. Chem. 45 (1981) 156–1567
6. Matsuda A. et al., J. Bacteriol. 169 (1987) 5815–5820
7. Walton R. B., Devel. Ind. Microbiol. 5 (1964) 349–353
8. Mahajan P. B., Appl. Biochem. Biotechnol. 9 (1984) 537–553
9. Mayer et al., Adv. Biotechnol. 1 (1982) 83–86
10. Schumacher et al., Nucleic Acids Res. 14 (1986) 5713–5727
11. Barbero J. L. et al., Gene 49 (1986) 69–80
12. Daumy G. O. et al., J. Bacteriol. 163 (1985) 1279–1281
13. Dickerson R. E. & Geis I. in "Hemoglobin", Ed. Benjamin and Cummings (1983), Menlo Park Calif., USA
14. Blow D., Nature 343 (1990) 694–695
15. Winkler F. K. et al., Nature 343 (1990) 771–774
16. Brady L. et al., Nature 343 (1990) 767–770
17. Maniatis et al., "Molecular Cloning, A Laboratory Manual", Cold Spring Harbor Laboratory, 1982/1989
18. Ausubel et al., "Current Protocols in Molecular Biology", John Wiley and Sons, Inc., New York, 1987
19. Perbal B., "A Practical Guide To Molecular Cloning", 2nd ed., John Wiley and Sons, Inc., New York, 1988
20. Nilsson et al., Nucleic Acids Res. 11 (1983) 8019
21. Reyes F. et al., J. Pharm. Pharmacol. 41 (1989) 136–137
22. Stanssens et al., Nucleic Acids Res. 17 (1989) 4441
23. De Boer et al., Proc. Natl. Acad. Sci. USA 80 (1983;) 21–25
24. Hermes et al., Gene 84 (1989) 143–151
25. Leethovaara et al., Protein Eng. 2 (1989) 143–151
26. Garcia et al., J. Biotech. 3 (1986) 187–195
27. Sang-Jin et al., Gene 56 (1987) 87–97
28. Meevootisom et al., Appl. Microbiol. Biotechnol., 25 (1987) 372–378
29. Matsuda A. et al., J. Bacteriol. 163 (1985) 1222–1228
30. Matsuda A. et al., J. Bacteriol. 169 (1987) 5821–5826
31. Bruns W. et al., J. Mol. Appl. Gen. 3 (1985) 36–44
32. Underfriend S. et al., Science 178 (1972) 871–872
33. Williams J. A. et al., J. Cell Biochem. 9B/supplement (1985) p. 99, no. 656
34. Forney L. J. et al., Appl. Environ. Microbiol. 55 (1989) 2550–2555
35. Forney L. J. et al., Appl. Environ. Microbiol. 55 (1989) 2556–2560
36. Leung D. W. et al., Technique 1 (1989) 11

We claim:

1. An isolated mutant microorganism Type II β-lactam acylase with altered substrate specificity, wherein said mutant acylase comprises:

an amino acid substitution at one or more selected sites in said acylase corresponding to an amino acid position selected from the group consisting of residues 60–64 and 177–180 of SY-77 acylase so that altered substrate specificity as compared to a wild-type Type II β-lactam acylase from the same species is obtained.

2. A method for acylation or deacylation of β-lactam said method comprising:

contacting said β-lactam with a mutant Type II β-lactam acylase according to claim 1 under conditions suitable for said acylation or deacylation to occur.

3. A β-lactam produced according to the method of claim 2.

4. The isolated mutant β-lactam acylase according to claim 1, wherein said acylase is obtained from a member of the group consisting of *Escherichia coli, Khiyvera citrophila, Alcaligenes faecalis*, and Pseudomonas.

5. The isolated mutant β-lactam arylase according to claim 1, wherein said acylase is obtained from *Alcaligenes faecalis strain ATCC* 19018.

6. The isolated mutant β-lactam acylase according to claim 1, wherein said acylase is obtained from Pseudomonas SE-83 AcyII or SY-77.

7. The isolated mutant β-lactam acylase according to claim 1, wherein said acylase has at least a mutation in one of more of the amino acid positions corresponding to 62, 177, 178 and 179 in Pseudomonas wild type SY-77.

8. A microorganism host strain transformed with an expression vector comprising a DNA sequence encoding a mutant β-lactam acylase according to claim 1, wherein said host strain is a Cephalosporium or a Penicillium.

9. An isolated mutant acylase according to claim 1, wherein said microorganism is a prokatyote.

10. A vector comprising a nucleic acid sequence encoding the mutant acylase of claim 1.

11. A host cell comprising the vector of claim 10.

12. A host cell that produces the mutant acylase of claim 1.

13. A method for obtaining a mutant acylase that comprises growing the host cell of claim 11 under conditions whereby said mutant acylase is produced.

14. A method for obtaining a mutant acylase that comprises growing the host cell of claim 12 under conditions whereby said mutant acylase is produced.

15. The method of claim 13 which further comprises isolating said mutant acylase.

16. The method of claim 14 which further comprises isolating said mutant acylase.

17. A method for obtaining a mutant microorganism Type II β-lactam acylase having an altered substrate specificity, said method comprising:

effecting a mutation in a gene encoding a Type-II β-lactam acylase to produce a mutated gene coding for a mutant β-lactam acylase having an amino acid substitution at one or more selected sites in said acylase corresponding to an amino acid position selected from the group consisting of residues 60–64 and 177–180 of SY-77 acylase, and isolating said mutant β-lactam acylase expressed by said mutated gene, wherein said mutant β-lactam acylase exhibits a desired activity change as compared to a wild-type β-lactam acylase from the same species.

18. A method for making a selected acylase mutant having a desired activity, said method comprising:

isolating said selected acylase mutant from a culture broth or cell lysate of a microorganism host strain transformed with a gene encoding a mutant β-lactam acylase according to claim 1.

19. The method of claim 1, wherein said mutant acylase has at least one desired activity change in substrate specificity in acylation or deacylation reactions as compared to a wild-type Type II β-lactam acylase from the same species.

20. The method according to claim 17, wherein said gene encoding said acylase is obtained from a member of the group consisting of *Escherichia coli, Kluyvera citrophila, Alcaligenes faecalis*, and Pseudomonas.

21. The method according to claim 20, wherein the *Alcaligenes faecalis* strain is ATCC 19018.

22. The method according to claim 20, wherein the Pseudomonas is SE-83 AcyII or SY-77.

23. The method according to claim 17, wherein at least a mutation is effected in one or more of the positions corresponding to 62, 177, 178 and 179 in Pseudomonas SY-77.

24. A method according to claim 17, wherein said microorganism is a prokaryote.

* * * * *

UNITED STATES PATENT AND TRADEMARK OFFICE
CERTIFICATE OF CORRECTION

PATENT NO. : 5,935,831
DATED : August 10, 1999
INVENTOR(S) : Quax et al.

Page 1 of 6

It is certified that error appears in the above-identified patent and that said Letters Patent is hereby corrected as shown below:

Title page,
Item [56], delete "Forney et al., *Applied & Environmental Microbiology*, (1989) 55:2550-2555.", and insert -- Forney et al., *Applied & Environmental Microbiology*, (1989) 55:2550-2555. --

Item [30], delete "Forney et al., *Applied & Environmental Microbiology*, (1989) 55:2556-2560." and insert -- Forney et al., *Applied & Environmental Microbiology*, (1989) 55:2556-2560. --

Item [56] delete Stanssens et al., *Nucleic Acids Research*, (1989) 12:4441-4454.", and insert -- Stanssens et al., *Nucleic Acids Research*, (1989) 17:4441-4454. --

Figure 1B:
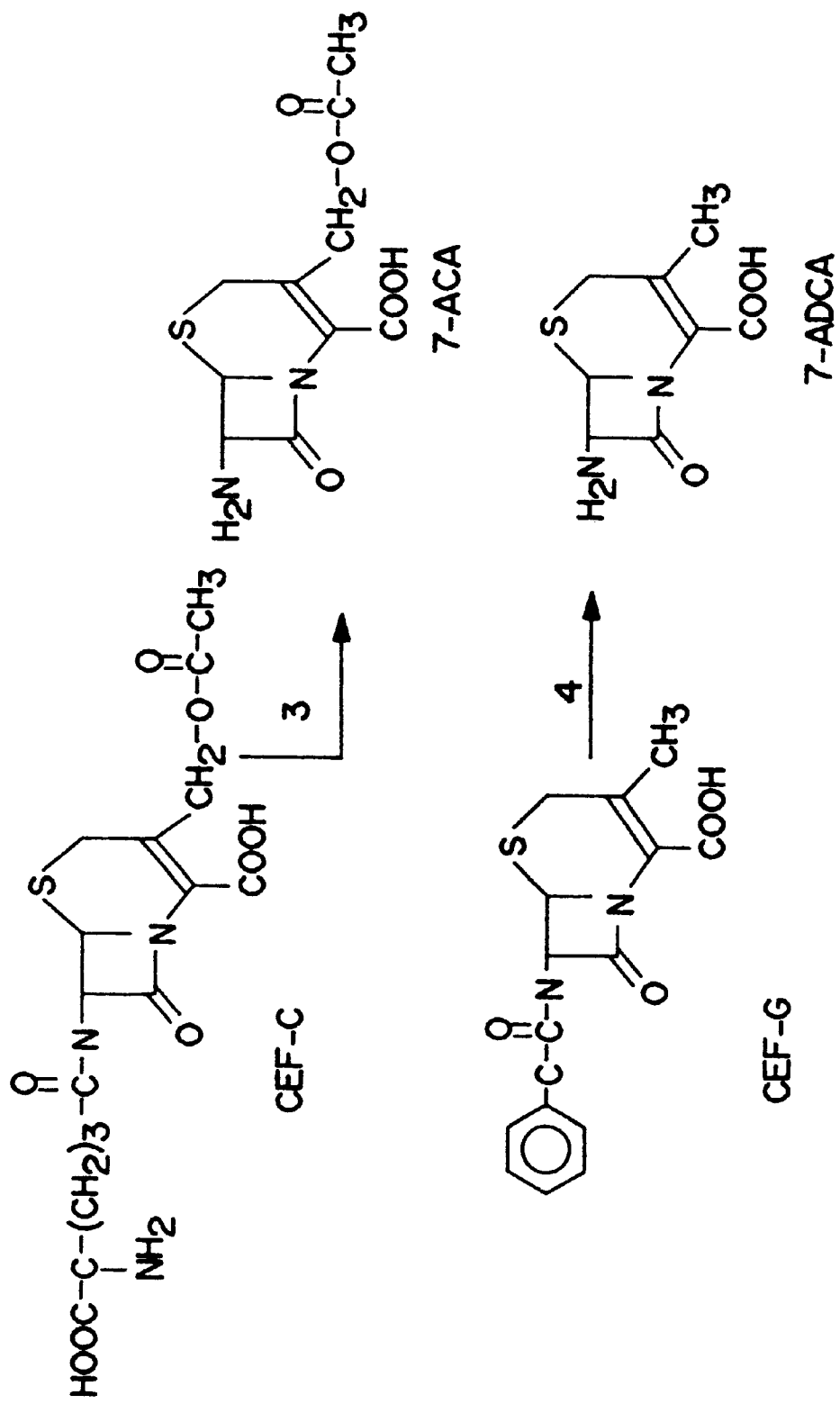
Figure 2:
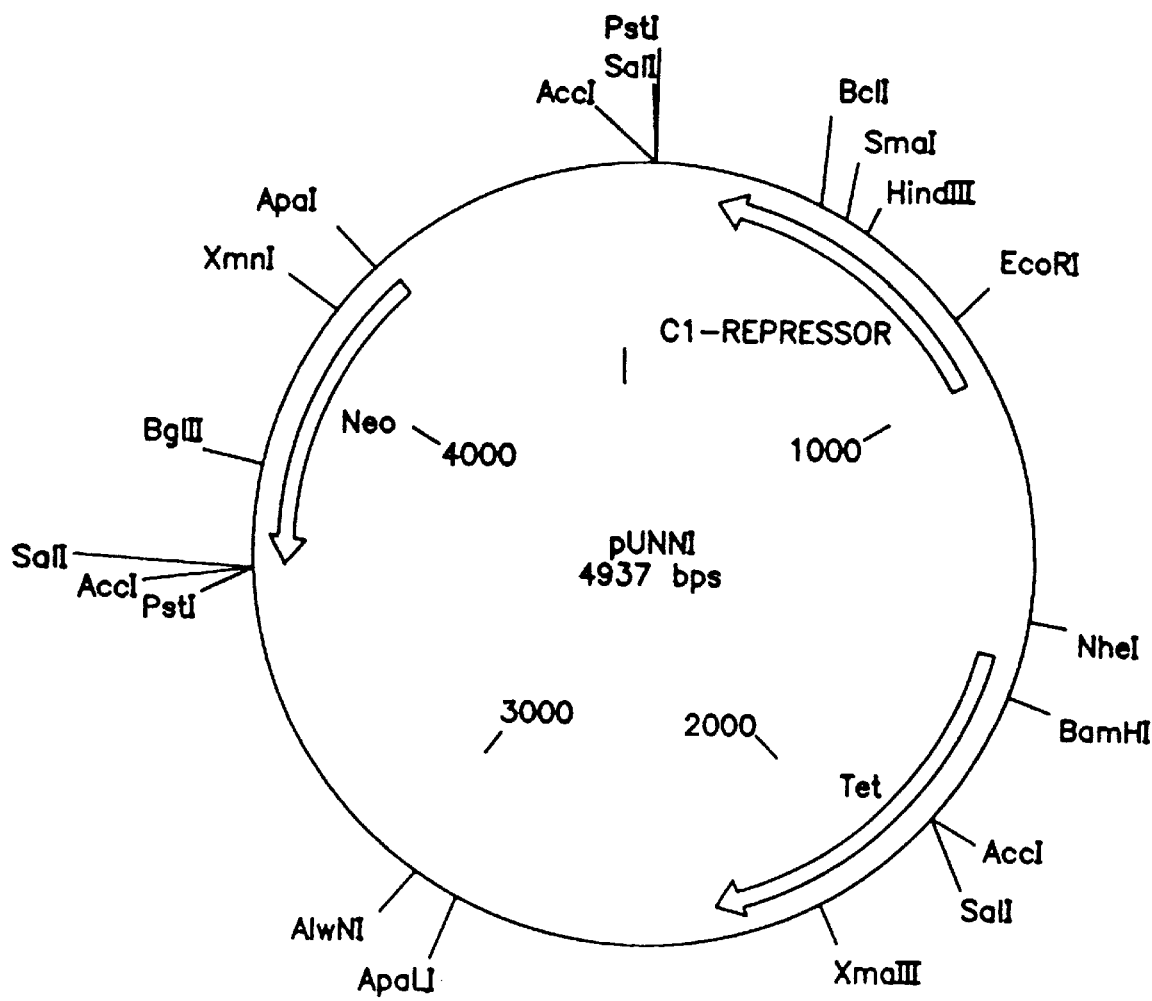
FIG. 2: restriction map of plasmid pUNNI.

Column 1,
Line 24, delete "P-lactam", and insert -- β-lactam --
Line 46, delete "FIG. 1", and insert -- FIGS. 1A-1B --

Column 2,
Line 11, delete "Pseudomonas" and insert -- *Pseudomonas* --
Line 44, delete "Pseudomonas" and insert -- *Pseudomonas* --
Lines 44-45, delete "Arthrobacter viscosus" and insert -- *Arthrobacter viscosus* --

Column 3,
Line 13, delete "*strain ATCC*" and insert -- strain ATCC --
Line 15, delete "Pseudomonas" and insert -- *Pseudomonas* --
Line 26, delete "(a)" and insert -- (α) --
Line 42, delete "plasmidin" and insert -- plasmid in --

Column 4,
Line 7, delete "Pseudomonas" and insert -- *Pseudomonas* --
Line 8, delete "Pseudomonas" and insert -- *Pseudomonas* --
Line 10, delete "specifity" and insert -- specificity --
Line 21, delete "(β-)aminoadipic" and insert -- (α-)aminoadipic --
Line 32, delete "Pseudomonas" and insert -- *Pseudomonas* --
Line 36, delete "Pseudomonas" and insert -- *Pseudomonas* --
Line 38, delete "Pseudomonas" and insert -- *Pseudomonas* --

UNITED STATES PATENT AND TRADEMARK OFFICE
CERTIFICATE OF CORRECTION

PATENT NO. : 5,935,831
DATED : August 10, 1999
INVENTOR(S) : Quax et al.

Page 2 of 6

It is certified that error appears in the above-identified patent and that said Letters Patent is hereby corrected as shown below:

Column 4, contd.
Line 51, delete "SEQ ID NO:4" and insert -- SEQ ID NO:1 --
Line 53, delete "Pseudomonas" and insert -- *Pseudomonas* --
Line 55, delete "*Kluvvera*" and insert -- *Kluyvera* --
Line 56, delete "(SEQ ID NO:7)" and insert -- (SEQ ID NO:6) --
Line 57, delete "Pseudomonas" and insert -- *Pseudomonas* --
Line 58, delete "Pseudomonas" and insert -- *Pseudomonas* --
Line 58, delete "(SY-77)" and insert -- (SY-77)(SEQ ID NO:2) --
Line 58, delete "asterix" and insert -- asterisk --

Column 5,
Line 49, delete "of -the" and insert -- of the --

Column 6,
Line 7, delete "Pseudomonas" and insert -- *Pseudomonas* --
Line 8, delete "Pseudomonas" and insert -- *Pseudomonas* --
Line 44, delete "Sofar" and insert -- So far --
Line 48, delete "Pseudomonas" and insert -- *Pseudomonas* --
Line 64, delete "Bacillus, Pseudomonas" and insert -- *Bacillus, Pseudomonas* --

Column 7,
Line 9, delete "In a is further" and insert -- In a further --

Column 8,
Line 6, delete "on DNA level-where" and insert -- on DNA level - where --
Line 10, delete "Alcalipenes" and insert -- *Alcaligenes* --
Line 28, delete "Pseudomonas" and insert -- *Pseudomonas* --
Line 29, delete "Pseudomonas" and insert -- *Pseudomonas* --
Line 32, delete "Pseudomonas" and insert -- *Pseudomonas* --
Line 35, delete "Pseudomonas" and insert -- *Pseudomonas* --
Line 37, delete "Pseudomonas" and insert -- *Pseudomonas* --
Line 45, delete "(Mahajan [8]" and insert -- (Mahajan [8], --

UNITED STATES PATENT AND TRADEMARK OFFICE
CERTIFICATE OF CORRECTION

PATENT NO. : 5,935,831
DATED : August 10, 1999
INVENTOR(S) : Quax et al.

It is certified that error appears in the above-identified patent and that said Letters Patent is hereby corrected as shown below:

Column 9,
Line 14, delete "Pseudomonas" (both occurrence) and insert -- *Pseudomonas* --
Line 18, delete "Pseudomonas" and insert -- *Pseudomonas* --
Line 19, delete "Pseudomonas" and insert -- *Pseudomonas* --
Line 22, delete "Pseudomonas" and insert -- *Pseudomonas* --
Line 42, delete "Cephalosporium and Penicillium" and insert -- *Cephalosporium* and *Penicillium* --
Line 59, delete "SnaBI and TaaI" and insert -- SnaBI and TagI --
Line 65, delete "KinI" and insert -- KpnI --
Line 67, delete "PUNNI" and insert -- pUNNI --

Column 10,
Line 13, delete "P-lactamase" and insert -- β-lactamase --
Line 39, delete "(Hermes [24]" and insert -- (Hermes [24]) --

Column 11,
Line 12, delete "(1$\mu$g/ml)$_1$" and insert -- (1$\mu$g/ml), --
Line 31, delete "upto" and insert -- up to --
Line 49, delete "(SEQ ID NO:8:" and insert -- (SEQ ID NO:8): --
Line 66, delete "Serratia marcescens" and insert *Serratia marcescens* --

Column 12,
Line 5, delete "Alcaligenes faecalis" and insert -- *Alcaligenes faecalis* --
Line 43, delete "Pseudomonas" and insert -- *Pseudomonas* --
Line 46, delete "Pseudomonas" and insert -- *Pseudomonas* --
Line 47, delete "HDAI and SmaI" and insert -- HpaI and SmaI --
Line 56, delete "Pseudomonas" and insert -- *Pseudomonas* --
Line 61, delete "plasmid is was" and insert -- plasmid was --
Line 65, delete "EmHI - SalI" and insert -- BamHI - SalI --

Column 13,
Line 1, delete "FIG." and insert -- FIGS. --
Line 12, delete "Pseudomonas" and insert -- *Pseudomonas* --
Line 16, delete "Pseudomonas" and insert -- *Pseudomonas* --

UNITED STATES PATENT AND TRADEMARK OFFICE
CERTIFICATE OF CORRECTION

PATENT NO. : 5,935,831
DATED : August 10, 1999
INVENTOR(S) : Quax et al.

It is certified that error appears in the above-identified patent and that said Letters Patent is hereby corrected as shown below:

Column 13, contd.
Line 17, delete "6.0 kb = II" and insert -- 6.0 kb BglII --
Line 18, delete "Pseudomonas" and insert -- *Pseudomonas* --
Line 22, delete "GG CCG" and insert -- CGG CCG --
Line 36, delete "*Kluvvera citroihila*" and insert -- *Kluyvera citrophila* --
Line 38, delete "Pseudomonas" and insert -- *Pseudomonas* --

Column 13, table 2,
Line 2, delete "H$_2$N-SNMVIG" and insert -- H$_2$N-SNMWVIG --
Line 3, delete "TOTA-COOH" and insert -- TQTA-COOH --

Column 14,
Line 65, delete "Pseudomonas" and insert -- *Pseudomonas* --

Column 15,
Line 30, delete "FIG. 14A-14E" and insert -- FIGS. 14A-14E --
Line 39, delete "enzym" and insert -- enzyme --
Line 63, delete "16A-16B" and insert -- 16A-16D --

Column 16,
Line 23, delete "Propensity" and insert -- propensity --
Line 29, delete "matagenesis" and insert -- mutagenesis --
Line 36, delete "FIG. 14A-14E" and insert -- FIGS. 14A-14E --

Column 17,
Line 30, delete "Type-IIb" and insert -- Type-IIB
Line 41, delete "type IIb" and insert -- Type-IIB --

Column 18,
Line 12, delete "hydrofobic" and insert -- hydrophobic --
Line 51, delete "oligonucleotide:" and insert -- oligonucleotide (SEQ ID NO: 29): --

Column 19,
Line 12, delete "suplemented" and insert -- supplemented --
Line 23, delete "occurence" and insert -- occurrence --
Line 54, delete "muts" and insert -- mutS --
Line 65, delete "30°C." and insert -- 30°C --

UNITED STATES PATENT AND TRADEMARK OFFICE
CERTIFICATE OF CORRECTION

PATENT NO. : 5,935,831
DATED : August 10, 1999
INVENTOR(S) : Quax et al.

It is certified that error appears in the above-identified patent and that said Letters Patent is hereby corrected as shown below:

Column 20,
Line 10, delete "CTC→ATC L1771" and insert -- CTC→ATC] [L1771 --
Line 11, delete "TAT→CAT Y178H" and insert -- TAT→CAT] [Y178H --
Line 25, delete "Targetted" and insert -- Targeted --

Column 21,
Line 25, delete "oligo-nucleotides" and insert -- oligonucleotides --

Column 23,
Line 22, delete "AAG GCG GCTG NNN" and insert -- AAG GCG GTC CTG NNN --
Line 47, delete "startcodon" and insert -- start codon --
Line 53, delete "HI" and insert -- BamHI --
Line 56, delete "Muts" and insert -- MutS --

Column 24,
Line 9, delete TTC CAG ATT CGr" and insert - TTC CAG ATT CGT --
Line 38, delete "TrC" and insert -- TTC --

Column 25,
Line 5, delete "156-1567" and insert -- 1561-1567 --
Last line, delete "alfa" and insert -- alpha --

Column 26,
Line 8, delete "(1983;)" and insert -- (1983) --

Column 79,
Line 30, delete "*Khiyvera*" and insert -- *Kluyvera* --
Line 31, delete "Pseudomonas" and insert -- *Pseudomonas* --
Line 32, delete "arylase" and insert -- acylase --
Line 34, delete "*strain ATCC*" and insert -- strain ATCC --
Line 36, delete "Pseudomonas" and insert -- *Pseudomonas* --

UNITED STATES PATENT AND TRADEMARK OFFICE
CERTIFICATE OF CORRECTION

PATENT NO. : 5,935,831
DATED : August 10, 1999
INVENTOR(S) : Quax et al.

It is certified that error appears in the above-identified patent and that said Letters Patent is hereby corrected as shown below:

Column 79, contd.
Lines 39-40, delete "has at least a mutation in one of more of the amino acid positions" and insert -- has at least a mutation in one or more of the amino acid positions --
Line 41, delete "Pseudomonas" and insert -- *Pseudomonas* --
Line 45, delete "Cephalosporium or a Penicillium" and insert -- *Cephalosporium* or a *Penicillium* --
Line 47, delete "prokatyote" and insert -- prokaryote --

Column 80,
Line 37, delete "claim 1" and insert -- claim 17 --
Line 44, delete "Pseudomonas" and insert -- *Pseudomonas* --
Line 48, delete "Pseudomonas" and insert -- *Pseudomonas* --
Line 51, delete "Pseudomonas" and insert -- *Pseudomonas* --

Signed and Sealed this

Nineteenth Day of February, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
          (A) LENGTH: 2163 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Pseudomonas species
          (B) STRAIN: SY77

(ix) FEATURE:
          (A) NAME/KEY: CDS
          (B) LOCATION: 1..2163
          (C) IDENTIFICATION METHOD: experimental
          (D) OTHER INFORMATION: /codon_start= 1
              /product= "Glutaryl-Cef acylase"
              /evidence= EXPERIMENTAL (ix) FEATURE:
          (A) NAME/KEY: sig_peptide
          (B) LOCATION: 1..87

(ix) FEATURE:
          (A) NAME/KEY: mat_peptide
          (B) LOCATION: 88..594
          (D) OTHER INFORMATION: /product= "glutaryl-cef acylase"
              /label= alfa-subunit -continued (ix) FEATURE:
    (A) NAME/KEY: mat_peptide
    (B) LOCATION: 595..2163
    (D) OTHER INFORMATION: /product= "glutaryl-cef acylase"
        /label= beta-subunit (xi) SEQUENCE DESCRIPTION: SEQ ID NO: 1:

```
ATG CTG AGA GTT CTG CAC CGG GCG GCG TCC GCC TTG GTT ATG GCG ACT           48
Met Leu Arg Val Leu His Arg Ala Ala Ser Ala Leu Val Met Ala Thr
-29         -25             -20             -15

GTG ATC GGC CTT GCG CCC GCC GTC GCC TTT GCG CTG GCC GAG CCG ACC           96
Val Ile Gly Leu Ala Pro Ala Val Ala Phe Ala Leu Ala Glu Pro Thr
            -10             -5               1

TCG ACG CCG CAG GCG CCG ATT GCG GCC TAT AAA CCG AGA AGC AAT GAG          144
Ser Thr Pro Gln Ala Pro Ile Ala Ala Tyr Lys Pro Arg Ser Asn Glu
    5                10              15

ATC CTG TGG GAC GGC TAC GGC GTC CCG CAC ATC TAC GGC GTC GAC GCG          192
Ile Leu Trp Asp Gly Tyr Gly Val Pro His Ile Tyr Gly Val Asp Ala
20              25              30              35

CCC TCA GCC TTC TAC GGC TAT GGC TGG GCC CAG GCG CGC AGC CAG GGC          240
Pro Ser Ala Phe Tyr Gly Tyr Gly Trp Ala Gln Ala Arg Ser Gln Gly
                40              45              50

GAC AAT ATC CTG CGC CTG TAT GGA GAA GCG CGG GGC AAG GGG GCC GAA          288
Asp Asn Ile Leu Arg Leu Tyr Gly Glu Ala Arg Gly Lys Gly Ala Glu
            55              60              65

TAC TGG GGC CCG GAT TAC GAA CAG ACG ACC GTC TGG CTG CTG ACC AAC          336
Tyr Trp Gly Pro Asp Tyr Glu Gln Thr Thr Val Trp Leu Leu Thr Asn
        70              75              80

GGC GTG CCG GAG CGC GCT CAG CAG TGG TAT GCG CAG CAG TCG CCT GAT          384
Gly Val Pro Glu Arg Ala Gln Gln Trp Tyr Ala Gln Gln Ser Pro Asp
85              90              95

TTC CGC GCC AAC CTC GAC GCC TTC GCG GCG GGC ATC AAC GCC TAT GCG          432
Phe Arg Ala Asn Leu Asp Ala Phe Ala Ala Gly Ile Asn Ala Tyr Ala
100             105             110             115

CAG CAG AAC CCC GAC GAC ATC TCG CCC GAC GTG CGG CAG GTG CTG CCG          480
Gln Gln Asn Pro Asp Asp Ile Ser Pro Asp Val Arg Gln Val Leu Pro
                120             125             130

GTT TCC GGC GCC GAC GTG GTG GCC CAC GCC CAC CGC CTG ATG AAC TTC          528
Val Ser Gly Ala Asp Val Val Ala His Ala His Arg Leu Met Asn Phe
            135             140             145

CTC TAT GTC GCG TCG CCC GGC CGC ACC CTG GGC GAG GGC GAC CCG CCG          576
Leu Tyr Val Ala Ser Pro Gly Arg Thr Leu Gly Glu Gly Asp Pro Pro
        150             155             160

GAC CTG GCC GAT CAA GGA TCC AAC TCC TGG GCG GTG GCG CCG GGA AAG          624
Asp Leu Ala Asp Gln Gly Ser Asn Ser Trp Ala Val Ala Pro Gly Lys
165             170             175

ACG GCG AAC GGG AAC GCC CTG CTG CTG CAG AAC CCG CAC CTG TCC TGG          672
Thr Ala Asn Gly Asn Ala Leu Leu Leu Gln Asn Pro His Leu Ser Trp
180             185             190             195

ACG ACG GAC TAC TTC ACC TAC TAC GAG GCG CAT CTC GTC ACG CCG GAC          720
Thr Thr Asp Tyr Phe Thr Tyr Tyr Glu Ala His Leu Val Thr Pro Asp
                200             205             210

TTC GAA ATC TAT GGC GCG ACC CAG ATC GGC CTG CCG GTC ATC CGC TTC          768
Phe Glu Ile Tyr Gly Ala Thr Gln Ile Gly Leu Pro Val Ile Arg Phe
            215             220             225

GCC TTC AAC CAG CGG ATG GGC ATC ACC AAT ACC GTC AAC GGC ATG GTG          816
Ala Phe Asn Gln Arg Met Gly Ile Thr Asn Thr Val Asn Gly Met Val
        230             235             240

GGG GCC ACC AAC TAT CGG CTG ACG CTT CAG GAC GGC GGC TAT CTG TAT          864
Gly Ala Thr Asn Tyr Arg Leu Thr Leu Gln Asp Gly Gly Tyr Leu Tyr
245             250             255
```

```
GAC GGT CAG GTG CGG CCG TTC GAG CGG CCT CAG GCC TCG TAT CGC CTG      912
Asp Gly Gln Val Arg Pro Phe Glu Arg Pro Gln Ala Ser Tyr Arg Leu
260             265             270             275

CGT CAG GCG GAC GGG ACG ACG GTC GAC AAG CCG TTG GAG ATC CGC TCC      960
Arg Gln Ala Asp Gly Thr Thr Val Asp Lys Pro Leu Glu Ile Arg Ser
            280             285             290

AGC GTC CAT GGC CCG GTC TTC GAG CGC GCG GAC GGC ACG GCC GTC GCC     1008
Ser Val His Gly Pro Val Phe Glu Arg Ala Asp Gly Thr Ala Val Ala
        295             300             305

GTT CGG GTC GCC GGT CTG GAC CGG CCG GGC ATG CTC GAG CAG TAT TTC     1056
Val Arg Val Ala Gly Leu Asp Arg Pro Gly Met Leu Glu Gln Tyr Phe
    310             315             320

GAC ATG ATC ACG GCG GAC AGC TTC GAC GAC TAC GAA GCC GCT TTG GCG     1104
Asp Met Ile Thr Ala Asp Ser Phe Asp Asp Tyr Glu Ala Ala Leu Ala
325             330             335

CGG ATG CAG GTG CCG ACC TTC AAC ATC GTC TAC GCC GAC CGC GAA GGG     1152
Arg Met Gln Val Pro Thr Phe Asn Ile Val Tyr Ala Asp Arg Glu Gly
340             345             350             355

ACC ATC AAC TAC AGC TTC AAC GGC GTG GCG CCC AAA CGG GCC GAG GGC     1200
Thr Ile Asn Tyr Ser Phe Asn Gly Val Ala Pro Lys Arg Ala Glu Gly
            360             365             370

GAC ATC GCC TTC TGG CAG GGG CTC GTG CCG GGC GAT TCC TCG CGT TAC     1248
Asp Ile Ala Phe Trp Gln Gly Leu Val Pro Gly Asp Ser Ser Arg Tyr
        375             380             385

CTG TGG ACC GAG ACA CAC CCG CTG GAC GAT CTG CCG CGC GTC ACC AAT     1296
Leu Trp Thr Glu Thr His Pro Leu Asp Asp Leu Pro Arg Val Thr Asn
    390             395             400

CCG CCG GGC GGC TTC GTG CAG AAC TCC AAT GAT CCG CCG TGG ACG CCG     1344
Pro Pro Gly Gly Phe Val Gln Asn Ser Asn Asp Pro Pro Trp Thr Pro
405             410             415

ACC TGG CCC GTC ACC TAC ACG CCC AAG GAC TTC CCC TCC TAT CTG GCG     1392
Thr Trp Pro Val Thr Tyr Thr Pro Lys Asp Phe Pro Ser Tyr Leu Ala
420             425             430             435

CCC CAG ACG CCG CAT TCC CTG CGT GCG CAA CAA AGC GTG CGT CTG ATG     1440
Pro Gln Thr Pro His Ser Leu Arg Ala Gln Gln Ser Val Arg Leu Met
            440             445             450

TCC GAG AAC GAC GAC CTG ACG CTG GAG CGC TTC ATG GCG CTG CAG TTG     1488
Ser Glu Asn Asp Asp Leu Thr Leu Glu Arg Phe Met Ala Leu Gln Leu
        455             460             465

AGC CAT CGC GCC GTC ATG GCC GAC CGC ACC TTG CCG GAC CTG ATC CCG     1536
Ser His Arg Ala Val Met Ala Asp Arg Thr Leu Pro Asp Leu Ile Pro
    470             475             480

GCC GCC CTG ATC GAC CCC GAT CCC GAG GTC CAG GCG GCG GCG CGC CTG     1584
Ala Ala Leu Ile Asp Pro Asp Pro Glu Val Gln Ala Ala Ala Arg Leu
485             490             495

CTG GCG GCG TGG GAT CGC GAG TTC ACC AGC GAC AGC CGC GCC GCC CTG     1632
Leu Ala Ala Trp Asp Arg Glu Phe Thr Ser Asp Ser Arg Ala Ala Leu
500             505             510             515

CTG TTC GAG GAA TGG GCG CGT CTG TTC GCC GGC CAG AAT TTC GCA GGC     1680
Leu Phe Glu Glu Trp Ala Arg Leu Phe Ala Gly Gln Asn Phe Ala Gly
            520             525             530

CAG GCC GGC TTC GCC ACG CCC TGG TCG CTG GAT AAG CCG GTC AGC ACG     1728
Gln Ala Gly Phe Ala Thr Pro Trp Ser Leu Asp Lys Pro Val Ser Thr
        535             540             545

CCT TAC GGC GTC CGC GAC CCC AAG GCC GCC GTC GAT CAA CTG CGG ACC     1776
Pro Tyr Gly Val Arg Asp Pro Lys Ala Ala Val Asp Gln Leu Arg Thr
    550             555             560

GCC ATC GCC AAC ACC AAG CGC AAA TAC GGC GCG ATC GAC CGG CCG TTC     1824
Ala Ile Ala Asn Thr Lys Arg Lys Tyr Gly Ala Ile Asp Arg Pro Phe
565             570             575
```

|   |   |   |   |   |   |   |   |   |   |   |   |   |   |   |   |      |
|---|---|---|---|---|---|---|---|---|---|---|---|---|---|---|---|------|
| GGC | GAC | GCC | TCG | CGC | ATG | ATC | CTG | AAC | GAC | GTG | AAT | GTT | CCG | GGC | GCC | 1872 |
| Gly | Asp | Ala | Ser | Arg | Met | Ile | Leu | Asn | Asp | Val | Asn | Val | Pro | Gly | Ala |      |
| 580 |     |     |     | 585 |     |     |     |     | 590 |     |     |     |     | 595 |     |      |
| GCC | GGC | TAC | GGC | AAC | CTG | GGT | TCC | TTC | CGG | GTC | TTC | ACC | TGG | TCC | GAT | 1920 |
| Ala | Gly | Tyr | Gly | Asn | Leu | Gly | Ser | Phe | Arg | Val | Phe | Thr | Trp | Ser | Asp |      |
|     |     |     | 600 |     |     |     |     | 605 |     |     |     |     | 610 |     |     |      |
| CCT | GAC | GAA | AAC | GGG | GTT | CGC | ACG | CCC | GTC | CAC | GGC | GAG | ACG | TGG | GTG | 1968 |
| Pro | Asp | Glu | Asn | Gly | Val | Arg | Thr | Pro | Val | His | Gly | Glu | Thr | Trp | Val |      |
|     |     |     | 615 |     |     |     |     | 620 |     |     |     |     | 625 |     |     |      |
| GCG | ATG | ATC | GAG | TTC | TCC | ACG | CCG | GTG | CGG | GCC | TAT | GGC | CTG | ATG | AGC | 2016 |
| Ala | Met | Ile | Glu | Phe | Ser | Thr | Pro | Val | Arg | Ala | Tyr | Gly | Leu | Met | Ser |      |
|     |     | 630 |     |     |     |     | 635 |     |     |     |     | 640 |     |     |     |      |
| TAC | GGC | AAC | TCT | CGC | CAG | CCG | GGC | ACG | ACG | CAC | TAC | AGC | GAT | CAG | ATC | 2064 |
| Tyr | Gly | Asn | Ser | Arg | Gln | Pro | Gly | Thr | Thr | His | Tyr | Ser | Asp | Gln | Ile |      |
| 645 |     |     |     |     | 650 |     |     |     |     | 655 |     |     |     |     |     |      |
| GAA | CGC | GTG | TCG | CGC | GCC | GAC | TTC | CGC | GAA | CTG | TTG | CTG | CGG | CGA | GAG | 2112 |
| Glu | Arg | Val | Ser | Arg | Ala | Asp | Phe | Arg | Glu | Leu | Leu | Leu | Arg | Arg | Glu |      |
| 660 |     |     |     | 665 |     |     |     |     | 670 |     |     |     |     | 675 |     |      |
| CAG | GTC | GAG | GCC | GCC | GTC | CAG | GAA | CGC | ACG | CCC | TTC | AAC | TTC | AAG | CCA | 2160 |
| Gln | Val | Glu | Ala | Ala | Val | Gln | Glu | Arg | Thr | Pro | Phe | Asn | Phe | Lys | Pro |      |
|     |     |     |     | 680 |     |     |     |     | 685 |     |     |     |     | 690 |     |      |
| TGA |     |     |     |     |     |     |     |     |     |     |     |     |     |     |     | 2163 |

(2) INFORMATION FOR SEQ ID NO: 2:

(i) SEQUENCE CHARACTERISTICS:
        (A) LENGTH: 720 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Arg Val Leu His Arg Ala Ala Ser Ala Leu Val Met Ala Thr
-29              -25                 -20                 -15

Val Ile Gly Leu Ala Pro Ala Val Ala Phe Ala Leu Ala Glu Pro Thr
                -10                  -5                   1

Ser Thr Pro Gln Ala Pro Ile Ala Ala Tyr Lys Pro Arg Ser Asn Glu
      5                  10                 15

Ile Leu Trp Asp Gly Tyr Gly Val Pro His Ile Tyr Gly Val Asp Ala
 20                  25                 30                  35

Pro Ser Ala Phe Tyr Gly Tyr Gly Trp Ala Gln Ala Arg Ser Gln Gly
                 40                  45                  50

Asp Asn Ile Leu Arg Leu Tyr Gly Glu Ala Arg Gly Lys Gly Ala Glu
                 55                  60                  65

Tyr Trp Gly Pro Asp Tyr Glu Gln Thr Thr Val Trp Leu Leu Thr Asn
            70                  75                  80

Gly Val Pro Glu Arg Ala Gln Gln Trp Tyr Ala Gln Gln Ser Pro Asp
 85                  90                  95

Phe Arg Ala Asn Leu Asp Ala Phe Ala Ala Gly Ile Asn Ala Tyr Ala
100                 105                 110                 115

Gln Gln Asn Pro Asp Asp Ile Ser Pro Asp Val Arg Gln Val Leu Pro
                120                 125                 130

Val Ser Gly Ala Asp Val Val Ala His Ala His Arg Leu Met Asn Phe
                135                 140                 145

Leu Tyr Val Ala Ser Pro Gly Arg Thr Leu Gly Glu Gly Asp Pro Pro
                150                 155                 160

Asp Leu Ala Asp Gln Gly Ser Asn Ser Trp Ala Val Ala Pro Gly Lys
165                 170                 175
```

-continued

Thr Ala Asn Gly Asn Ala Leu Leu Leu Gln Asn Pro His Leu Ser Trp
180                 185                 190                 195

Thr Thr Asp Tyr Phe Thr Tyr Tyr Glu Ala His Leu Val Thr Pro Asp
            200                 205                 210

Phe Glu Ile Tyr Gly Ala Thr Gln Ile Gly Leu Pro Val Ile Arg Phe
            215                 220                 225

Ala Phe Asn Gln Arg Met Gly Ile Thr Asn Thr Val Asn Gly Met Val
        230                 235                 240

Gly Ala Thr Asn Tyr Arg Leu Thr Leu Gln Asp Gly Gly Tyr Leu Tyr
        245                 250                 255

Asp Gly Gln Val Arg Pro Phe Glu Arg Pro Gln Ala Ser Tyr Arg Leu
260                 265                 270                 275

Arg Gln Ala Asp Gly Thr Thr Val Asp Lys Pro Leu Glu Ile Arg Ser
                280                 285                 290

Ser Val His Gly Pro Val Phe Glu Arg Ala Asp Gly Thr Ala Val Ala
            295                 300                 305

Val Arg Val Ala Gly Leu Asp Arg Pro Gly Met Leu Glu Gln Tyr Phe
        310                 315                 320

Asp Met Ile Thr Ala Asp Ser Phe Asp Tyr Glu Ala Ala Leu Ala
325                 330                 335

Arg Met Gln Val Pro Thr Phe Asn Ile Val Tyr Ala Asp Arg Glu Gly
340                 345                 350                 355

Thr Ile Asn Tyr Ser Phe Asn Gly Val Ala Pro Lys Arg Ala Glu Gly
                360                 365                 370

Asp Ile Ala Phe Trp Gln Gly Leu Val Pro Gly Asp Ser Ser Arg Tyr
            375                 380                 385

Leu Trp Thr Glu Thr His Pro Leu Asp Asp Leu Pro Arg Val Thr Asn
        390                 395                 400

Pro Pro Gly Gly Phe Val Gln Asn Ser Asn Asp Pro Pro Trp Thr Pro
        405                 410                 415

Thr Trp Pro Val Thr Tyr Thr Pro Lys Asp Phe Pro Ser Tyr Leu Ala
420                 425                 430                 435

Pro Gln Thr Pro His Ser Leu Arg Ala Gln Gln Ser Val Arg Leu Met
                440                 445                 450

Ser Glu Asn Asp Asp Leu Thr Leu Glu Arg Phe Met Ala Leu Gln Leu
            455                 460                 465

Ser His Arg Ala Val Met Ala Asp Arg Thr Leu Pro Asp Leu Ile Pro
        470                 475                 480

Ala Ala Leu Ile Asp Pro Asp Pro Glu Val Gln Ala Ala Arg Leu
485                 490                 495

Leu Ala Ala Trp Asp Arg Glu Phe Thr Ser Asp Ser Arg Ala Ala Leu
500                 505                 510                 515

Leu Phe Glu Glu Trp Ala Arg Leu Phe Ala Gly Gln Asn Phe Ala Gly
            520                 525                 530

Gln Ala Gly Phe Ala Thr Pro Trp Ser Leu Asp Lys Pro Val Ser Thr
        535                 540                 545

Pro Tyr Gly Val Arg Asp Pro Lys Ala Ala Val Asp Gln Leu Arg Thr
550                 555                 560

Ala Ile Ala Asn Thr Lys Arg Lys Tyr Gly Ala Ile Asp Arg Pro Phe
565                 570                 575

Gly Asp Ala Ser Arg Met Ile Leu Asn Asp Val Asn Val Pro Gly Ala
580                 585                 590                 595

```
Ala Gly Tyr Gly Asn Leu Gly Ser Phe Arg Val Phe Thr Trp Ser Asp
            600                 605                 610

Pro Asp Glu Asn Gly Val Arg Thr Pro Val His Gly Glu Thr Trp Val
        615                 620                 625

Ala Met Ile Glu Phe Ser Thr Pro Val Arg Ala Tyr Gly Leu Met Ser
            630                 635                 640

Tyr Gly Asn Ser Arg Gln Pro Gly Thr Thr His Tyr Ser Asp Gln Ile
    645                 650                 655

Glu Arg Val Ser Arg Ala Asp Phe Arg Glu Leu Leu Arg Arg Glu
660             665                 670                 675

Gln Val Glu Ala Ala Val Gln Glu Arg Thr Pro Phe Asn Phe Lys Pro
            680                 685                 690
```

(2) INFORMATION FOR SEQ ID NO: 3:

(i) SEQUENCE CHARACTERISTICS:
        (A) LENGTH: 2451 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Alcaligenes faecalis
        (B) STRAIN: ATCC 19018 (=NCTC415)
        (I) ORGANELLE: Chloroplast (ix) FEATURE:
        (A) NAME/KEY: CDS
        (B) LOCATION: 1..2451

(ix) FEATURE:
        (A) NAME/KEY: sig_peptide
        (B) LOCATION: 1..78
        (C) IDENTIFICATION METHOD: experimental
        (D) OTHER INFORMATION: /product= "penicillin acylase"
            /evidence= EXPERIMENTAL (ix) FEATURE:
        (A) NAME/KEY: mat_peptide
        (B) LOCATION: 79..708
        (D) OTHER INFORMATION: /product= "penicillin acylase"
            /label= alpha-subunit (ix) FEATURE:
        (A) NAME/KEY: mat_peptide
        (B) LOCATION: 709..2448
        (C) IDENTIFICATION METHOD: experimental
        (D) OTHER INFORMATION: /product= "penicillin acylase"
            /evidence= EXPERIMENTAL
            /label= beta-subunit (xi) SEQUENCE DESCRIPTION: SEQ ID NO: 3:

```
ATG CAG AAA GGG CTT GTT CGT ACC GGG CTT GTG GCC GCT GGT TTG ATC      48
Met Gln Lys Gly Leu Val Arg Thr Gly Leu Val Ala Ala Gly Leu Ile
-26 -25                 -20                 -15

TTG GGT TGG GCG GGG GCA CCG ACC CAC GCG CAA GTG CAG TCG GTA GAG      96
Leu Gly Trp Ala Gly Ala Pro Thr His Ala Gln Val Gln Ser Val Glu
-10             -5                  1                   5

GTG ATG CGG GAC AGT TAT GGC GTG CCG CAC GTC TTT GCC GAC AGC CAC     144
Val Met Arg Asp Ser Tyr Gly Val Pro His Val Phe Ala Asp Ser His
                10                  15                  20

TAT GGC TTG TAT TAC GGC TAT GGT TAT GCG GTC GCC CAA GAC CGT CTG     192
Tyr Gly Leu Tyr Tyr Gly Tyr Gly Tyr Ala Val Ala Gln Asp Arg Leu
            25                  30                  35
```

```
TTC CAG ATG GAC ATG GCG CGT CGC TCC TTT GTC GGC ACA ACC GCC GCC      240
Phe Gln Met Asp Met Ala Arg Arg Ser Phe Val Gly Thr Thr Ala Ala
    40                  45                  50

GTC TTA GGC CCT GGT GAG CAA GAT GCC TAC GTC AAG TAC GAC ATG CAG      288
Val Leu Gly Pro Gly Glu Gln Asp Ala Tyr Val Lys Tyr Asp Met Gln
55                  60                  65                  70

GTG CGG CAG AAC TTC ACC CCG GCT TCC ATA CAG CGG CAG ATC GCG GCC      336
Val Arg Gln Asn Phe Thr Pro Ala Ser Ile Gln Arg Gln Ile Ala Ala
                75                  80                  85

TTG TCC AAG GAT GAG CGC GAT ATT TTT CGT GGC TAT GCC GAT GGC TAT      384
Leu Ser Lys Asp Glu Arg Asp Ile Phe Arg Gly Tyr Ala Asp Gly Tyr
            90                  95                  100

AAC GCC TAT CTG GAG CAG GTG CGG CGT CGC CCT GAG TTG CTG CCC AAA      432
Asn Ala Tyr Leu Glu Gln Val Arg Arg Arg Pro Glu Leu Leu Pro Lys
        105                 110                 115

GAA TAT GTG GAT TTT GAT TTC CAG CCC GAG CCG CTG ACC GAC TTT GAT      480
Glu Tyr Val Asp Phe Asp Phe Gln Pro Glu Pro Leu Thr Asp Phe Asp
    120                 125                 130

GTG GTC ATG ATC TGG GTG GGC TCC ATG GCC AAT CGC TTC TCC GAC ACG      528
Val Val Met Ile Trp Val Gly Ser Met Ala Asn Arg Phe Ser Asp Thr
135                 140                 145                 150

AAT CTG GAA GTG ACG GCA CTG GCC ATG CGT CAG TCT CTG GAG AAA CAG      576
Asn Leu Glu Val Thr Ala Leu Ala Met Arg Gln Ser Leu Glu Lys Gln
                155                 160                 165

CAC GGC CCG GAA CGA GGC CGT GCC TTG TTT GAT GAG CTG CTG TGG ATC      624
His Gly Pro Glu Arg Gly Arg Ala Leu Phe Asp Glu Leu Leu Trp Ile
            170                 175                 180

AAT GAC ACA ACA GCT CCC ACT ACG GTT CCG GCC CCC GCT GCC GAG CAC      672
Asn Asp Thr Thr Ala Pro Thr Thr Val Pro Ala Pro Ala Ala Glu His
        185                 190                 195

AAG CCG CAG GCA CAA GCA GGG ACG CAG GAT CTG GCT CAT GTT TCC TCG      720
Lys Pro Gln Ala Gln Ala Gly Thr Gln Asp Leu Ala His Val Ser Ser
    200                 205                 210

CCA GTA CTG GCT ACC GAG CTA GAG CGC CAG GAC AAG CAC TGG GGC GGC      768
Pro Val Leu Ala Thr Glu Leu Glu Arg Gln Asp Lys His Trp Gly Gly
215                 220                 225                 230

CGT GGC CCG GAC TTC GCG CCC AAG GCT AGC AAC CTG TGG AGC ACT CGC      816
Arg Gly Pro Asp Phe Ala Pro Lys Ala Ser Asn Leu Trp Ser Thr Arg
                235                 240                 245

CCC GAG CGA GTG CAG GAG GGC TCG ACC GTA CTG ATC AAC GGC CCA CAG      864
Pro Glu Arg Val Gln Glu Gly Ser Thr Val Leu Ile Asn Gly Pro Gln
            250                 255                 260

TTT GGC TGG TAC AAC CCG GCC TAC ACC TAT GGC ATT GGC TTG CAT GGC      912
Phe Gly Trp Tyr Asn Pro Ala Tyr Thr Tyr Gly Ile Gly Leu His Gly
        265                 270                 275

GCC GGC TTC GAT GTG GTG GGT AAT ACG CCT TTT GCC TAT CCG ATC GTA      960
Ala Gly Phe Asp Val Val Gly Asn Thr Pro Phe Ala Tyr Pro Ile Val
    280                 285                 290

CTG TTT GGC ACC AAT AGC GAG ATT GCC TGG GGG GCG ACT GCT GGC CCG     1008
Leu Phe Gly Thr Asn Ser Glu Ile Ala Trp Gly Ala Thr Ala Gly Pro
295                 300                 305                 310

CAA GAT GTG GTG GAC ATA TAT CAG GAA AAA TTG AAC CCC TCG CGT GCC     1056
Gln Asp Val Val Asp Ile Tyr Gln Glu Lys Leu Asn Pro Ser Arg Ala
                315                 320                 325

GAT CAG TAC TGG TTC AAC AAT GCC TGG CGC ACG ATG GAG CAG CGC AAG     1104
Asp Gln Tyr Trp Phe Asn Asn Ala Trp Arg Thr Met Glu Gln Arg Lys
            330                 335                 340

GAA CGT ATC CAG GTA CGC GGT CAG GCT GAT CGG GAA ATG ACG ATC TGG     1152
Glu Arg Ile Gln Val Arg Gly Gln Ala Asp Arg Glu Met Thr Ile Trp
        345                 350                 355
```

```
CGC ACC GTG CAC GGC CCT GTG ATG CAG TTT GAT TAC GAT CAG GGC GCG     1200
Arg Thr Val His Gly Pro Val Met Gln Phe Asp Tyr Asp Gln Gly Ala
    360                 365                 370

GCG TAC AGC AAG AAA CGC AGC TGG GAT GGC TAT GAG GTG CAG TCC TTG     1248
Ala Tyr Ser Lys Lys Arg Ser Trp Asp Gly Tyr Glu Val Gln Ser Leu
375                 380                 385                 390

CTA GCC TGG TTG AAC GTG GCC AAG GCC CGC AAC TGG ACG GAG TTT CTG     1296
Leu Ala Trp Leu Asn Val Ala Lys Ala Arg Asn Trp Thr Glu Phe Leu
                395                 400                 405

GAT CAA GCC AGC AAG ATG GCG ATT TCG ATC AAC TGG TAC TAC GCC GAC     1344
Asp Gln Ala Ser Lys Met Ala Ile Ser Ile Asn Trp Tyr Tyr Ala Asp
            410                 415                 420

AAG CAC GGC AAT ATT GGT TAT GTC TCG CCG GCC TTC CTG CCC CAG CGT     1392
Lys His Gly Asn Ile Gly Tyr Val Ser Pro Ala Phe Leu Pro Gln Arg
                425                 430                 435

CCT GCC GAT CAG GAC ATC CGT GTC CCT GCC AAG GGG GAT GGC AGC ATG     1440
Pro Ala Asp Gln Asp Ile Arg Val Pro Ala Lys Gly Asp Gly Ser Met
    440                 445                 450

GAG TGG CTG GGC ATC AAG AGT TTC GAC GCG ATT CCC AAA GCC TAC AAT     1488
Glu Trp Leu Gly Ile Lys Ser Phe Asp Ala Ile Pro Lys Ala Tyr Asn
455                 460                 465                 470

CCA CCC CAG GGC TAT CTG GTC AAC TGG AAC AAC AAG CCT GCG CCG GAC     1536
Pro Pro Gln Gly Tyr Leu Val Asn Trp Asn Asn Lys Pro Ala Pro Asp
                475                 480                 485

AAA ACC AAT ACG GAT ACT TAC TAT TGG ACC TAT GGC GAC CGC ATG AAT     1584
Lys Thr Asn Thr Asp Thr Tyr Tyr Trp Thr Tyr Gly Asp Arg Met Asn
            490                 495                 500

GAA CTG GTC AGT CAG TAC CAG CAG AAA GAC CTC TTC AGT GTG CAG GAG     1632
Glu Leu Val Ser Gln Tyr Gln Gln Lys Asp Leu Phe Ser Val Gln Glu
    505                 510                 515

ATC TGG GAG TTC AAT CAA AAA GCC TCC TAT AGC GAT GTG AAC TGG CGC     1680
Ile Trp Glu Phe Asn Gln Lys Ala Ser Tyr Ser Asp Val Asn Trp Arg
520                 525                 530

TAC TTC CGC CCA CAT CTG GAA AAG CTG GCG CAA CAG CTG CCG GCC GAC     1728
Tyr Phe Arg Pro His Leu Glu Lys Leu Ala Gln Gln Leu Pro Ala Asp
535                 540                 545                 550

GAT AGC AGC AAG GCG GCG CTG ACG ATG TTG CTC GCC TGG GAT GGA ATG     1776
Asp Ser Ser Lys Ala Ala Leu Thr Met Leu Leu Ala Trp Asp Gly Met
                555                 560                 565

GAA CAG GAT CAG GGA GGG CAA AAT GCC GGA CCG GCG CGG GTG CTC TTC     1824
Glu Gln Asp Gln Gly Gly Gln Asn Ala Gly Pro Ala Arg Val Leu Phe
            570                 575                 580

AAG ACC TGG CTG GAA GAA ATG TAC AAG CAG GTC TTG ATG CCG GTG GTG     1872
Lys Thr Trp Leu Glu Glu Met Tyr Lys Gln Val Leu Met Pro Val Val
    585                 590                 595

CCT GAA TCG CAT CGC GCC ATG TAT AGC CAG ACT GGT TTT GCC ACG CAG     1920
Pro Glu Ser His Arg Ala Met Tyr Ser Gln Thr Gly Phe Ala Thr Gln
600                 605                 610

CAA GGT CCC AAC CCC GGT TCC ATC AAC TTG AGC ATG GGC ACC AAG GTC     1968
Gln Gly Pro Asn Pro Gly Ser Ile Asn Leu Ser Met Gly Thr Lys Val
615                 620                 625                 630

TTG TTG CGT GCC TTG GTG CTG GAA GCC CAT CCC GAT CCC AAG CGT GTG     2016
Leu Leu Arg Ala Leu Val Leu Glu Ala His Pro Asp Pro Lys Arg Val
                635                 640                 645

AAT GTC TTT GGT GAG CGT TCG TCT CAG GAA ATC ATG CAC ACA GCT TTG     2064
Asn Val Phe Gly Glu Arg Ser Ser Gln Glu Ile Met His Thr Ala Leu
            650                 655                 660

CAA AAT GCG CAG GCC CGC TTG AGC CAG GAG CAG GGC GCT CAG ATG GCG     2112
Gln Asn Ala Gln Ala Arg Leu Ser Gln Glu Gln Gly Ala Gln Met Ala
    665                 670                 675
```

```
CGC TGG ACC ATG CCG ACC TCC GTG CAT CGT TTC AGC GAC AAG AAC TTC     2160
Arg Trp Thr Met Pro Thr Ser Val His Arg Phe Ser Asp Lys Asn Phe
        680                 685                 690

ACG GGA ACC CCG CAG ACG ATG CCT GGC AAT ACC TTT GCC TTT ACC GGC     2208
Thr Gly Thr Pro Gln Thr Met Pro Gly Asn Thr Phe Ala Phe Thr Gly
695                 700                 705                 710

TAT CAG AAT CGA GGC ACG GAA AAT AAC CGC GTG GTG TTT GAT GCC AAG     2256
Tyr Gln Asn Arg Gly Thr Glu Asn Asn Arg Val Val Phe Asp Ala Lys
                715                 720                 725

GGC GTG GAG TTC TGC GAC GCC ATG CCG CCC GGC CAA AGC GGT TTC ACC     2304
Gly Val Glu Phe Cys Asp Ala Met Pro Pro Gly Gln Ser Gly Phe Thr
            730                 735                 740

GAC CGC AAT GGA GTG CGC AGC CCG CAT TAT GAG GAT CAG CTG AAG TTG     2352
Asp Arg Asn Gly Val Arg Ser Pro His Tyr Glu Asp Gln Leu Lys Leu
        745                 750                 755

TAC GAG AAC TTC GAG TGC AAG ACG ATG GAT GTG ACG CAT GCG GAC ATT     2400
Tyr Glu Asn Phe Glu Cys Lys Thr Met Asp Val Thr His Ala Asp Ile
760                 765                 770

CGT CGT AAT GCG CAA AGC AGC ACG ATG CTG TTG ATT CAG CCT CAG CCT     2448
Arg Arg Asn Ala Gln Ser Ser Thr Met Leu Leu Ile Gln Pro Gln Pro
775                 780                 785                 790

TAA                                                                 2451

(2) INFORMATION FOR SEQ ID NO: 4:

(i) SEQUENCE CHARACTERISTICS:
        (A) LENGTH: 816 amino acids
        (B) TYPE: amino acid
        (D) TOPOLOGY: linear (ii) MOLECULE TYPE: protein (xi) SEQUENCE DESCRIPTION: SEQ ID NO: 4:

Met Gln Lys Gly Leu Val Arg Thr Gly Leu Val Ala Ala Gly Leu Ile
-26 -25                 -20                 -15

Leu Gly Trp Ala Gly Ala Pro Thr His Ala Gln Val Gln Ser Val Glu
-10                  -5                   1                   5

Val Met Arg Asp Ser Tyr Gly Val Pro His Val Phe Ala Asp Ser His
                 10                  15                  20

Tyr Gly Leu Tyr Tyr Gly Tyr Gly Tyr Ala Val Ala Gln Asp Arg Leu
             25                  30                  35

Phe Gln Met Asp Met Ala Arg Arg Ser Phe Val Gly Thr Thr Ala Ala
         40                  45                  50

Val Leu Gly Pro Gly Glu Gln Asp Ala Tyr Val Lys Tyr Asp Met Gln
55                   60                  65                  70

Val Arg Gln Asn Phe Thr Pro Ala Ser Ile Gln Arg Gln Ile Ala Ala
                 75                  80                  85

Leu Ser Lys Asp Glu Arg Asp Ile Phe Arg Gly Tyr Ala Asp Gly Tyr
             90                  95                  100

Asn Ala Tyr Leu Glu Gln Val Arg Arg Pro Glu Leu Leu Pro Lys
         105                 110                 115

Glu Tyr Val Asp Phe Asp Phe Gln Pro Glu Pro Leu Thr Asp Phe Asp
     120                 125                 130

Val Val Met Ile Trp Val Gly Ser Met Ala Asn Arg Phe Ser Asp Thr
135                 140                 145                 150

Asn Leu Glu Val Thr Ala Leu Ala Met Arg Gln Ser Leu Glu Lys Gln
                 155                 160                 165
```

His Gly Pro Glu Arg Gly Arg Ala Leu Phe Asp Glu Leu Leu Trp Ile
                170                 175                 180

Asn Asp Thr Thr Ala Pro Thr Thr Val Pro Ala Pro Ala Ala Glu His
            185                 190                 195

Lys Pro Gln Ala Gln Ala Gly Thr Gln Asp Leu Ala His Val Ser Ser
200                 205                 210

Pro Val Leu Ala Thr Glu Leu Arg Gln Asp Lys His Trp Gly Gly
215                 220                 225                 230

Arg Gly Pro Asp Phe Ala Pro Lys Ala Ser Asn Leu Trp Ser Thr Arg
                235                 240                 245

Pro Glu Arg Val Gln Glu Gly Ser Thr Val Leu Ile Asn Gly Pro Gln
                250                 255                 260

Phe Gly Trp Tyr Asn Pro Ala Tyr Thr Tyr Gly Ile Gly Leu His Gly
                265                 270                 275

Ala Gly Phe Asp Val Val Gly Asn Thr Pro Phe Ala Tyr Pro Ile Val
            280                 285                 290

Leu Phe Gly Thr Asn Ser Glu Ile Ala Trp Gly Ala Thr Ala Gly Pro
295                 300                 305                 310

Gln Asp Val Val Asp Ile Tyr Gln Glu Lys Leu Asn Pro Ser Arg Ala
                315                 320                 325

Asp Gln Tyr Trp Phe Asn Asn Ala Trp Arg Thr Met Glu Gln Arg Lys
                330                 335                 340

Glu Arg Ile Gln Val Arg Gly Gln Ala Asp Arg Glu Met Thr Ile Trp
            345                 350                 355

Arg Thr Val His Gly Pro Val Met Gln Phe Asp Tyr Asp Gln Gly Ala
360                 365                 370

Ala Tyr Ser Lys Lys Arg Ser Trp Asp Gly Tyr Glu Val Gln Ser Leu
375                 380                 385                 390

Leu Ala Trp Leu Asn Val Ala Lys Ala Arg Asn Trp Thr Glu Phe Leu
                395                 400                 405

Asp Gln Ala Ser Lys Met Ala Ile Ser Ile Asn Trp Tyr Tyr Ala Asp
                410                 415                 420

Lys His Gly Asn Ile Gly Tyr Val Ser Pro Ala Phe Leu Pro Gln Arg
            425                 430                 435

Pro Ala Asp Gln Asp Ile Arg Val Pro Ala Lys Gly Asp Gly Ser Met
            440                 445                 450

Glu Trp Leu Gly Ile Lys Ser Phe Asp Ala Ile Pro Lys Ala Tyr Asn
455                 460                 465                 470

Pro Pro Gln Gly Tyr Leu Val Asn Trp Asn Asn Lys Pro Ala Pro Asp
                475                 480                 485

Lys Thr Asn Thr Asp Thr Tyr Tyr Trp Thr Tyr Gly Asp Arg Met Asn
            490                 495                 500

Glu Leu Val Ser Gln Tyr Gln Gln Lys Asp Leu Phe Ser Val Gln Glu
            505                 510                 515

Ile Trp Glu Phe Asn Gln Lys Ala Ser Tyr Ser Asp Val Asn Trp Arg
520                 525                 530

Tyr Phe Arg Pro His Leu Glu Lys Leu Ala Gln Leu Pro Ala Asp
535                 540                 545                 550

Asp Ser Ser Lys Ala Ala Leu Thr Met Leu Leu Ala Trp Asp Gly Met
                555                 560                 565

Glu Gln Asp Gln Gly Gly Gln Asn Ala Gly Pro Ala Arg Val Leu Phe
                570                 575                 580

Lys Thr Trp Leu Glu Glu Met Tyr Lys Gln Val Leu Met Pro Val Val
            585                 590                 595

-continued

```
Pro Glu Ser His Arg Ala Met Tyr Ser Gln Thr Gly Phe Ala Thr Gln
    600                 605                 610

Gln Gly Pro Asn Pro Gly Ser Ile Asn Leu Ser Met Gly Thr Lys Val
615                 620                 625                 630

Leu Leu Arg Ala Leu Val Leu Glu Ala His Pro Asp Pro Lys Arg Val
                635                 640                 645

Asn Val Phe Gly Glu Arg Ser Ser Gln Glu Ile Met His Thr Ala Leu
                650                 655                 660

Gln Asn Ala Gln Ala Arg Leu Ser Gln Glu Gln Gly Ala Gln Met Ala
                665                 670                 675

Arg Trp Thr Met Pro Thr Ser Val His Arg Phe Ser Asp Lys Asn Phe
    680                 685                 690

Thr Gly Thr Pro Gln Thr Met Pro Gly Asn Thr Phe Ala Phe Thr Gly
695                 700                 705                 710

Tyr Gln Asn Arg Gly Thr Glu Asn Asn Arg Val Val Phe Asp Ala Lys
                715                 720                 725

Gly Val Glu Phe Cys Asp Ala Met Pro Pro Gly Gln Ser Gly Phe Thr
                730                 735                 740

Asp Arg Asn Gly Val Arg Ser Pro His Tyr Glu Asp Gln Leu Lys Leu
                745                 750                 755

Tyr Glu Asn Phe Glu Cys Lys Thr Met Asp Val Thr His Ala Asp Ile
    760                 765                 770

Arg Arg Asn Ala Gln Ser Ser Thr Met Leu Leu Ile Gln Pro Gln Pro
775                 780                 785                 790

(2) INFORMATION FOR SEQ ID NO: 5:

(i) SEQUENCE CHARACTERISTICS:
        (A) LENGTH: 846 amino acids
        (B) TYPE: amino acid
        (D) TOPOLOGY: linear (ii) MOLECULE TYPE: protein (vi) ORIGINAL SOURCE:
        (A) ORGANISM: Escherichia coli (x) PUBLICATION INFORMATION:
        (A) AUTHORS: Schumacher, G
            Sizmann, D
            Haug, H
            Buckel, P
            Bock, A
        (B) TITLE: Penicillin acylase from E.coli: unique
            gene-protein realtion.
        (C) JOURNAL: Nucleic Acids Res.
        (D) VOLUME: 14
        (F) PAGES: 5713-5727
        (G) DATE: 1986

(xi) SEQUENCE DESCRIPTION: SEQ ID NO: 5:

Met Lys Asn Arg Asn Arg Met Ile Val Asn Cys Val Thr Ala Ser Leu
   1               5                   10                  15

Met Tyr Tyr Trp Ser Leu Pro Ala Leu Ala Glu Gln Ser Ser Ser Glu
                   20                  25                  30

Ile Lys Ile Val Arg Asp Glu Tyr Gly Met Pro His Ile Tyr Ala Asn
                   35                  40                  45

Asp Thr Trp His Leu Phe Tyr Gly Tyr Gly Tyr Val Val Ala Gln Asp
                   50                  55                  60

Arg Leu Phe Gln Met Glu Met Ala Arg Arg Ser Thr Gln Gly Thr Val
   65                  70                  75                  80
```

-continued

```
Ala Glu Val Leu Gly Lys Asp Phe Val Lys Phe Asp Lys Asp Ile Arg
                85                  90                  95
Arg Asn Tyr Trp Pro Asp Ala Ile Arg Ala Gln Ile Ala Ala Leu Ser
            100                 105                 110
Pro Glu Asp Met Ser Ile Leu Gln Gly Tyr Ala Asp Gly Met Asn Ala
        115                 120                 125
Trp Ile Asp Lys Val Asn Thr Asn Pro Glu Thr Leu Leu Pro Lys Gln
130                 135                 140
Phe Asn Thr Phe Gly Phe Thr Pro Lys Arg Trp Glu Pro Phe Asp Val
145                 150                 155                 160
Ala Met Ile Phe Val Gly Thr Met Ala Asn Arg Phe Ser Asp Ser Thr
                165                 170                 175
Ser Glu Ile Asp Asn Leu Ala Leu Leu Thr Ala Leu Lys Asp Lys Tyr
            180                 185                 190
Gly Val Ser Gln Gly Met Ala Val Phe Asn Gln Leu Lys Trp Leu Val
        195                 200                 205
Asn Pro Ser Ala Pro Thr Thr Ile Ala Val Gln Glu Ser Asn Tyr Pro
210                 215                 220
Leu Lys Phe Asn Gln Gln Asn Ser Gln Thr Ala Ala Leu Leu Pro Arg
225                 230                 235                 240
Tyr Asp Leu Pro Ala Pro Met Leu Asp Arg Pro Ala Lys Gly Ala Asp
                245                 250                 255
Gly Ala Leu Leu Ala Leu Thr Ala Gly Lys Asn Arg Glu Thr Ile Val
            260                 265                 270
Ala Gln Phe Ala Gln Gly Gly Ala Asn Gly Leu Ala Gly Tyr Pro Thr
        275                 280                 285
Thr Ser Asn Met Trp Val Ile Gly Lys Ser Lys Ala Gln Asp Ala Lys
290                 295                 300
Ala Ile Met Val Asn Gly Pro Gln Phe Gly Trp Tyr Ala Pro Ala Tyr
305                 310                 315                 320
Thr Tyr Gly Ile Gly Leu His Gly Ala Gly Tyr Asp Val Thr Gly Asn
                325                 330                 335
Thr Pro Phe Ala Tyr Pro Gly Leu Val Phe Gly His Asn Gly Val Ile
            340                 345                 350
Ser Trp Gly Ser Thr Ala Gly Phe Gly Asp Asp Val Asp Ile Phe Ala
        355                 360                 365
Glu Arg Leu Ser Ala Glu Lys Pro Gly Tyr Tyr Leu His Asn Gly Lys
370                 375                 380
Trp Val Lys Met Leu Ser Arg Glu Glu Thr Ile Thr Val Lys Asn Gly
385                 390                 395                 400
Gln Ala Glu Thr Phe Thr Val Trp Arg Thr Val His Gly Asn Ile Leu
                405                 410                 415
Gln Thr Asp Gln Thr Thr Gln Thr Ala Tyr Ala Lys Ser Arg Ala Trp
            420                 425                 430
Asp Gly Lys Glu Val Ala Ser Leu Leu Ala Trp Thr His Gln Met Lys
        435                 440                 445
Ala Lys Asn Trp Gln Glu Trp Thr Gln Gln Ala Ala Lys Gln Ala Leu
450                 455                 460
Thr Ile Asn Trp Tyr Tyr Ala Asp Val Asn Gly Asn Ile Gly Tyr Val
465                 470                 475                 480
His Thr Gly Ala Tyr Pro Asp Arg Gln Ser Gly His Asp Pro Arg Leu
                485                 490                 495
Pro Val Pro Gly Thr Gly Lys Trp Asp Trp Lys Gly Leu Leu Pro Phe
            500                 505                 510
```

```
Glu Met Asn Pro Lys Val Tyr Asn Pro Gln Ser Gly Tyr Ile Ala Asn
    515                 520                 525

Trp Asn Asn Ser Pro Gln Lys Asp Tyr Pro Ala Ser Asp Leu Phe Ala
    530                 535                 540

Phe Leu Trp Gly Gly Ala Asp Arg Val Thr Glu Ile Asp Arg Leu Leu
545                 550                 555                 560

Glu Gln Lys Pro Arg Leu Thr Ala Asp Gln Ala Trp Asp Val Ile Arg
                565                 570                 575

Gln Thr Ser Arg Gln Asp Leu Asn Leu Arg Leu Phe Leu Pro Thr Leu
            580                 585                 590

Gln Ala Ala Thr Ser Gly Leu Thr Gln Ser Asp Pro Arg Arg Gln Leu
        595                 600                 605

Val Glu Thr Leu Thr Arg Trp Asp Gly Ile Asn Leu Leu Asn Asp Asp
    610                 615                 620

Gly Lys Thr Trp Gln Gln Pro Gly Ser Ala Ile Leu Asn Val Trp Leu
625                 630                 635                 640

Thr Ser Met Leu Lys Arg Thr Val Val Ala Val Pro Met Pro Phe
                645                 650                 655

Asp Lys Trp Tyr Ser Ala Ser Gly Tyr Glu Thr Thr Gln Asp Gly Pro
                660                 665                 670

Thr Gly Ser Leu Asn Ile Ser Val Gly Ala Lys Ile Leu Tyr Glu Ala
            675                 680                 685

Val Gln Gly Asp Lys Ser Pro Ile Pro Gln Ala Val Asp Leu Phe Ala
        690                 695                 700

Gly Lys Pro Gln Gln Glu Val Val Leu Ala Ala Leu Glu Asp Thr Trp
705                 710                 715                 720

Glu Thr Leu Ser Lys Arg Tyr Gly Asn Asn Val Ser Asn Trp Lys Thr
                725                 730                 735

Pro Ala Met Ala Leu Thr Phe Arg Ala Asn Asn Phe Phe Gly Val Pro
                740                 745                 750

Gln Ala Ala Ala Glu Glu Thr Arg His Gln Ala Glu Tyr Gln Asn Arg
            755                 760                 765

Gly Thr Glu Asn Asp Met Ile Val Phe Ser Pro Thr Thr Ser Asp Arg
        770                 775                 780

Pro Val Leu Ala Trp Asp Val Val Ala Pro Gly Gln Ser Gly Phe Ile
785                 790                 795                 800

Ala Pro Asp Gly Thr Val Asp Lys His Tyr Glu Asp Gln Leu Lys Met
                805                 810                 815

Tyr Glu Asn Phe Gly Arg Lys Ser Leu Trp Leu Thr Lys Gln Asp Val
                820                 825                 830

Glu Ala His Lys Glu Ser Gln Glu Val Leu His Val Gln Arg
            835                 840                 845
```

(2) INFORMATION FOR SEQ ID NO: 6:

(i) SEQUENCE CHARACTERISTICS:
      (A) LENGTH: 844 amino acids
      (B) TYPE: amino acid
      (D) TOPOLOGY: linear (ii) MOLECULE TYPE: protein (iii) HYPOTHETICAL: NO (vi) ORIGINAL SOURCE:
      (A) ORGANISM: Kluyvera citrophila
      (B) STRAIN: ATCC 21285

(xi) SEQUENCE DESCRIPTION: SEQ ID NO: 6:

```
Met Lys Asn Arg Asn Arg Met Ile Val Asn Gly Ile Val Thr Ser Leu
  1               5                  10                  15

Ile Cys Cys Ser Ser Leu Ser Ala Leu Ala Ser Pro Pro Thr Glu
             20                  25                  30

Val Lys Ile Val Arg Asp Glu Tyr Gly Met Pro His Ile Tyr Ala Asp
             35                  40                  45

Asp Thr Tyr Arg Leu Phe Tyr Gly Tyr Gly Tyr Val Val Ala Gln Asp
         50                  55                  60

Arg Leu Phe Gln Met Glu Met Ala Arg Arg Ser Thr Gln Gly Thr Val
 65                  70                  75                  80

Ser Glu Val Leu Gly Lys Ala Phe Val Ser Phe Asp Lys Asp Ile Arg
                 85                  90                  95

Gln Asn Tyr Trp Pro Asp Ser Ile Arg Ala Gln Ile Ala Ser Leu Ser
                100                 105                 110

Ala Glu Asp Lys Ser Ile Leu Gln Gly Tyr Ala Asp Gly Met Asn Ala
            115                 120                 125

Trp Ile Asp Lys Val Asn Ala Ser Pro Asp Lys Leu Leu Pro Gln Gln
        130                 135                 140

Phe Ser Thr Phe Gly Phe Lys Pro Lys His Trp Glu Pro Phe Asp Val
145                 150                 155                 160

Ala Met Ile Phe Val Gly Thr Met Ala Asn Arg Phe Ser Asp Ser Thr
                165                 170                 175

Ser Glu Ile Asp Asn Leu Ala Leu Leu Thr Ala Val Lys Asp Lys Tyr
            180                 185                 190

Gly Asn Asp Glu Gly Met Ala Val Phe Asn Gln Leu Lys Trp Leu Val
        195                 200                 205

Asn Pro Ser Ala Pro Thr Thr Ile Ala Ala Arg Glu Ser Ser Tyr Pro
210                 215                 220

Leu Lys Phe Asp Leu Gln Asn Thr Gln Thr Ala Ala Leu Leu Val Pro
225                 230                 235                 240

Arg Tyr Asp Gln Pro Ala Pro Met Leu Asp Arg Pro Ala Lys Gly Thr
                245                 250                 255

Asp Gly Ala Leu Leu Ala Val Thr Ala Ile Lys Asn Arg Glu Thr Ile
            260                 265                 270

Ala Ala Gln Phe Ala Asn Gly Ala Asn Gly Leu Ala Gly Tyr Pro Thr
        275                 280                 285

Thr Ser Asn Met Trp Val Ile Gly Lys Asn Lys Ala Gln Asp Ala Lys
290                 295                 300

Ala Ile Met Val Asn Gly Pro Gln Phe Gly Trp Tyr Ala Pro Ala Tyr
305                 310                 315                 320

Thr Tyr Gly Ile Gly Leu His Gly Ala Gly Tyr Asp Val Thr Gly Asn
                325                 330                 335

Thr Pro Phe Ala Tyr Pro Gly Leu Val Phe Gly His Asn Gly Thr Ile
            340                 345                 350

Ser Trp Gly Ser Thr Ala Gly Phe Gly Asp Asp Val Asp Ile Phe Ala
        355                 360                 365

Glu Lys Leu Ser Ala Glu Lys Pro Gly Tyr Tyr Gln His Asn Gly Glu
370                 375                 380

Trp Val Lys Met Leu Ser Arg Lys Glu Thr Ile Ala Val Lys Asp Gly
385                 390                 395                 400

Gln Pro Glu Thr Phe Thr Val Trp Arg Thr Leu Asp Gly Asn Val Ile
                405                 410                 415
```

```
Lys Thr Asp Thr Arg Thr Gln Thr Ala Tyr Ala Lys Ala Arg Ala Trp
            420                 425                 430

Ala Gly Lys Glu Val Ala Ser Leu Leu Ala Trp Thr His Gln Met Lys
            435                 440                 445

Ala Lys Asn Trp Pro Glu Trp Thr Gln Gln Ala Ala Lys Gln Ala Leu
            450                 455                 460

Thr Ile Asn Trp Tyr Tyr Ala Asp Val Asn Gly Asn Ile Gly Tyr Val
465                 470                 475                 480

His Thr Gly Ala Tyr Pro Asp Arg Gln Pro Gly His Asp Pro Arg Leu
                485                 490                 495

Pro Val Pro Asp Gly Lys Trp Asp Trp Lys Gly Leu Leu Ser Phe Asp
            500                 505                 510

Leu Asn Pro Lys Val Tyr Asn Pro Gln Ser Gly Tyr Ile Ala Asn Trp
            515                 520                 525

Asn Asn Ser Pro Gln Lys Asp Tyr Pro Ala Ser Asp Leu Phe Ala Phe
            530                 535                 540

Leu Trp Gly Gly Ala Asp Arg Val Thr Glu Ile Asp Thr Ile Leu Asp
545                 550                 555                 560

Lys Gln Pro Arg Phe Thr Ala Asp Gln Ala Trp Asp Val Ile Arg Gln
                565                 570                 575

Thr Ser Leu Arg Asp Leu Leu Arg Leu Phe Leu Pro Ala Leu Lys Asp
            580                 585                 590

Ala Thr Ala Asn Leu Ala Glu Asn Asp Pro Arg Arg Gln Leu Val Asp
            595                 600                 605

Lys Leu Ala Ser Trp Asp Gly Glu Asn Leu Val Asn Asp Asp Gly Lys
            610                 615                 620

Thr Tyr Gln Gln Pro Gly Ser Ala Ile Leu Asn Ala Trp Leu Thr Ser
625                 630                 635                 640

Met Leu Lys Arg Thr Val Val Ala Ala Val Pro Ala Pro Phe Gly Lys
                645                 650                 655

Trp Tyr Ser Ala Ser Gly Tyr Glu Thr Thr Gln Asp Gly Pro Thr Gly
                660                 665                 670

Ser Leu Asn Ile Ser Val Gly Ala Lys Ile Leu Tyr Glu Ala Leu Gln
            675                 680                 685

Gly Asp Lys Ser Pro Ile Pro Gln Ala Val Asp Leu Phe Gly Gly Lys
            690                 695                 700

Pro Glu Gln Glu Val Ile Leu Ala Ala Leu Asp Asp Ala Trp Glu Thr
705                 710                 715                 720

Leu Ser Lys Arg Tyr Gly Asn Asp Val Thr Gly Trp Lys Thr Pro Ala
                725                 730                 735

Met Ala Leu Thr Phe Arg Ala Asn Asn Phe Phe Gly Val Pro Gln Ala
                740                 745                 750

Ala Ala Lys Glu Ala Arg His Gln Ala Glu Tyr Gln Asn Arg Gly Thr
            755                 760                 765

Glu Asn Asp Met Ile Val Phe Ser Pro Thr Ser Gly Asn Arg Pro Val
770                 775                 780

Leu Ala Trp Asp Val Val Ala Pro Gly Gln Ser Gly Phe Ile Ala Pro
785                 790                 795                 800

Asp Gly Lys Ala Asp Lys His Tyr Asp Asp Gln Leu Lys Met Tyr Glu
                805                 810                 815

Ser Phe Gly Arg Lys Ser Leu Trp Leu Thr Pro Gln Asp Val Asp Glu
                820                 825                 830

His Lys Glu Ser Gln Glu Val Leu Gln Val Gln Arg
            835                 840
```

(2) INFORMATION FOR SEQ ID NO: 7:

(i) SEQUENCE CHARACTERISTICS:
        (A) LENGTH: 774 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Pseudomonas species
        (B) STRAIN: SE83

(xi) SEQUENCE DESCRIPTION: SEQ ID NO: 7:

```
Met Thr Met Ala Ala Lys Thr Asp Arg Glu Ala Leu Gln Ala Ala Leu
  1               5                  10                  15

Pro Pro Leu Ser Gly Ser Leu Ser Ile Pro Gly Leu Ser Ala Pro Val
             20                  25                  30

Arg Val Gln Arg Asp Gly Trp Gly Ile Pro His Ile Lys Ala Ser Gly
             35                  40                  45

Glu Ala Asp Ala Tyr Arg Ala Leu Gly Phe Val His Ala Gln Asp Arg
 50                  55                  60

Leu Phe Gln Met Glu Leu Thr Arg Arg Lys Ala Leu Gly Arg Ala Ala
 65                  70                  75                  80

Glu Trp Leu Gly Ala Glu Ala Ala Glu Ala Asp Ile Leu Val Arg Arg
                 85                  90                  95

Leu Gly Met Glu Lys Val Cys Arg Arg Asp Phe Glu Ala Leu Gly Ala
                100                 105                 110

Glu Ala Lys Asp Met Leu Arg Ala Tyr Val Ala Gly Val Asn Ala Phe
            115                 120                 125

Leu Ala Ser Gly Ala Pro Leu Pro Ile Glu Tyr Gly Leu Leu Gly Ala
        130                 135                 140

Glu Pro Glu Pro Trp Glu Pro Trp His Ser Ile Ala Val Met Arg Arg
145                 150                 155                 160

Leu Gly Leu Leu Met Gly Ser Val Trp Phe Lys Leu Trp Arg Met Leu
                165                 170                 175

Ala Leu Pro Val Val Gly Ala Ala Asn Ala Leu Lys Leu Arg Tyr Asp
            180                 185                 190

Asp Gly Gly Gln Asp Leu Leu Cys Ile Pro Pro Gly Val Glu Ala Glu
        195                 200                 205

Arg Leu Glu Ala Asp Leu Ala Ala Leu Arg Pro Ala Val Asp Ala Leu
    210                 215                 220

Leu Lys Ala Met Gly Gly Asp Ala Ser Asp Ala Ala Gly Gly Gly Ser
225                 230                 235                 240

Asn Asn Trp Ala Val Ala Pro Gly Arg Thr Ala Thr Gly Arg Pro Ile
                245                 250                 255

Leu Ala Gly Asp Pro His Arg Val Phe Glu Ile Pro Gly Met Tyr Ala
            260                 265                 270

Gln His His Leu Ala Cys Asp Arg Phe Asp Met Ile Gly Leu Thr Val
        275                 280                 285

Pro Gly Val Pro Gly Phe Pro His Phe Ala His Asn Gly Lys Val Ala
    290                 295                 300

Tyr Cys Val Thr His Ala Phe Met Asp Ile His Asp Leu Tyr Leu Glu
305                 310                 315                 320
```

```
Gln Phe Ala Glu Asp Gly Arg Thr Ala Arg Phe Gly Asn Glu Phe Glu
            325                 330                 335

Pro Val Ala Trp Arg Arg Asp Arg Ile Ala Val Arg Gly Gly Ala Asp
            340                 345                 350

Arg Glu Phe Asp Ile Val Glu Thr Arg His Gly Pro Val Ile Ala Gly
            355                 360                 365

Asp Pro Leu Glu Gly Ala Ala Leu Thr Leu Arg Ser Val Gln Phe Ala
            370                 375                 380

Glu Thr Asp Leu Ser Phe Asp Cys Leu Thr Arg Met Pro Gly Ala Ser
385                 390                 395                 400

Thr Val Ala Gln Leu Tyr Asp Ala Thr Arg Gly Trp Gly Leu Ile Asp
            405                 410                 415

His Asn Leu Val Ala Gly Asp Val Ala Gly Ser Ile Gly His Leu Val
            420                 425                 430

Arg Ala Arg Val Pro Ser Arg Pro Arg Glu Asn Gly Trp Leu Pro Val
            435                 440                 445

Pro Gly Trp Ser Gly Glu His Glu Trp Arg Gly Trp Ile Pro His Glu
            450                 455                 460

Ala Met Pro Arg Val Ile Asp Pro Pro Gly Gly Leu Ile Val Thr Ala
465                 470                 475                 480

Asn Asn Arg Val Val Ala Asp Asp His Pro Asp Tyr Leu Cys Thr Asp
            485                 490                 495

Cys His Pro Pro Tyr Arg Ala Glu Arg Ile Met Glu Arg Leu Val Ala
            500                 505                 510

Ser Pro Ala Phe Ala Val Asp Asp Ala Ala Ile His Ala Asp Thr
            515                 520                 525

Leu Ser Pro His Val Gly Leu Leu Arg Ala Arg Leu Glu Ala Leu Gly
            530                 535                 540

Ile Gln Gly Ser Leu Pro Ala Glu Glu Leu Arg Gln Thr Leu Ile Ala
545                 550                 555                 560

Trp Asp Gly Arg Met Asp Ala Gly Ser Gln Ala Ala Ser Ala Tyr Asn
            565                 570                 575

Ala Phe Arg Arg Ala Leu Thr Arg Leu Val Thr Ala Arg Ser Gly Leu
            580                 585                 590

Glu Gln Ala Ile Ala His Pro Phe Ala Ala Val Pro Pro Gly Val Ser
            595                 600                 605

Pro Gln Gly Gln Val Trp Trp Ala Val Pro Thr Leu Leu Arg Asn Asp
            610                 615                 620

Asp Ala Gly Met Leu Lys Gly Trp Ser Trp Asp Glu Ala Leu Ser Glu
625                 630                 635                 640

Ala Leu Ser Val Ala Thr Gln Asn Leu Thr Gly Arg Gly Trp Gly Glu
            645                 650                 655

Glu His Arg Pro Arg Phe Thr His Pro Leu Ser Ala Gln Phe Pro Ala
            660                 665                 670

Trp Ala Ala Leu Leu Asn Pro Val Ser Arg Pro Ile Gly Gly Asp Gly
            675                 680                 685

Asp Thr Val Leu Ala Asn Gly Leu Val Pro Ser Ala Gly Pro Glu Ala
            690                 695                 700

Thr Tyr Gly Ala Leu Ser Arg Tyr Val Phe Asp Val Gly Asn Trp Asp
705                 710                 715                 720

Asn Ser Arg Trp Val Val Phe His Gly Ala Ser Gly His Pro Ala Ser
            725                 730                 735

Pro His Tyr Ala Asp Gln Asn Ala Pro Trp Ser Asp Cys Ala Met Val
            740                 745                 750
```

```
    Pro Met Leu Tyr Ser Trp Asp Arg Ile Ala Ala Glu Ala Val Thr Ser
        755                 760                 765

Gln Glu Leu Val Pro Ala
        770
```

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 8:

```
TCGTACATTT TCAGCTGATC TTCATAGTGC TTATC                                    35
```

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: N-terminal (xi) SEQUENCE DESCRIPTION: SEQ ID NO: 9:

```
    Ser Asn Leu Trp Ser Xaa Cys Pro Glu Cys Val
    1               5                   10
```

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iii) ANTI-SENSE: NO (xi) SEQUENCE DESCRIPTION: SEQ ID NO: 10:

```
AGCAACCTGT GGAGCMSCTG CCCGGAGTGC GT                                       32
```

(2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 11:

ATGCTGAGAG TTCTGCACCG GGCGGCGTCC GCCTTG        36

(2) INFORMATION FOR SEQ ID NO: 12:

(i) SEQUENCE CHARACTERISTICS:
          (A) LENGTH: 54 base pairs
          (B) TYPE: nucleic acid
          (C) STRANDEDNESS: single
          (D) TOPOLOGY: linear (ii) MOLECULE TYPE: DNA (synthetic)

(iii) HYPOTHETICAL: NO (xi) SEQUENCE DESCRIPTION: SEQ ID NO: 12:

CGGCCGATGC TCCTCGCCCC AGCCGCGCCC GGTCAGGTTC TGCGTCGCGA CGGA        54

(2) INFORMATION FOR SEQ ID NO: 13:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 13:

Glu Gln Ser Ser Ser
    1               5

(2) INFORMATION FOR SEQ ID NO: 14:

(i) SEQUENCE CHARACTERISTICS:
          (A) LENGTH: 3 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO: 14:

Gln Thr Ala
    1

(2) INFORMATION FOR SEQ ID NO: 15:

(i) SEQUENCE CHARACTERISTICS:
          (A) LENGTH: 3 amino acids
          (B) TYPE: amino acid
          (C) STRANDEDNESS: single
          (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 15:

Ser Asn Met
    1

(2) INFORMATION FOR SEQ ID NO: 16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 16:

Glu Gln Ser Ser Ser Glu Ile
    1               5

(2) INFORMATION FOR SEQ ID NO: 17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO: 17:

Asn Gln Gln Asn Ser Gln Thr Ala
    1               5

(2) INFORMATION FOR SEQ ID NO: 18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 18:

Ser Asn Met Trp Val Ile Gly
    1               5

(2) INFORMATION FOR SEQ ID NO: 19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 19:

Ala Ser Pro Pro Thr Glu Val Lys
    1               5

```
(2) INFORMATION FOR SEQ ID NO: 20:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO: 20:

Thr Gln Thr Ala
   1

(2) INFORMATION FOR SEQ ID NO: 21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 21:

Ser Asn Met Trp Val Ile Gly Lys
   1               5

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 22:

Gln Xaa Gln Xaa Val Glu Val Met Xaa Thr
   1               5                   10

(2) INFORMATION FOR SEQ ID NO: 23:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 23:

Ser Asn Leu Trp Ser Thr Xaa Pro Glu Xaa Val
   1               5                   10
```

(2) INFORMATION FOR SEQ ID NO: 24:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 24:

Thr Met Ala Ala Lys Thr
     1               5

(2) INFORMATION FOR SEQ ID NO: 25:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 25:

Ser Asn Asn Trp Ala
     1               5

(2) INFORMATION FOR SEQ ID NO: 26:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 26:

Glu Pro Thr Ser Thr Pro Gln Ala
     1               5

(2) INFORMATION FOR SEQ ID NO: 27:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 27:

Ser Asn Ser Xaa Ala Val Ala
     1               5

(2) INFORMATION FOR SEQ ID NO: 28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 28:

```
CAGAACTCTC AGCATATGTT TCCCCTCTCA                                    30
```

(2) INFORMATION FOR SEQ ID NO: 29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 29:

```
AGGTCCAGAC AGCATATGAC GATGGCG                                       27
```

(2) INFORMATION FOR SEQ ID NO: 30:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 30:

```
GCCCTGGCTG CGCGCCTGGG CCCAGCCATA GCCGTAGAAG GCTGAGGGCG CGTCTACGCC   60

GTAGATGTGC GGGACGCCGT AGCCGTCCCA CAG                                93
```

(2) INFORMATION FOR SEQ ID NO: 31:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 31:

```
CCAGACGGTC GTCTGTTCGT AATCCGGTCC CCAGTATTCG GCCCCCTTGC CCCGCGCTTC   60

TCCATACAGG CGCAGGATAT TGTC                                         84
```

(2) INFORMATION FOR SEQ ID NO: 32:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 32:

GAATGCGTCG AGGTTGGCGC GGAAATCAGG CGACTGCTGC GCATACCACT GCTGAGCGCG    60

CTCCGGCACG CCGTTGGTCA GCAG    84

(2) INFORMATION FOR SEQ ID NO: 33:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 33:

GGCGCCGGAA ACCGGCAGCA CCTGCCGCAC GTCGGGCGAG ATGTCGTCGG GGTTCTGCTG    60

CGCATAGGCG TTGATGCCCG CTGC    84

(2) INFORMATION FOR SEQ ID NO: 34:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 34:

CGGCGGGTCG CCCTCGCCCA GGGTGCGCCC GGGCGACGCG ACATAGAGGA AGTTCATCAG    60

GCGGTGGGCG TGGGCCACCA CGTC    84

(2) INFORMATION FOR SEQ ID NO: 35:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 35:

GCCCAGGGTG CGGCCGGGCG ANNNNNNNNN NNNNNNGTTC ATCAGGCGGT GGGCGTGGGC    60

(2) INFORMATION FOR SEQ ID NO: 36:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 36:

ATAGCCGTAG AAGGCTGAGG GNNNNNNNNN NNNNNNGATG TGCGGGACGC CGTAGCC        57

(2) INFORMATION FOR SEQ ID NO: 37:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 37:

GCTGCGCGCC TGNNNNNNGC CNNNGCCNNN GAANNNTGAG GGCGCGTC        48

(2) INFORMATION FOR SEQ ID NO: 38:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 38:

ATAGTTGGTG GCCCCCACCA TGCCGTTAAC GGTATTGGTG ATGCCCATCC GCTGGTTGAA        60

GGCGAAGCGG ATGAC        75

(2) INFORMATION FOR SEQ ID NO: 39:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 39:

CTCGGCCCGT TGGGCGCCA CGCCGTTGAA GCTGTAGTTG ATGGTACCTT CGCGGTCGGC        60

GTAGACGATG TTGAA        75

(2) INFORMATION FOR SEQ ID NO: 40:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 40:

ATTGGAATTC TGCACGAAGC CGCCCGGCGG ATTGGTGACG CGCGGCAGAT CGTCCAGCGG        60

GTGTGTCTCG GTCCACAGGT AACG        84

(2) INFORMATION FOR SEQ ID NO: 41:

(i) SEQUENCE CHARACTERISTICS:

(A) LENGTH: 75 base pairs
    (B) TYPE: nucleic acid
    (C) STRANDEDNESS: single
    (D) TOPOLOGY: linear (ii) MOLECULE TYPE: DNA (synthetic)

(iii) HYPOTHETICAL: NO (xi) SEQUENCE DESCRIPTION: SEQ ID NO: 41:

```
CAGCAGGCGC GCCGCCGCCT GGACCTCGGG ATCGGGATCG ATCAGGGCGG CCGGGATCAG    60

GTCCGGCAAG GTGCG                                                    75
```

(2) INFORMATION FOR SEQ ID NO: 42:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 42:

```
GTCGGCGCGC GACACGCGTT CGATCTGATC GCTGTAGTGC GTCGTGCCCG GGTGGCGAGA    60

GTTGCCGTAG CTCATCAGGC CATA                                          84
```

(2) INFORMATION FOR SEQ ID NO: 43:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 43:

```
AAGGCGGTCC TGNNNNNNGA CNNNGCCNNN CGCNNNATAN NNATCGGCCT CGCC          54
```

(2) INFORMATION FOR SEQ ID NO: 44:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 44:

```
CCAGAGCTTG AACCAGACGG ANNNNNNNNN NNNNNNCAGC CGCCGCATCA CGGC          54
```

(2) INFORMATION FOR SEQ ID NO: 45:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 45:

CACCATCGCG CANNNGCTCC ANNNNNNATT CTGGTCGGCN NNGTGGGGGC TGGC          54

(2) INFORMATION FOR SEQ ID NO: 46:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 46:

GCCCTTTCTG CATATGTGTC CCTTATTTTT A                                   31

(2) INFORMATION FOR SEQ ID NO: 47:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 47:

CAGACGGTCT TGNNNNNNCG CNNNACCNNN GCCNNNATAN NNGCCATAGT GGCT          54

(2) INFORMATION FOR SEQ ID NO: 48:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO: 48:

TTCCAGATTC GTGTCGGANN NNNNNNNNNN NNNGGAGCCC ACCCAGATCA T             51

(2) INFORMATION FOR SEQ ID NO: 49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 49:

TCTATTTTTC ATATGATCCT CTGGCAG                                        27

(2) INFORMATION FOR SEQ ID NO: 50:

(i) SEQUENCE CHARACTERISTICS:
        (A) LENGTH: 51 base pairs
        (B) TYPE: nucleic acid
        (C) STRANDEDNESS: single
        (D) TOPOLOGY: linear -continued

```
    (ii) MOLECULE TYPE: DNA (synthetic)

(iii) HYPOTHETICAL: NO (xi) SEQUENCE DESCRIPTION: SEQ ID NO: 50:

TTCGCTAGTG CTATCAGANN NNNNNNNNNN NNNGGTGCCC ACAAATATCA T         51
```